(12) United States Patent
Coller et al.

(10) Patent No.: US 9,532,989 B2
(45) Date of Patent: Jan. 3, 2017

(54) OXADIAZOLO[3,2-A]PYRIMIDINES AND THIADIAZOLO[3,2-A]PYRIMIDINES

(71) Applicants: The United States of America, as Represented by the Secretary, Department of Health and Human Services, Washington, DC (US); The Rockefeller University, New York, NY (US); Icahn School of Medicine at Mount Sinai, New York, NY (US)

(72) Inventors: Barry S. Coller, New York, NY (US); Craig Thomas, Rockville, MD (US); Marta Filizola, New York, NY (US); Joshua McCoy, Portland, ME (US); Wenwei Huang, Rockville, MD (US); Min Shen, Boyds, MD (US)

(73) Assignees: THE UNITED STATES OF AMERICA AS REPRESENTED BY THE SECRETARY, DEPARTMENT OF HEALTH AND HUMAN SERVICES, Washington, DC (US); ICAHN SCHOOL OF MEDICINE AT MOUNT SINAI, New York, NY (US); THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 14/730,707

(22) Filed: Jun. 4, 2015

(65) Prior Publication Data
US 2015/0374697 A1  Dec. 31, 2015

Related U.S. Application Data

(62) Division of application No. 13/810,587, filed as application No. PCT/US2011/044267 on Jul. 15, 2011, now Pat. No. 9,066,948.
(Continued)

(51) Int. Cl.
| | | |
|---|---|---|
| A01N 43/90 | (2006.01) |
| A61K 31/519 | (2006.01) |
| C07D 487/04 | (2006.01) |
| A61K 31/497 | (2006.01) |
| A61K 45/06 | (2006.01) |
| C07D 513/04 | (2006.01) |

(52) U.S. Cl.
CPC ........... *A61K 31/519* (2013.01); *A61K 31/497* (2013.01); *A61K 45/06* (2013.01); *C07D 487/04* (2013.01); *C07D 513/04* (2013.01)

(58) Field of Classification Search
None
See application file for complete search history.

(56) References Cited

U.S. PATENT DOCUMENTS

| 4,265,898 A | 5/1981 | Horstmann et al. |
| 4,548,938 A | 10/1985 | Kennis et al. |

(Continued)

FOREIGN PATENT DOCUMENTS

| WO | 2008057601 A2 | 5/2008 |
| WO | 2009024615 A1 | 2/2009 |
| WO | 2012009688 A1 | 1/2012 |

OTHER PUBLICATIONS

International Preliminary Report on Patentability for International Patent Application No: PCT/US2013/021749; International Filing Date: Jan. 16, 2013; Date of Mailing: May 14, 2015; 2 Pages.
International Search Report of the International Searching Authority for International Patent Application No. PCT/US2013/21749; International Filing Date: Jan. 16, 2013; Date of mailing: Apr. 26, 2013; 4 Pages.
Written Opinion of the International Searching Authority; International Application No. PCT/US2013/021749; International Filing Date: Jan. 16, 2013; Date of Mailing: Apr. 26, 2013; 5 pages.
Basani et al. "Species differences in small molecule binding to allbβ3 are the result of sequence differences in 2 loops of the allb β propeller" Blood, vol. 113, (2009), pp. 902-910.
Blue et al., "Application of high-Throughput Screening to Identify a Novel a IIb-Specific Small-Molecule Inhibitor of allbβ3-Mediated Platelet Interaction with Fibrinogen" Blood, vol. 111, No. 3, Feb. 1, 2008, pp. 1248-1256.
Blue et al., "Structural and Thereapeutic Insights From the Species Specifically and in Vivo Antithrombotic Activity of a Novel a IIb-specific allbβ3 Antagonist", Blood, vol. 114, No. 1, Jul. 2, 2009, pp. 195-201.

(Continued)

*Primary Examiner* — Jeffrey H Murray
(74) *Attorney, Agent, or Firm* — Cantor Colburn LLP

(57) ABSTRACT

The present invention relates to compounds of Formula P-I

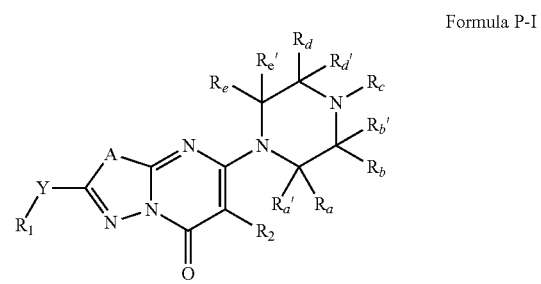

Formula P-I where the variables (e.g. $R_1$, Y, A, $R_1$, $R_a$, $R_{a'}$, $R_b$, $R_{b'}$, $R_c$, $R_{c'}$, $R_d$, $R_{d'}$, $R_e$, or $R_{e'}$) and compositions useful for inhibiting and/or reducing platelet deposition, adhesion and/or aggregation. The present invention further relates to methods for the treatment or prophylaxis of thrombotic disorders, including stroke, myocardial infarction, unstable angina, peripheral vascular disease, abrupt closure following angioplasty or stent placement and thrombosis as a result of vascular surgery.

12 Claims, No Drawings

Related U.S. Application Data

(60) Provisional application No. 61/365,152, filed on Jul. 16, 2010.

(56) References Cited

U.S. PATENT DOCUMENTS

| 8,173,661 | B2 | 5/2012 | Blue et al. | |
|---|---|---|---|---|
| 9,073,945 | B2 * | 7/2015 | Blue | C07D 513/04 |
| 9,303,044 | B2 * | 4/2016 | Coller | A61K 31/727 |
| 2010/0150913 | A1 | 6/2010 | Blue et al. | |
| 2015/0050325 | A1 | 2/2015 | Coller et al. | |

OTHER PUBLICATIONS

Chemical Abstract RN 946692-19-9. Retrieved from STN Mar. 25, 2014.
Eslin et al., "Transgenic mice studies demonstrate a role for platelet factor 4 in thrombosis: dissociation between anticoagulant and antithrombotic effect of heparin" Blood, vol. 104 (2004), pp. 3173-3180.
European Search Report and Supplemental Search Report for European Patent Application No. 11807604.1, Date of Mailing: Nov. 28, 2013, 11 Pages.
International Search Report of the International Searching Authority for International Patent Application no. PCT/US2011/44267, International Filing Date: Jul. 15, 2011, Date of Mailing: Dec. 6, 2011, 3 Pages
Jiang et al., "A Novel Class of Ion Displacement Ligands as Antagonista of the allbβ3 Receptor That Limit Conformational Reorganization of the Receptor", Bioorganic & Medicinal Chemistry Letters; 24, (2014); pp. 1148-1153.
Law et al., "Genetic and Pharmacological Analyses of Syk Function in allbβ3 Singnaling in Platelets" Blood, vol. 93, (1999), pp. 2645-2652.
McCoy et al., "Inhibitors of Platelet Integrin allbβ3" Probe Reports from the NIH Molecular Libraries Program—NCBI Bookshelf; Mar. 27, 2010, http://www.ncbi.nlm.nih.gov/books/NBK56230/#ml165.s1; 17 Pages.
Negri et al., " Structure-Based Virtual Screening of Small-Molecule Antagonists of Platelet Integrin allbβ3 that do not Prime the Receptor to Bind Ligand" Journal of Computer-Aided Molecular Design; vol. 26, Issue 9, Sep. 2012, Abstract Only.
Neyman et al. "Analysis of the spatial and temporal characteristics of platelet-delivered factor VIII-based clots" Blood, vol. 112, (2008), pp. 1101-1108.
Thornton et al., "Identification of distal regulator regions in the human allb gene locus necessary for consistent, high-level megakaryocyte expression" Blood, vol. 100, (2002), pp. 3588-3596.
Written Opinion of the International Searching Authority for International Patent Application No.PCT/US2011/44267, Issued Dec. 6, 2011.
Yarovoi et al. "Factor VIII ectopically expressed in platelets: eficacy in hemophilia a treatment" Blood, vol. 102, (2003), pp. 4006-4013.
Zhu et al., "Structure-Guided Design of a High-Affinity Platelet Intergin anion Receptor Antagonist That Disrupts MG2 + Binding to the MIDAS" Science Translational Medicine, vol. 4, Issue 125, Mar. 14, 2012, age 125ra32, Abstract Only.

* cited by examiner

OXADIAZOLO[3,2-A]PYRIMIDINES AND THIADIAZOLO[3,2-A]PYRIMIDINES

CROSS REFERENCE TO RELATED APPLICATIONS

This application is a divisional of U.S. application Ser. No. 13/810,587, filed May 31, 2013, claiming benefit of PCT Application No. PCT/US2011/044267, filed on Jul. 15, 2011, which claims priority from U.S. Provisional Application No. 61/365,152, filed on Jul. 16, 2010, the contents of which are hereby incorporated by reference in their entirety.

The present invention was made with funding from National Institutes of Health Grant No. HL019278. The United States Government has certain rights in this invention.

FIELD OF THE INVENTION

The present invention relates to methods for screening compounds and compositions useful for inhibiting or reducing platelet deposition, adhesion and/or aggregation. The present invention further relates to methods of treatment or prophylaxis of thrombotic disorders, including stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

BACKGROUND

Platelet accumulation at sites of vascular injury is a dynamic process that mediates formation of both the primary hemostatic plug and pathologic thrombus formation. The mechanisms by which platelet surface proteins direct platelet recruitment to thrombi under flow conditions have been studied in detail. In addition to directing initial platelet adhesion, cell-surface receptor interactions activate intracellular signaling. Intracellular signaling stimulates the release of thrombogenic substances from platelet granules. Signaling also mediates activation of the platelet integrin αIIbβ3 that facilitates firm adhesion of the platelets at the sites of injury.

Arterial thrombosis mediates tissue infarction in coronary artery disease, cerebrovascular disease, and peripheral vascular disease, and, thus, is the single most common cause of morbidity and mortality in the United States. Platelets are key mediators of arterial thrombosis. Thus, the identification of compounds that inhibit platelet function is of great importance to medicine.

Platelets form the body's primary means of hemostasis and, as such, have developed an elaborate mechanism of surveying the vasculature for defects in endothelial integrity. This mechanism involves the ability to respond to subendothelial matrices, shear forces, neighboring platelets, the adrenal axis, as well as soluble proteinacious, nucleotide, and lipid signals. Despite this plethora of physiologic activators, the platelet has only a small repertoire of major functional outputs. Upon activation, platelets change shape, aggregate, and secrete their granular contents. The process of platelet activation involves the expression of activities not shared by functionally intact resting platelets, including, for example, ATP release, serotonin release, lysosomal release, alpha granule release, dense granule release, and cell surface expression of markers of activated platelets [including, but not limited to P-selectin and activated αIIbβ3 (GPIIb/IIIa) receptor]. In addition, platelet activation results in the aggregation of platelets with each other and attachment to non-platelet surrounding cells. The granular contents of platelets supply additional adhesion molecules, growth factors, coagulation enzymes and other specialized molecules instrumental in the process of thrombus formation and the initiation of the healing process.

In addition to coronary artery disease/myocardial infarction, cerebrovascular disease and peripheral vascular disease, diseases and disorders associated with inappropriate platelet activity and arterial thrombosis also include, for example, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity can provide therapeutic and preventive benefits for each of these diseases or disorders. It is also possible that inappropriate platelet activation plays a role in venous thrombosis, such that platelet inhibitors can be useful for the treatment or prophylaxis of disorders associated with such thromboses.

A connection is emerging between platelet activation and inflammation, particularly allergic inflammation (e.g., in asthma) and inflammation at the sites of atherosclerotic damage. Therefore, compounds that inhibit platelet activation can also be useful in the treatment or prophylaxis of disorders involving inflammation.

There are a number of agents presently available that target platelet function. For example, aspirin is a relatively weak platelet inhibitor. However, aspirin can cause life-threatening allergic reactions in sensitive individuals.

Another platelet inhibiting agent is ticlopidine (Ticlid™, Roche Pharmaceuticals). Because it requires the production of active metabolites to be effective, the effect of ticlopidine is delayed 24-48 hours. The drug can also cause thrombotic thrombocytopenic purpura as well as life threatening leukopenia, nausea, abdominal pain, dyspepsia, diarrhea and skin rash.

Clopidogrel (Plavix™, Bristol-Meyers Squibb/Sanofi Pharmaceuticals) is another platelet inhibitor that requires the generation of active metabolites for its therapeutic efficacy. Therefore, clopidogrel also has a delay of at least several hours for its effect. Clopidogrel can also cause thrombotic thrombocytopenia purpura. The drug has also been associated with a number of side effects, including rash, edema, hypertension, hypercholesterolemia, nausea, abdominal pain, dyspepsia, diarrhea, urinary tract infections, liver enzyme elevations and arthralgia.

Recently, prasugrel was approved as a $P2Y_{12}$ inhibitor for use as a platelet inhibitor, but similar to clopidogrel, major bleeding, including non-fatal as well as fatal bleeding was observed.

The platelet inhibitory agent abciximab (c7E3 Fab, Reopro®, manufacturer-Centocor B. V., distributor-Eli Lilly and Co.) is only available in a parenteral form. The drug can cause severe thrombocytopenia. Its antiplatelet effects last for several days unless platelet transfusions are given and, therefore, may complicate surgery that is sometimes required in the setting of life-threatening arterial occlusion (e.g., emergent cardiac surgery in the setting of a myocardial infarction).

There is only limited clinical experience with the oral anti-αIIbβ3 agents lamifiban, sibrafiban, orbofiban and xemilofiban, none of which are approved for human use. Similarly, clinical experience is limited with the phosphodiesterase inhibitors cilostazol, trapidil and trifusal. There is more clinical experience with the phosphodiesterase inhibitor dipyridamole, but its activity is relatively weak and so it is not frequently used unless combined with aspirin.

There is a need in the art for additional platelet adhesion and aggregation inhibitory agents for the treatment and prophylaxis of diseases or disorders associated with abnormalities in platelet adhesion and aggregation.

It is known that integrin αIIbβ3 is a receptor on the surface of human platelets. As a heterodimeric complex composed of both αIIb and β3 subunits, the dimer is responsible for binding adhesive plasma proteins, most notably fibrinogen and von Willebrand factor (vWF). The binding of fibrinogen, vWF and other ligands by αIIbβ3 is mediated principally though the peptide recognition sequence Arg-Gly-Asp (RGD) or the fibrinogen y chain dodecapeptide HHLGGAKQAGDV (SEQ ID NO. 1). Conformational changes in αIIbβ3 are thought to occur upon the binding of ligand to the receptor, leading to the exposure of ligand-induced binding sites (LIBS) as detected by LIBS-specific monoclonal antibodies (mAbs). Electron microscopy and crystal structures of the integrin in complex with various R(K)GD-like ligands support the theory that the integrin undergoes a major conformational change after or during ligand binding.

Currently two small molecule inhibitors of the αIIbβ3 exist: a cyclic homoarginine-glycine-aspartic acid peptide (eptifibatide) and an RGD peptidomimetic (tirofiban). Both inhibitors act by competitively blocking the binding site for fibrinogen. Although both compounds have demonstrated significant clinical benefit, tirofiban (Aggrastat™, Merck and Co., Inc.) is only available in a parenteral form and can cause thrombocytopenia, dizziness and vasovagal reactions. Eptifibatide (Integrilin™, COR Therapeutics, Inc., Key Pharmaceuticals Inc.) is also only available for parenteral administration and it too can cause thrombocytopenia and hypotension. Crystal structure studies of the αIIbβ3 headpiece demonstrates that these inhibitors bind to both αIIb and to the divalent cation in the β3 subunit's metal ion dependant adhesion site (MIDAS). It is believed that the interaction with the MIDAS metal ion induces conformational changes in the β3 which leads to the increased the risk for thrombotic complications following αIIbβ3 inhibitor therapy.

SUMMARY OF THE INVENTION

Previously, our scientists have identified inhibitors of αIIbβ3, particularly 2-ethyl-7-(piperazin-1-yl)-5H-[1,3,4]thiadiazolo[3,2-a]pyrimidin-5-one, that are capable of inhibiting fibrinogen binding and platelet aggregation without inducing the binding of one or more integrin β3 LIBS-specific monoclonal antibodies (mAbs). These inhibitors are disclosed in U.S. patent application Ser. No. 12/514,286 (equivalent to U.S. Pub. No. 2010/0150913), the contents of which are hereby incorporated by reference in their entirety. Our scientists have now identified further inhibitors of αIIbβ3 that are capable of inhibiting fibrinogen binding and platelet aggregation without inducing the binding of integrin β3 LIBS. The present invention thus provides αIIbβ3 antagonists, pharmaceutical compositions comprising αIIbβ3 antagonists, new methods of treatment and prophylaxis using αIIbβ3 antagonists, and new methods to screen for αIIbβ3 antagonists that are capable of inhibiting fibrinogen binding without inducing β3 LIBS binding.

In the first aspect, the invention provides a compound of Formula P-I:

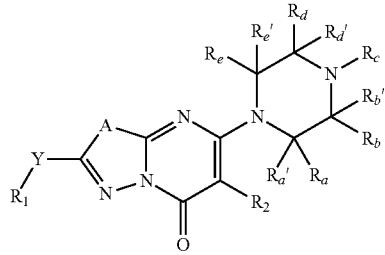

Formula P-I wherein:
i) A is S, N(H), $CH_2$, or O;
ii) $R_1$ is
phenyl optionally substituted with one or more nitro, —C(O)N($R_5$)($R_6$) and/or —N($R_5$)($R_6$) and Y is a —$C_1$-$C_4$alkylene (e.g., methylene) or arylene (e.g., phenylene);
phenyl substituted with one or more nitro and/or —N($R_5$)($R_6$) and Y is a single bond;
phenyl substituted with —C(O)O$R_3$ and Y is a —$C_1$-$C_4$alkylene (e.g., methylene) or arylene (e.g., phenylene);
heteroaryl (e.g., pyridyl, pyrazolyl, isoxazolyl, furyl, thienyl) wherein said heteroaryl group is optionally substituted with one or more —$C_1$-$C_4$alkyl (e.g., methyl) and Y is a single bond, —$C_1$-$C_4$alkylene (e.g., methylene);
heteroaryl (e.g., pyridyl, pyrazolyl, thienyl or pyrimidyl) wherein said heteroaryl group is substituted with halo (e.g., fluoro), —C(O)OH, —$CH_2$C(O)OH, or —$NH_2$, and Y is arylene (e.g., phenylene), for example $R_1$ is (pyrazol-1-yl)-4-acetic acid (i.e., -(pyrazol-1-yl)-4-$CH_2$C(O)OH), thiophen-4-yl-2-carboxylic acid (i.e., -(thiophen-4-yl)-2-C(O)OH), 2-fluoropyrid-4-yl or 2-amino-pyrimid-5-yl, and Y is phenylene;
pyrazolyl, isoxazolyl, furyl or thienyl and Y is arylene (e.g., phenylene) wherein said pyrazolyl, isoxazolyl, furyl or thienyl is optionally substituted with one or more —$C_1$-$C_4$alkyl (e.g., methyl), —$C_{0-4}$alkyl-C(O)OH, —N($R_{13}$)($R_{14}$), or halo (e.g., fluoro); or —C(O)N($R_4$)($CH_2$)$_{1-4}$—C(O)O$R_3$ (e.g., —C(O)N(H)$CH_2$C(O)OH) and Y is a single bond, —$C_1$-$C_4$alkylene (e.g., methylene) or arylene (e.g., phenylene),
—C(O)N($R_4$)($CH_2$)$_{1-4}$—N($R_{13}$)($R_{14}$) (e.g., —C(O)N(H)$CH_2CH_2NH_2$) and Y is a single bond, —$C_1$-$C_4$alkylene (e.g., methylene) or arylene (e.g., phenylene),
—N($R_4$)—C(O)-heteroaryl (e.g., —N($R_4$)—C(O)-pyridyl) wherein said heteroaryl is optionally substituted with halo (e.g., fluoro) and Y is a single bond, —$C_1$-$C_4$alkylene (e.g., methylene) or arylene (e.g., phenylene),
—N($R_4$)—$C_{1-4}$alkylene-heteroaryl (e.g., —N($R_4$)—$C_{1-4}$alkylene-pyridyl) and Y is a single bond, —$C_1$-$C_4$alkylene (e.g., methylene) or arylene (e.g., phenylene),
—N($R_{10}$)—C(O)—[C($R_{11}$)($R_{12}$)]$_{1-4}$—N($R_{13}$)($R_{14}$), e.g., —N($R_{10}$)—C(O)—[C($R_{11}$)($R_{12}$)]$_2$—N($R_{13}$)($R_{14}$) or —N($R_{10}$)—C(O)—C($R_{11}$)($R_{12}$)—N($R_{13}$)

($R_{14}$), and Y is a single bond, —$C_1$-$C_4$alkylene (e.g., methylene) or arylene (e.g., phenylene), for example, $R_1$ is —N(H)—C(O)—CH$_2$CH$_2$—NH$_2$ or —N(H)—C(O)—CH$_2$—NH$_2$ and Y is phenylene,
—N($R_{10}$)—C(O)—$C_{3-10}$heterocycloalkyl (e.g., —N($R_{10}$)—C(O)-piperidine) and Y is a single bond, —$C_1$-$C_4$alkylene (e.g., methylene) or arylene (e.g., phenylene);
—N($R_4$)(CH$_2$)$_{1-4}$—C(O)O$R_4$ (e.g., —N(H)CH$_2$C(O)OH) and Y is a single bond, —$C_1$-$C_4$alkylene (e.g., methylene) or arylene (e.g., phenylene);
—N($R_4$)C(O)C(H)(NH$_2$)CH$_2$CH$_2$—C(O)O$R_3$ and Y is arylene (e.g., phenylene);
—N($R_4$)C(O)C(H)(NH$_2$)CH$_2$-heteroaryl (e.g., —N($R_4$)C(O)C(H)(NH$_2$)CH$_2$-thiazol-4-yl and Y is arylene (e.g., phenylene);
—N($R_4$)C(O)C(H)(CH$_3$)—NH$_2$ and Y is arylene (e.g., phenylene);
—N($R_4$)C(O)CH$_2$CH$_2$C(H)(NH$_2$)—COOH and Y is arylene (e.g., phenylene);
—N($R_4$)C(O)—C(H)(NH$_2$)CH$_2$CH$_2$—COOH and Y is arylene (e.g., phenylene); or
—N($R_4$)C(O)-heteroaryl (—N(H)C(O)isoxazolyl) and Y is arylene (e.g., phenylene);
iii) $R_2$ is H, halo (e.g., fluoro) or —$C_1$-$C_4$alkyl (e.g., methyl);
iv) $R_a$, $R_a'$, $R_b$, $R_b'$, $R_c$, $R_d$, $R_d'$, $R_e$, and $R_e'$ are independently H or $C_1$-$C_4$alkyl (e.g., methyl or ethyl);
v) $R_3$, $R_4$, $R_5$ and $R_6$ are independently H or $C_1$-$C_4$alkyl;
vi) $R_{10}$, $R_{11}$, $R_{12}$, $R_{13}$ and $R_{14}$ are independently H or $C_{1-4}$alkyl (e.g., methyl), in free or salt form.

In a further embodiment of the first aspect, the invention provides a compound of Formula P-I, wherein said compound is a compound of Formula Q-I:

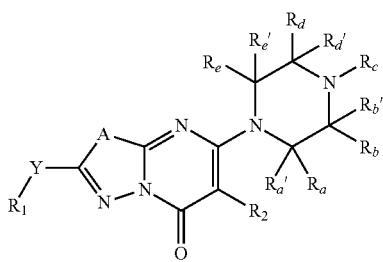

Formula Q-I wherein:
i) A is S, N(H), CH$_2$, or O;
ii) $R_1$ is
phenyl optionally substituted with one or more nitro and/or —N($R_5$)($R_6$) and Y is a —$C_1$-$C_4$alkylene (e.g., methylene) or arylene (e.g., phenylene);
phenyl substituted with one or more nitro and/or —N($R_5$)($R_6$) and Y is a single bond;
phenyl substituted with —C(O)O$R_3$ and Y is a —$C_1$-$C_4$alkylene (e.g., methylene) or arylene (e.g., phenylene);
heteroaryl (e.g., pyridyl, pyrazolyl, isoxazolyl, furyl, thienyl) wherein said heteroaryl group is optionally substituted with one or more —$C_1$-$C_4$alkyl (e.g., methyl) and Y is a single bond, —$C_1$-$C_4$alkylene (e.g., methylene);
pyrazolyl, isoxazolyl, furyl or thienyl and Y is arylene (e.g., phenylene) wherein said pyrazolyl, isoxazolyl, furyl or thienyl is optionally substituted with one or more —$C_1$-$C_4$alkyl (e.g., methyl), —$C_{0-4}$alkyl-C(O)OH, —N($R_{13}$)($R_{14}$), or halo (e.g., fluoro); or
—C(O)N($R_4$)(CH$_2$)$_{1-4}$—C(O)O$R_3$ (e.g., —C(O)N(H)CH$_2$C(O)OH) and Y is a single bond, —$C_1$-$C_4$alkylene (e.g., methylene) or arylene (e.g., phenylene),
—C(O)N($R_4$)(CH$_2$)$_{1-4}$—N($R_{13}$)($R_{14}$) (e.g., —C(O)N(H)CH$_2$CH$_2$NH$_2$) and Y is a single bond, —$C_1$-$C_4$alkylene (e.g., methylene) or arylene (e.g., phenylene),
—N($R_4$)—C(O)-heteroaryl (e.g., —N($R_4$)—C(O)-pyridyl) wherein said heteroaryl is optionally substituted with halo (e.g., fluoro) and Y is a single bond, —$C_1$-$C_4$alkylene (e.g., methylene) or arylene (e.g., phenylene),
—N($R_4$)—$C_{1-4}$alkylene-heteroaryl (e.g., —N($R_4$)—$C_{1-4}$alkylene-pyridyl) and Y is a single bond, —$C_1$-$C_4$alkylene (e.g., methylene) or arylene (e.g., phenylene),
—N($R_{10}$)—C(O)—C($R_{11}$)($R_{12}$)—N($R_{13}$)($R_{14}$) and Y is a single bond, —$C_1$-$C_4$alkylene (e.g., methylene) or arylene (e.g., phenylene),
—N($R_{10}$)—C(O)—$C_{3-10}$heterocycloalkyl (e.g., —N($R_{10}$)—C(O)-piperidine) and Y is a single bond, —$C_1$-$C_4$alkylene (e.g., methylene) or arylene (e.g., phenylene);
—N($R_4$)(CH$_2$)$_{1-4}$—C(O)O$R_4$ (e.g., —N(H)CH$_2$C(O)OH) and Y is a single bond, —$C_1$-$C_4$alkylene (e.g., methylene) or arylene (e.g., phenylene);
—N($R_4$)C(O)C(H)(NH$_2$)CH$_2$CH$_2$—C(O)O$R_3$ and Y is arylene (e.g., phenylene);
—N($R_4$)C(O)C(H)(NH$_2$)CH$_2$-heteroaryl (e.g., —N($R_4$)C(O)C(H)(NH$_2$)CH$_2$-thiazol-4-yl and Y is arylene (e.g., phenylene);
—N($R_4$)C(O)C(H)(CH$_3$)—NH$_2$ and Y is arylene (e.g., phenylene);
—N($R_4$)C(O)CH$_2$CH$_2$C(H)(NH$_2$)—COOH and Y is arylene (e.g., phenylene);
—N($R_4$)C(O)—C(H)(NH$_2$)CH$_2$CH$_2$—COOH and Y is arylene (e.g., phenylene);
—N($R_4$)C(O)-heteroaryl (—N(H)C(O)isoxazolyl) and Y is arylene (e.g., phenylene);
iii) $R_2$ is H, halo (e.g., fluoro) or —$C_1$-$C_4$alkyl (e.g., methyl);
iv) $R_a$, $R_a'$, $R_b$, $R_b'$, $R_c$, $R_d$, $R_d'$, $R_e$, and $R_e'$ are independently H or $C_1$-$C_4$alkyl (e.g., methyl or ethyl);
v) $R_3$, $R_4$, $R_5$ and $R_6$ are independently H or $C_1$-$C_4$alkyl;
vi) $R_{10}$, $R_{11}$, $R_{12}$, $R_{13}$ and $R_{14}$ are independently H or $C_{1-4}$alkyl (e.g., methyl), in free or salt form.

The invention further provides a compound of Formula P-I, as follows:
2.1. the compound of Formula P-I, wherein
$R_1$ is
phenyl optionally substituted with one or more nitro, —C(O)N($R_5$)($R_6$) and/or —N($R_5$)($R_6$) and Y is a —$C_1$-$C_4$alkylene (e.g., methylene) or arylene (e.g., phenylene);
phenyl substituted with one or more nitro and/or —N($R_5$)($R_6$) and Y is a single bond;
phenyl substituted with —C(O)O$R_3$ and Y is a —$C_1$-$C_4$alkylene (e.g., methylene) or arylene (e.g., phenylene);
heteroaryl (e.g., pyridyl, pyrazolyl, isoxazolyl, furyl, thienyl) wherein said heteroaryl group is optionally substituted with one or more —$C_1$-$C_4$alkyl (e.g., methyl) and Y is a single bond, —$C_1$-$C_4$alkylene (e.g., methylene);

heteroaryl (e.g., pyridyl, pyrazolyl, thienyl or pyrimidyl) wherein said heteroaryl group is substituted with halo (e.g., fluoro), —C(O)OH, —CH$_2$C(O)OH, or —NH$_2$, and Y is arylene (e.g., phenylene), for example R$_1$ is (pyrazol-1-yl)-4-acetic acid (i.e., -(pyrazol-1-yl)$_{1-4}$-CH$_2$C(O)OH), thiophen-4-yl-2-carboxylic acid (i.e., -(thiophen-4-yl)-2-C(O)OH), 2-fluoropyrid-4-yl or 2-amino-pyrimid-5-yl, and Y is phenylene;

pyrazolyl, isoxazolyl, furyl or thienyl and Y is arylene (e.g., phenylene) wherein said pyrazolyl, isoxazolyl, furyl or thienyl is optionally substituted with one or more —C$_1$-C$_4$alkyl (e.g., methyl), —C$_{0-4}$alkyl-C(O)OH, —N(R$_{13}$)(R$_{14}$), or halo (e.g., fluoro);

—C(O)N(R$_4$)(CH$_2$)$_{1-4}$—C(O)OR$_3$ (e.g., —C(O)N(H)CH$_2$C(O)OH) and Y is a single bond, —C$_1$-C$_4$alkylene (e.g., methylene) or arylene (e.g., phenylene), —C(O)N(R$_4$)(CH$_2$)$_{1-4}$—N(R$_{13}$)(R$_{14}$) (e.g., —C(O)N(H)CH$_2$CH$_2$NH$_2$) and Y is a single bond, —C$_1$-C$_4$alkylene (e.g., methylene) or arylene (e.g., phenylene), —N(R$_4$)—C(O)-heteroaryl (e.g., —N(R$_4$)—C(O)-pyridyl) wherein said heteroaryl is optionally substituted with halo (e.g., fluoro) and Y is a single bond, —C$_1$-C$_4$alkylene (e.g., methylene) or arylene (e.g., phenylene), —N(R$_4$)—C$_{1-4}$alkylene-heteroaryl (e.g., —N(R$_4$)—C$_{1-4}$alkylene-pyridyl) and Y is a single bond, —C$_1$-C$_4$alkylene (e.g., methylene) or arylene (e.g., phenylene), —N(R$_{10}$)—C(O)—[C(R$_{11}$)(R$_{12}$)]$_{1-4}$—N(R$_{13}$)(R$_{14}$), e.g., —N(R$_{10}$)—C(O)—C(R$_{11}$)(R$_{12}$)—N(R$_{13}$)(R$_{14}$), and Y is a single bond, —C$_1$-C$_4$alkylene (e.g., methylene) or arylene (e.g., phenylene), for example, R$_1$ is —N(H)—C(O)—CH$_2$CH$_2$—NH$_2$ and Y is phenylene, —N(R$_{10}$)—C(O)—C$_{3-10}$heterocycloalkyl (e.g., —N(R$_{10}$)—C(O)-piperidine) and Y is a single bond, —C$_1$-C$_4$alkylene (e.g., methylene) or arylene (e.g., phenylene);

—N(R$_4$)(CH$_2$)$_{1-4}$—C(O)OR$_4$ (e.g., —N(H)CH$_2$C(O)OH) and Y is a single bond, —C$_1$-C$_4$alkylene (e.g., methylene) or arylene (e.g., phenylene);

—N(R$_4$)C(O)C(H)(NH$_2$)CH$_2$—C(O)OR$_3$ and Y is arylene (e.g., phenylene);

—N(R$_4$)C(O)C(H)(NH$_2$)CH$_2$-heteroaryl (e.g., —N(R$_4$)C(O)C(H)(NH$_2$)CH$_2$-thiazol-4-yl and Y is arylene (e.g., phenylene);

—N(R$_4$)C(O)C(H)(CH$_3$)—NH$_2$ and Y is arylene (e.g., phenylene);

—N(R$_4$)C(O)CH$_2$CH$_2$C(H)(NH$_2$)—COOH and Y is arylene (e.g., phenylene);

—N(R$_4$)C(O)—C(H)(NH$_2$)CH$_2$CH$_2$—COOH and Y is arylene (e.g., phenylene);

—N(R$_4$)C(O)-heteroaryl (—N(H)C(O)isoxazolyl) and Y is arylene (e.g., phenylene);

R$_2$ is H, halo (e.g., fluoro) or —C$_1$-C$_4$alkyl (e.g., methyl);

R$_a$, R$_a$', R$_b$, R$_b$', R$_c$, R$_d$, R$_d$', R$_e$, and R$_e$' are independently H or C$_1$-C$_4$alkyl (e.g., methyl or ethyl);

R$_3$, R$_4$, R$_5$ and R$_6$ are independently H or C$_1$-C$_4$alkyl;

R$_{10}$, R$_{11}$, R$_{12}$, R$_{13}$ and R$_{14}$ are independently H or C$_{1-4}$alkyl (e.g., methyl), 2.2. the compound of Formula P-I, or 2.1, wherein R$_1$ is phenyl optionally substituted with one or more nitro, —C(O)N(R$_5$)(R$_6$) and/or —N(R$_5$)(R$_6$) and Y is a —C$_1$-C$_4$alkylene (e.g., methylene) or arylene (e.g., phenylene);

2.3. the compound of Formula P-I, or 2.1 or 2.2, wherein R$_1$ is phenyl optionally substituted with one or more nitro and/or —N(R$_5$)(R$_6$) and Y is a —C$_1$-C$_4$alkylene (e.g., methylene) or arylene (e.g., phenylene);

2.4. the compound of Formula P-I, or 2.1 or 2.2, wherein R$_1$ is phenyl optionally substituted with —C(O)N(R$_5$)(R$_6$) and Y is a —C$_1$-C$_4$alkylene (e.g., methylene) or arylene (e.g., phenylene);

2.5. the compound of Formula P-I, or 2.1, wherein R$_1$ is heteroaryl (e.g., pyridyl, pyrazolyl, thienyl or pyrimidyl) wherein said heteroaryl group is substituted with halo (e.g., fluoro), —C(O)OH, —CH$_2$C(O)OH, or —NH$_2$, and Y is arylene (e.g., phenylene), for example R$_1$ is (pyrazol-1-yl)-4-acetic acid (i.e., -(pyrazol-1-yl)-4-CH$_2$C(O)OH), thiophen-4-yl-2-carboxylic acid (i.e., -(thiophen-4-yl)-2-C(O)OH), 2-fluoropyrid-4-yl or 2-amino-pyrimid-5-yl, and Y is phenylene;

2.6. the compound of Formula P-I, 2.1 or 2.5, wherein R$_1$ is pyridyl substituted with halo (e.g., fluoro) and Y is arylene (e.g., phenylene), for example R$_1$ is 2-fluoropyrid-4-yl and Y is phenylene;

2.7. the compound of Formula P-I, 2.1 or 2.5, wherein R$_1$ is pyrimidyl substituted with —NH$_2$, and Y is arylene (e.g., phenylene), for example R$_1$ is 2-amino-pyrimid-5-yl, and Y is phenylene;

2.8. the compound of Formula P-I, or 2.1, wherein R$_1$ is —N(R$_{10}$)—C(O)—[C(R$_{11}$)(R$_{12}$)]$_{1-4}$—N(R$_{13}$)(R$_{14}$), e.g., —N(R$_{10}$)—C(O)—[C(R$_{11}$)(R$_{12}$)]$_2$—N(R$_{13}$)(R$_{14}$) or —N(R$_{10}$)—C(O)—C(R$_{11}$)(R$_{12}$)—N(R$_{13}$)(R$_{14}$), and Y is a single bond, —C$_1$-C$_4$alkylene (e.g., methylene) or arylene (e.g., phenylene), for example, R$_1$ is —N(H)—C(O)—CH$_2$CH$_2$—NH$_2$ or —N(H)—C(O)—CH$_2$—NH$_2$ and Y is phenylene;

2.9. the compound of Formula P-I, or 2.8, wherein R$_1$ is —N(R$_{10}$)—C(O)—[C(R$_{11}$)(R$_{12}$)]$_2$—N(R$_{13}$)(R$_{14}$) or —N(R$_{10}$)—C(O)—C(R$_{11}$)(R$_{12}$)—N(R$_{13}$)(R$_{14}$), and Y is arylene (e.g., phenylene);

2.10. the compound of Formula P-I, or 2.9, wherein R$_1$ is —N(H)—C(O)—CH$_2$CH$_2$—NH$_2$;

2.11. the compound of Formula P-I, or 2.9, wherein R$_1$ is —N(H)—C(O)—CH$_2$—NH$_2$;

2.12. the compound of Formula P-I, or any of formulae 2.1-2.11, wherein any of the substituents Y, R$_1$-R$_{14}$, R$_a$, R$_a$', R$_b$, R$_b$', R$_c$, R$_d$, R$_d$', R$_e$, and R$_e$', are independently defined in any of formulae 3.1-3.51, or the remaining substituents (i.e., substituents not yet defined in any of the above formulae) are as defined in any of formulae 3.1-3.51;

2.13. the compound of Formula P-I, or any of formulae 2.1-2.12, wherein said compound is selected from any of those disclosed in any of formulae 3.45-13.50, and the following:

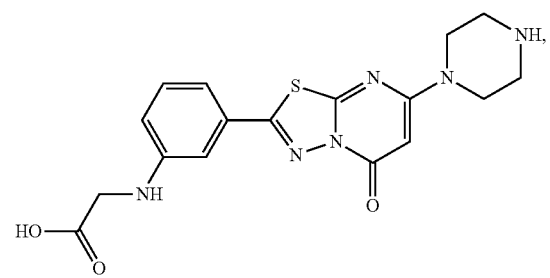

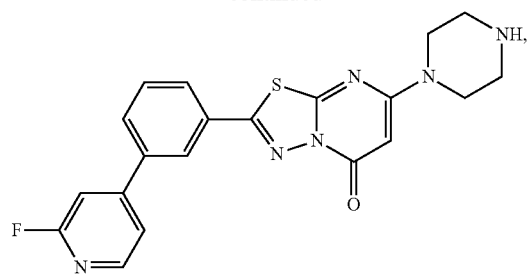
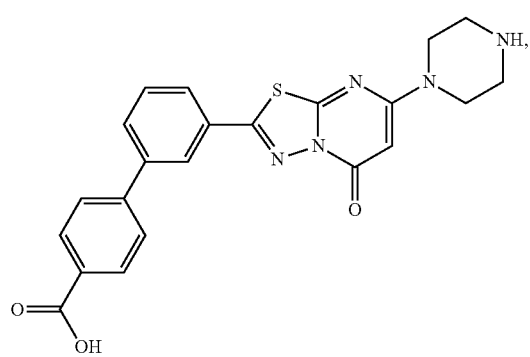
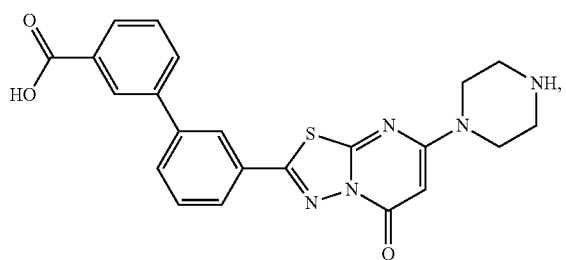
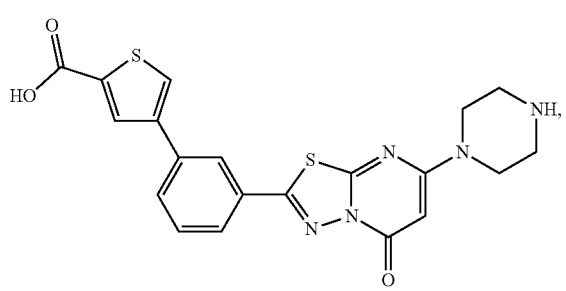
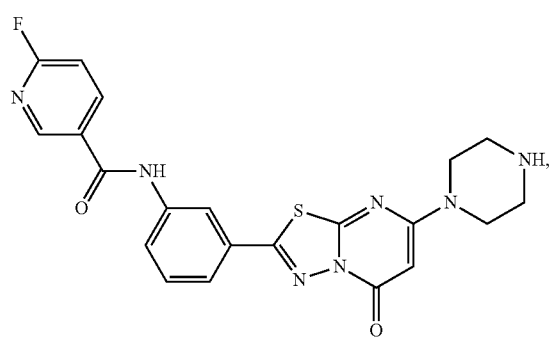
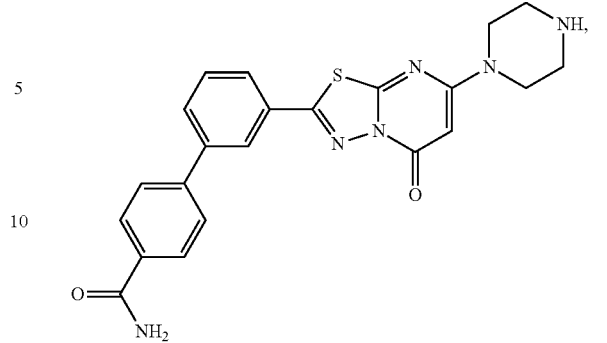
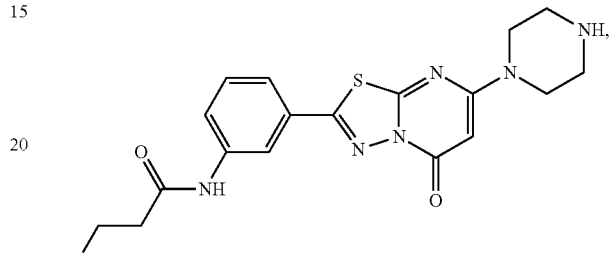
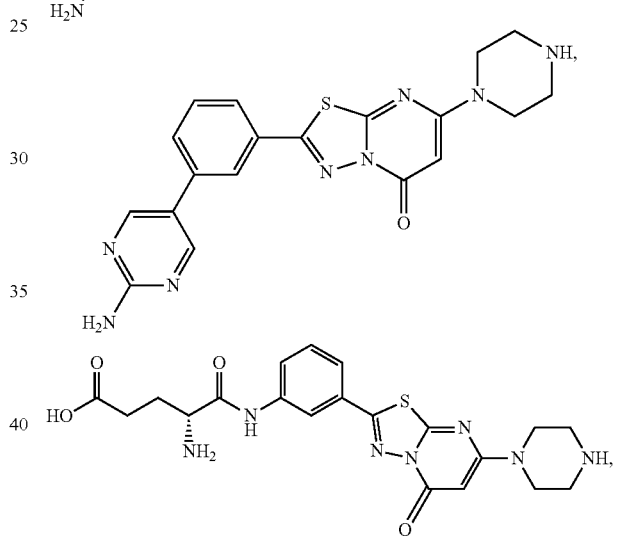
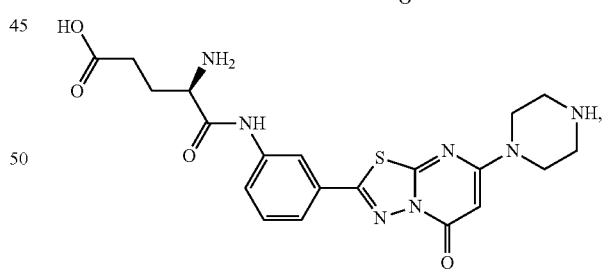
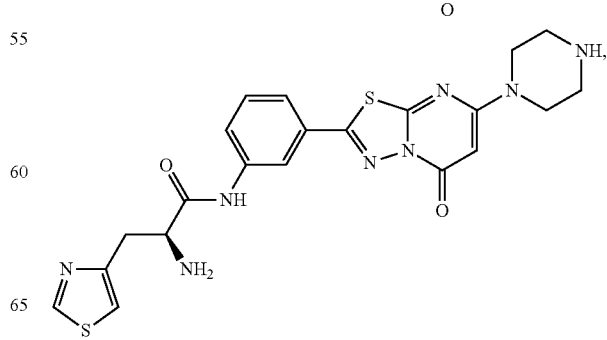

-continued in free or salt form.

The invention further provides a compound of Formula Q-I as follows:

3.1 a Compounds of Formula Q-I, wherein A is S, N(H), $CH_2$, or O;
3.2 a Compound of Formula Q-I or 3.1, wherein A is O;
3.3 a Compound of Formula Q-I or 3.1, wherein A is S;
3.4 a Compound of Formula Q-I, or any of 3.1-3.3, wherein $R_1$ is phenyl optionally substituted with one or more nitro and/or —$N(R_5)(R_6)$ and Y is a —$C_1$-$C_4$alkylene (e.g., methylene) or arylene (e.g., phenylene);
3.5 a Compound of Formula Q-I or any of 3.1-3.4, wherein $R_1$ is phenyl substituted with one or more nitro and/or —$N(R_5)(R_6)$ and Y is a single bond;
3.6 a Compound of Formula Q-I, or any of 3.1-3.4 wherein $R_1$ is phenyl substituted with —$C(O)OR_3$ and Y is a —$C_1$-$C_4$alkylene (e.g., methylene) or arylene (e.g., phenylene);
3.7 a Compound of Formula Q-I or any of 3.1-3.4, wherein $R_1$ is heteroaryl (e.g., pyridyl, pyrazolyl, isoxazolyl, furyl, thienyl) wherein said heteroaryl group is optionally substituted with one or more —$C_1$-$C_4$alkyl (e.g., methyl) and Y is a single bond or —$C_1$-$C_4$alkylene (e.g., methylene);
3.8 a Compound of Formula Q-I or any of 3.1-3.4, wherein $R_1$ is pyrazolyl, isoxazolyl, furyl or thienyl and Y is arylene (e.g., phenylene) wherein pyrazolyl, isoxazolyl, furyl or thienyl is optionally substituted with one or more —$C_1$-$C_4$alkyl (e.g., methyl) or halo (e.g., fluoro);
3.9 a Compound of Formula Q-I or 3.8, wherein $R_1$ is pyrazolyl and Y is arylene (e.g., phenylene) wherein said pyrazolyl is optionally substituted with one or more —$C_1$-$C_4$alkyl (e.g., methyl) or halo (e.g., fluoro);
3.10 a Compound of Formula Q-I or 3.8 or 3.9, wherein $R_1$ is pyrazolyl and Y is phenylene wherein said pyrazolyl is optionally substituted with one or more —$C_1$-$C_4$alkyl (e.g., methyl) or halo (e.g., fluoro);
3.11 formula 3.10, wherein said pyrazolyl is substituted on the meta-position of the phenylene (e.g., relative to the point of attachment);
3.12 a Compound of Formula Q-I or any of 3.1-3.4, wherein $R_1$ is —$C(O)N(R_4)(CH_2)_{1-4}$—$C(O)OR_3$ (e.g., —$C(O)N(H)CH_2C(O)OH$), —$C(O)N(R_4)(CH_2)_{1-4}$—$N(R_{13})(R_{14})$ (e.g., —$C(O)N(H)CH_2CH_2NH_2$), —$N(R_4)$—$C(O)$-heteroaryl (e.g., —$N(R_4)$—$C(O)$-pyridyl), —$N(R_4)$—$C_{1-4}$alkylene-heteroaryl (e.g., —$N(R_4)$—$C_{1-4}$alkylene-pyridyl), —$N(R_{10})$—$C(O)$—$C(R_{11})(R_{12})$—$N(R_{13})(R_{14})$, —$N(R_{10})$—$C(O)$—$C_{3-10}$heterocycloalkyl (e.g., —$N(R_{10})$—$C(O)$-piperidine) or —$N(R_4)(CH_2)_{1-4}$—$C(O)OR_4$ (e.g., —$N(H)CH_2C(O)OH$) and Y is a single bond, —$C_1$-$C_4$alkylene (e.g., methylene) or arylene (e.g., phenylene);
3.13 a Compound of Formula Q-I or 3.12, wherein Y is an arylene (e.g., phenylene);
3.14 a Compound of Formula Q-I or any of 3.1-3.4, wherein:
$R_1$ is—
  phenyl optionally substituted with one or more nitro and/or —$N(R_5)(R_6)$,
  phenyl substituted with —$C(O)OR_3$,
  pyrazolyl, isoxazolyl, furyl or thienyl wherein said pyrazolyl, isoxazolyl, furyl or thienyl is optionally substituted with one or more —$C_1$-$C_4$alkyl (e.g., methyl), —$C_{0-4}$alkyl-$C(O)OH$, —$N(R_{13})(R_{14})$, or halo (e.g., fluoro),
  —$C(O)N(R_4)(CH_2)_{1-4}$—$C(O)OR_3$ (e.g., —$C(O)N(H)CH_2C(O)OH$),
  —$C(O)N(R_4)(CH_2)_{1-4}$—$N(R_{13})(R_{14})$ (e.g., —$C(O)N(H)CH_2CH_2NH_2$),
  —$N(R_4)$—$C(O)$-heteroaryl (e.g., —$N(R_4)$—$C(O)$-pyridyl) wherein said heteroaryl is optionally substituted with halo (e.g., fluoro),
  —$N(R_4)$—$C_{1-4}$alkylene-heteroaryl (e.g., —$N(R_4)$—$C_{1-4}$alkylene-pyridyl), —$N(R_{10})$—$C(O)$—$C(R_{11})(R_{12})$—$N(R_{13})(R_{14})$,
  —$N(R_{10})$—$C(O)$—$C_{3-10}$heterocycloalkyl (e.g., —$N(R_{10})$—$C(O)$-piperidine),
  —$N(R_4)(CH_2)_{1-4}$—$C(O)OR_4$ (e.g., —$N(H)CH_2C(O)OH$);
  —$N(R_4)C(O)C(H)(NH_2)CH_2CH_2$—$C(O)OR_3$;
  —$N(R_4)C(O)C(H)(NH_2)CH_2$-heteroaryl (e.g., —$N(R_4)C(O)C(H)(NH_2)CH_2$-thiazol-4-yl and Y is arylene (e.g., phenylene);
  —$N(R_4)C(O)C(H)(CH_3)$—$NH_2$;
  —$N(R_4)C(O)CH_2CH_2C(H)(NH_2)$—$COOH$,
  —$N(R_4)C(O)$—$C(H)(NH_2)CH_2CH_2$—$COOH$ or,
  —$N(R_4)C(O)$-heteroaryl (—$N(H)C(O)$isoxazolyl), and Y is arylene (e.g., phenylene);

3.15 a Compound of Formula Q-I or 3.12, 3.13 or 3.14, wherein Y is a phenylene;
3.16 formula 3.15, wherein $R_1$ is substituted on the meta-position of the phenylene (e.g., relative to the point of attachment);
3.17 a Compound of Formula Q-I or any of 3.12-3.16, wherein $R_1$ is —N($R_{10}$)—C(O)—C($R_{11}$)($R_{12}$)—N($R_{13}$)($R_{14}$);
3.18 a Compound of Formula Q-I or any of 3.12-3.16, wherein $R_1$ is —N($R_{10}$)—C(O)—$C_{3-10}$heterocycloalkyl (e.g., —N($R_{10}$)—C(O)-piperidine);
3.19 a Compound of Formula Q-I or any of 3.12-3.18, wherein $R_4$, is H or $C_{1-4}$alkyl (e.g., methyl);
3.20 a Compound of Formula Q-I or any of 3.12-3.18, wherein $R_{10}$ is H;
3.21 a Compound of Formula Q-I or any of 3.12-3.18, wherein $R_{10}$ is $C_{1-4}$alkyl (e.g., methyl);
3.22 a Compound of Formula Q-I or any of 3.12-3.17 or 3.19-3.21, wherein $R_{11}$, $R_{12}$, $R_{13}$ and $R_{14}$ are independently H or $C_{1-4}$alkyl (e.g., methyl);
3.23 a Compound of Formula Q-I or any of 3.12-3.17 or 3.19-3.21, wherein $R_{11}$ and $R_{12}$ are both H;
3.24 a Compound of Formula Q-I or any of 3.12-3.17 or 3.19-3.21, wherein $R_{11}$ is H and $R_{12}$ is $C_{1-4}$alkyl (e.g., methyl);
3.25 a Compound of Formula Q-I or any of 3.12-3.17 or 3.19-3.21, wherein $R_{13}$ and $R_{14}$ are independently H or $C_{1-4}$alkyl (e.g., methyl);
3.26 a Compound of Formula Q-I or any of 3.12-3.17 or 3.19-3.21, wherein $R_{13}$ and $R_{14}$ are both H;
3.27 a Compound of Formula Q-I or any of 3.12-3.17 or 3.19-3.21, wherein $R_{13}$ is H and $R_{14}$ is $C_{1-4}$alkyl (e.g., methyl);
3.28 a Compound of Formula Q-I or any of 3.1-3.27, wherein $R_2$ is H, halo (e.g., fluoro) or $C_1$-$C_4$alkyl (e.g., methyl);
3.29 a Compound of Formula Q-I or any of 3.1-3.28, wherein $R_2$ is —$C_1$-$C_4$alkyl (e.g., methyl);
3.30 a Compound of Formula Q-I or any of 3.1-3.27, wherein $R_2$ is H or halo (e.g., fluoro);
3.31 a Compound of Formula Q-I or any of 3.1-3.27, wherein $R_2$ is H;
3.32 a Compound of Formula Q-I or any of 3.1-3.27, wherein $R_2$ is halo (e.g., fluoro);
3.33 a Compound of Formula Q-I or any of 3.1-3.32, wherein $R_a$, $R_a$', $R_b$, $R_b$', $R_c$, $R_d$, $R_d$', $R_e$, and $R_e$' are independently H or $C_1$-$C_4$alkyl (e.g., methyl or ethyl);
3.34 a Compound of Formula Q-I or any of 3.1-3.32, wherein $R_a$', $R_b$', $R_d$' and $R_e$' are H;
3.35 a Compound of Formula Q-I or any of 3.1-3.34, wherein $R_a$, $R_b$, $R_c$, $R_d$ and $R_e$ are independently H or $C_1$-$C_4$alkyl (e.g., methyl or ethyl);
3.36 a Compound of Formula Q-I or any of 3.1-3.34, wherein $R_a$, $R_b$, $R_c$, $R_d$ and $R_e$ are independently H;
3.37 a Compound of Formula Q-I or any of 3.1-3.34, wherein $R_a$, $R_b$, $R_c$, $R_d$ and $R_e$ are independently $C_1$-$C_4$alkyl (e.g., methyl or ethyl);
3.38 a Compound of Formula Q-I or any of 3.1-3.37, wherein $R_3$, $R_4$, $R_5$ and $R_6$ are independently H or $C_1$-$C_4$alkyl;
3.39 a Compound of Formula Q-I or any of 3.1-3.37, wherein $R_3$, $R_4$, $R_5$ and $R_6$ are independently H;
3.40 a Compound of Formula Q-I or any of 3.1-3.37, wherein $R_3$, $R_4$, $R_5$ and $R_6$ are independently $C_1$-$C_4$alkyl;
3.41 a Compound of Formula Q-I or any of 3.1-3.40, wherein the compound is

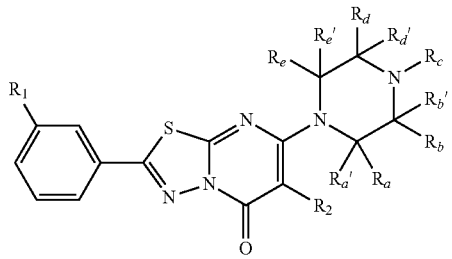

wherein
$R_1$ is:
  phenyl optionally substituted with one or more nitro and/or —N($R_5$)($R_6$);
  phenyl substituted with —C(O)O$R_3$;
  pyrazolyl optionally substituted with one or more —$C_1$-$C_4$alkyl (e.g., methyl) or halo (e.g., fluoro);
  —C(O)N($R_4$)(CH$_2$)$_{1-4}$—C(O)O$R_3$ (e.g., —C(O)N(H)CH$_2$C(O)OH);
  —C(O)N($R_4$)(CH$_2$)$_{1-4}$—N($R_{13}$)($R_{14}$) (e.g., —C(O)N(H)CH$_2$CH$_2$NH$_2$);
  —N($R_4$)—C(O)-heteroaryl (e.g., —N($R_4$)—C(O)-pyridyl);
  —N($R_4$)—$C_{1-4}$alkylene-heteroaryl (e.g., —N($R_4$)—$C_{1-4}$alkylene-pyridyl);
  —N($R_{10}$)—C(O)—C($R_{11}$)($R_{12}$)—N($R_{13}$)($R_{14}$);
  —N($R_{10}$)—C(O)—$C_{3-10}$heterocycloalkyl (e.g., —N($R_{10}$)—C(O)-piperidine);
  —N($R_4$)(CH$_2$)$_{1-4}$—C(O)O$R_4$ (e.g., —N(H)CH$_2$C(O)OH);
  —N($R_4$)C(O)C(H)(NH$_2$)CH$_2$CH$_2$—C(O)O$R_3$;
  —N($R_4$)C(O)C(H)(NH$_2$)CH$_2$-heteroaryl (e.g., —N($R_4$)C(O)C(H)(NH$_2$)CH$_2$-thiazol-4-yl;
  —N($R_4$)C(O)C(H)(CH$_3$)—NH$_2$;
  —N($R_4$)C(O)CH$_2$CH$_2$C(H)(NH$_2$)—COOH;
  —N($R_4$)C(O)—C(H)(NH$_2$)CH$_2$CH$_2$—COOH;
  —N($R_4$)C(O)-heteroaryl (—N(H)C(O)isoxazolyl);
$R_2$ is H, halo (e.g., fluoro) or —$C_1$-$C_4$alkyl (e.g., methyl);
$R_3$, $R_4$, $R_5$ and $R_6$ are independently H or $C_1$-$C_4$alkyl;
$R_{10}$, $R_{11}$, $R_{12}$, $R_{13}$ and $R_{14}$ are independently H or $C_{1-4}$alkyl (e.g., methyl);
$R_a$, $R_a$', $R_b$, $R_b$', $R_c$, $R_d$, $R_d$', $R_e$, and $R_e$' are H;
3.42 a Compound of Formula Q-I or any of 3.1-3.40, wherein the compound is as shown below:

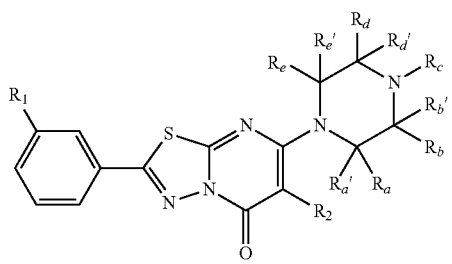

wherein
$R_1$ is:
  phenyl optionally substituted with one or more nitro and/or —N($R_5$)($R_6$); phenyl substituted with —C(O)O$R_3$;
  pyrazolyl optionally substituted with one or more —$C_1$-$C_4$alkyl (e.g., methyl) or halo (e.g., fluoro);

C(O)N(R$_4$)(CH$_2$)$_{1-4}$—C(O)OR$_3$ (e.g., —C(O)N(H)CH$_2$C(O)OH);

—N(R$_4$)—C(O)-heteroaryl (e.g., —N(R$_4$)—C(O)-pyridyl); —N(R$_4$)—C$_{1-4}$alkylene-heteroaryl (e.g., —N(R$_4$)—C$_{1-4}$alkylene-pyridyl);

—N(R$_4$)—C(O)—C(R$_{11}$)(R$_{12}$)—N(R$_{13}$)(R$_{14}$);

—N(R$_{10}$)—C(O)—C$_{3-10}$heterocycloalkyl (e.g., —N(R$_{10}$)—C(O)-piperidine); or —N(R$_4$)(CH$_2$)$_{1-4}$—C(O)OR$_4$ (e.g., —N(H)CH$_2$C(O)OH);

R$_2$ is H, halo (e.g., fluoro) or —C$_1$-C$_4$alkyl (e.g., methyl);

R$_3$, R$_4$, R$_5$ and R$_6$ are independently H or C$_1$-C$_4$alkyl;

R$_{10}$, R$_{11}$, R$_{12}$, R$_{13}$ and R$_{14}$ are independently H or C$_{1-4}$alkyl (e.g., methyl);

R$_a$, R$_a$', R$_b$, R$_b$', R$_c$, R$_d$, R$_d$', R$_e$, and R$_e$' are independently H or C$_1$-C$_4$alkyl (e.g., methyl or ethyl);

3.43 a Compound of Formula Q-I or any of 3.1-3.41, wherein the compound is as shown below:

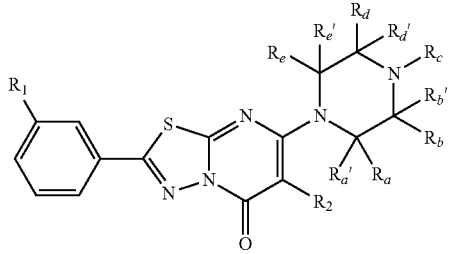

wherein

R$_1$ is —N(R$_{10}$)—C(O)—C(R$_{11}$)(R$_{12}$)—N(R$_{13}$)(R$_{14}$), e.g., —NHC(O)CH$_2$NH$_2$;

R$_2$ is H or halo (e.g., fluoro);

R$_a$, R$_a$', R$_b$, R$_b$', R$_c$, R$_d$, R$_d$', R$_e$, and R$_e$' are independently H or C$_1$-C$_4$alkyl (e.g., methyl or ethyl);

R$_{10}$, R$_{11}$, R$_{12}$, R$_{13}$ and R$_{14}$ are independently H or C$_{1-4}$alkyl (e.g., methyl);

3.44 any of the preceding formulae 3.1-3.43, wherein the Compound of Formula Q-I is selected from any of the following:

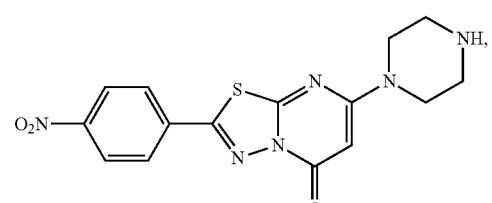

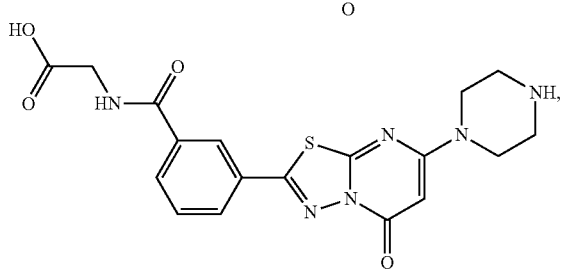

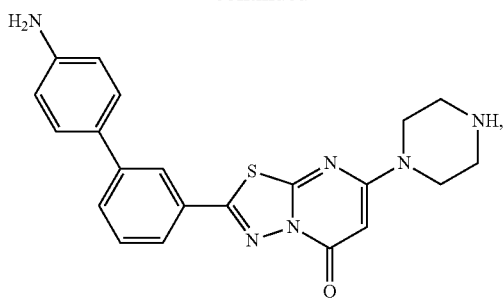

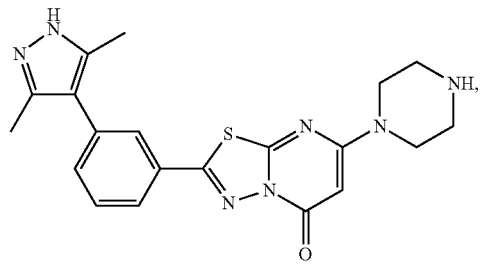

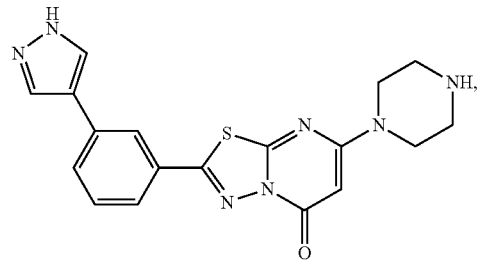

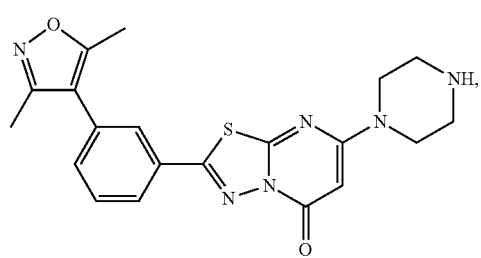

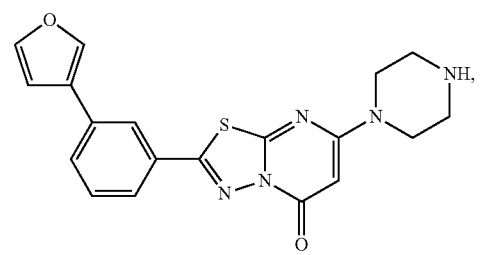

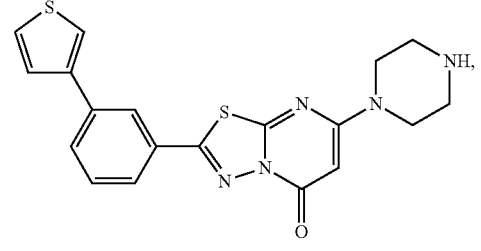

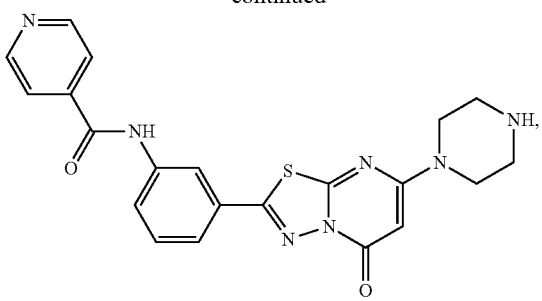
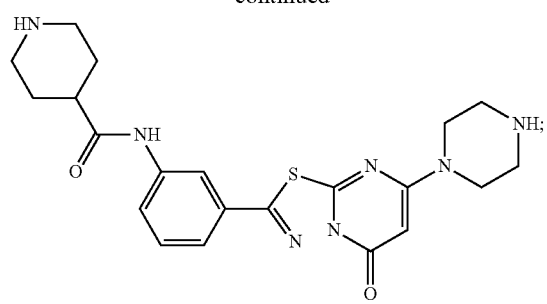
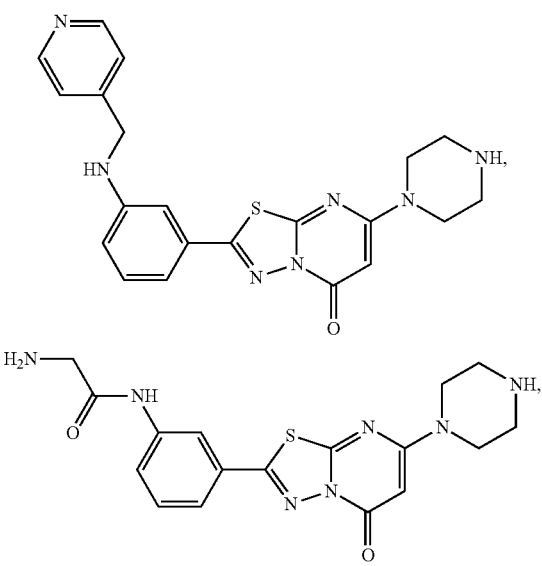
3.45 any of formulae 3.1-3.44, wherein the Compound of Formula Q-I is selected from any of the following:
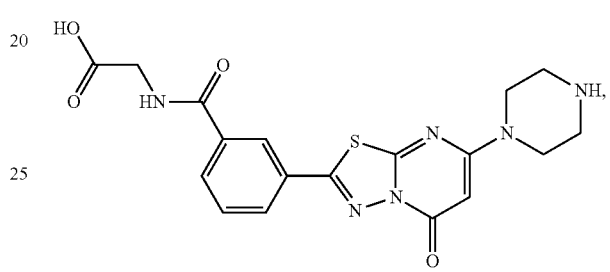
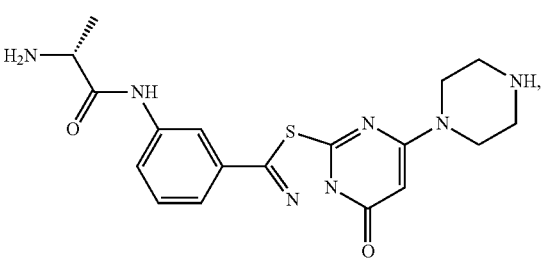
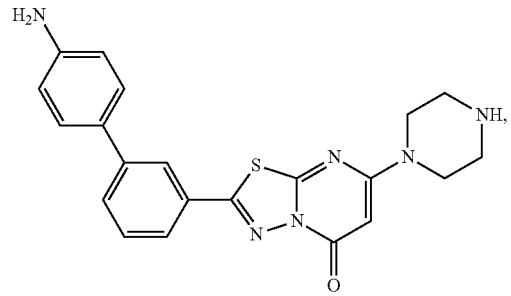
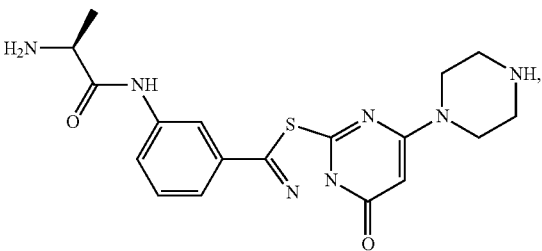
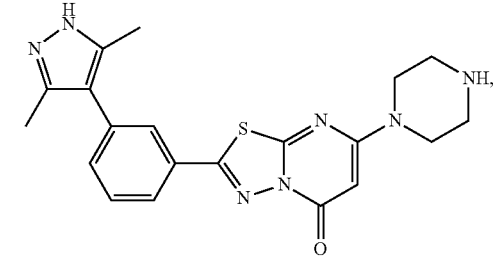
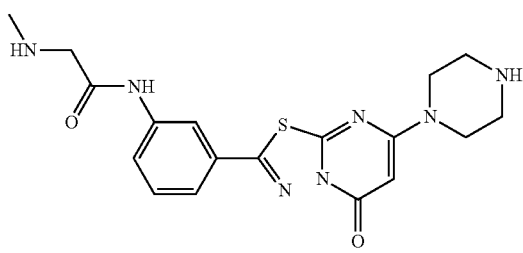
and

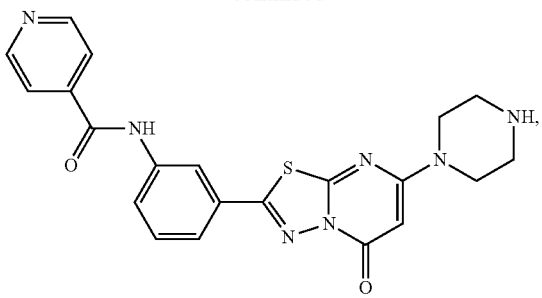
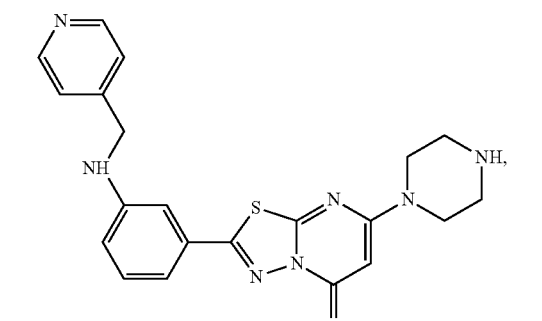
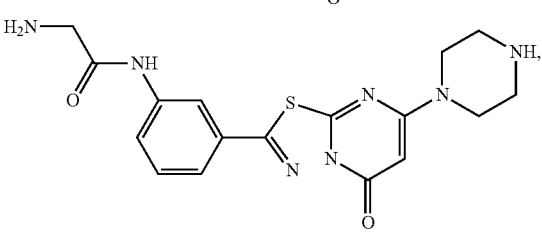
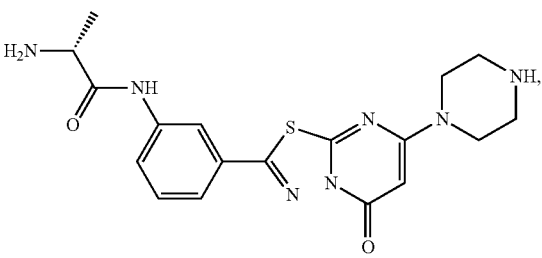
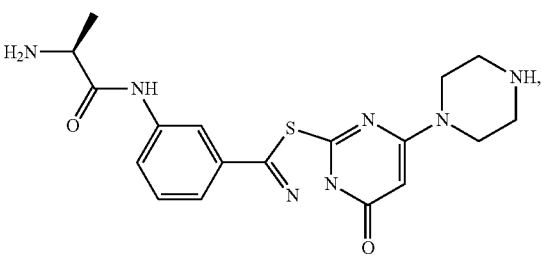
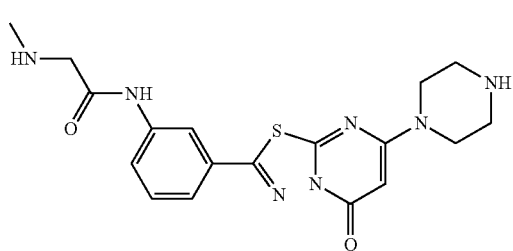
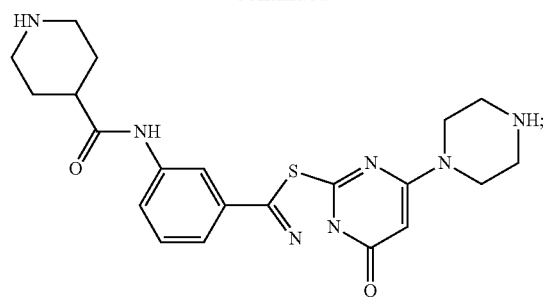
3.46 any of formulae 3.1-3.44 wherein the Compound of Formula Q-I is selected from any of the following:
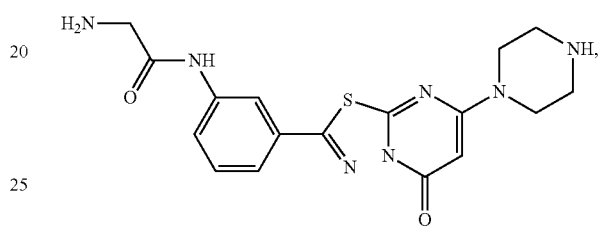
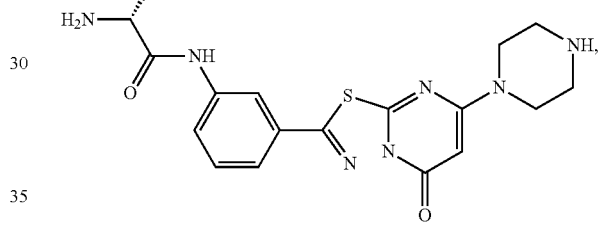
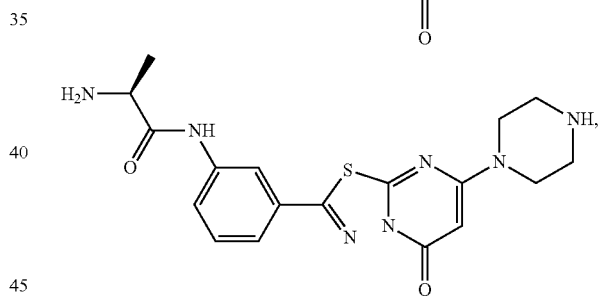
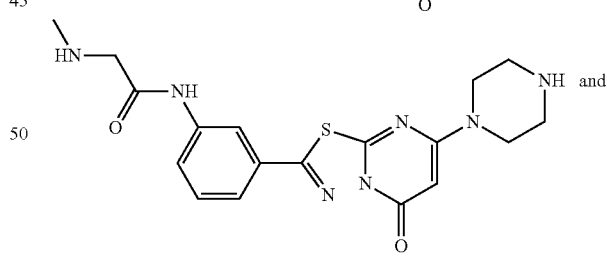

3.47 any of formulae 3.1-3.44 wherein the Compound of Formula Q-I is selected from any of the following:

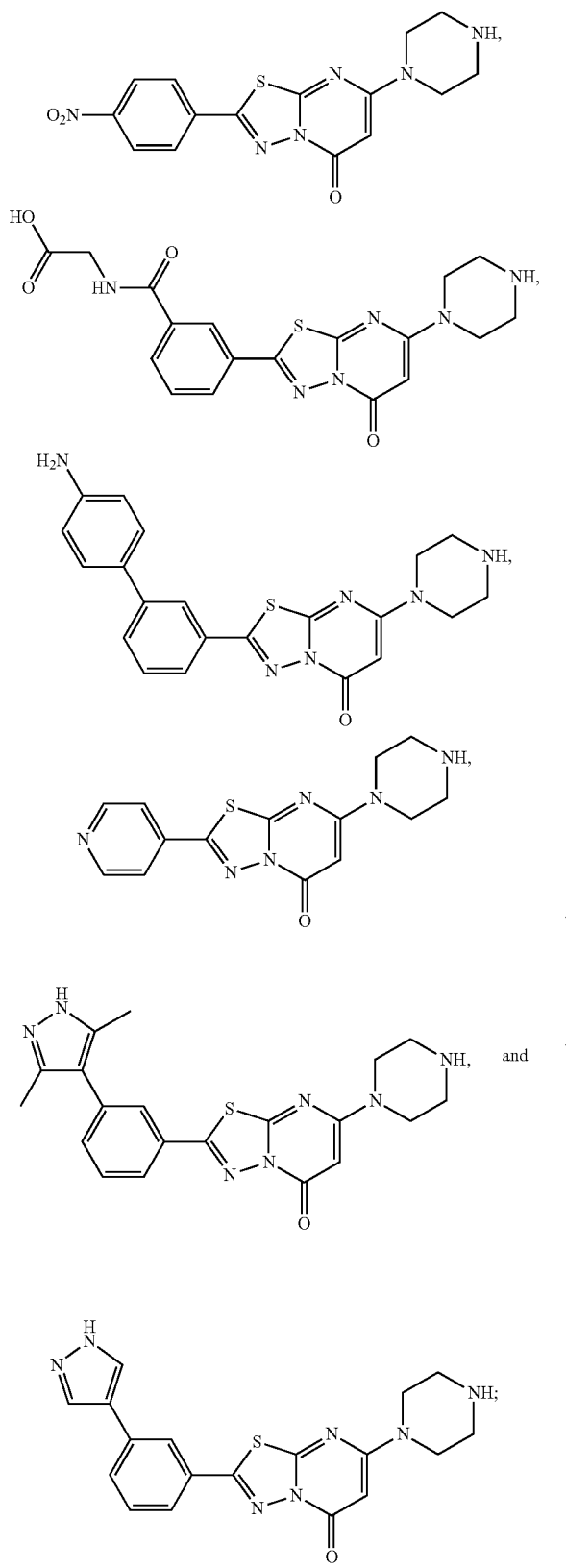

and 3.48 any of formulae 3.1-3.44 wherein the Compound of Formula Q-I is:

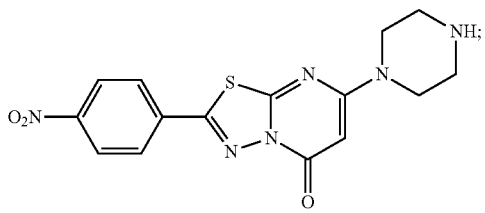 [SMILES: O=c1cc(N2CCNCC2)nc2sc(-c3ccc([N+](=O)[O-])cc3)nn12]

3.49 any of formulae 3.1-3.44 wherein the Compound of Formula Q-I is:

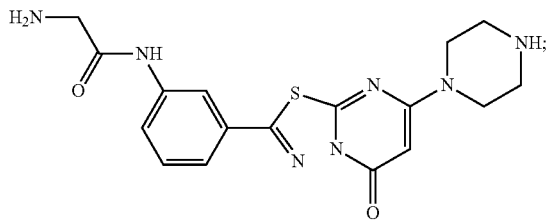 [SMILES: N=C(Sc1nc(N2CCNCC2)cc(=O)[nH]1)c1cccc(NC(=O)CN)c1]

3.50 any of formulae 3.1-3.44 wherein the Compound of Formula Q-I is:

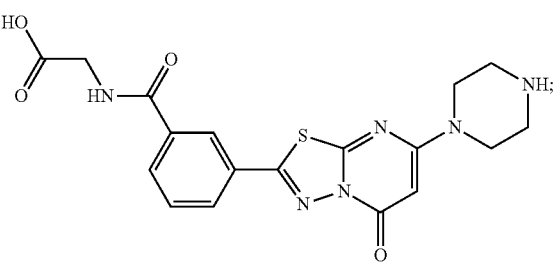 [SMILES: O=C(O)CNC(=O)c1cccc(-c2nn3c(=O)cc(N4CCNCC4)nc3s2)c1]

3.51 any of the preceding formulae wherein the compound of Formula Q-I has an $IC_{50}$ value of less than 100 μM, preferably less than 75 μM, more preferably less than 50 μM, most preferably, less than 25 μM in an aggregation assay as described in Example 44 and/or a percentage of inhibition of greater than 30%, preferably greater than 40%, more preferably, greater than 50%, more preferably, greater than 60%, most preferably greater than 70% at a concentration of 100 μM or less in an adhesion assay as described in Example 44.

in free or salt form.

In a further embodiment of the first aspect, the invention provides a Compound of Formula P-I or Q-I, preferably formula 3.43, wherein:

$R_1$ is —N($R_{10}$)—C(O)—C($R_{11}$)($R_{12}$)—N($R_{13}$)($R_{14}$), e.g., —NHC(O)CH$_2$NH$_2$;

$R_2$ is H;

$R_a$, $R_a'$, $R_b$, $R_b'$, $R_c$, $R_d$, $R_d'$, $R_e$ and $R_e'$ are independently H or $C_1$-$C_4$alkyl (e.g., methyl or ethyl);

$R_{10}$, $R_{11}$, $R_{12}$, $R_{13}$ and $R_{14}$ are independently H or $C_{1-4}$alkyl (e.g., methyl), in free or salt form.

In a further embodiment of the first aspect, the invention provides a Compound of Formula P-I or Q-I, preferably formula 3.43, wherein:

R₁ is —N(R₁₀)—C(O)—C(R₁₁)(R₁₂)—N(R₁₃)(R₁₄), e.g., —NHC(O)CH₂NH₂;

R₂ is H;

$R_a$, $R_a'$, $R_b$, $R_b'$, $R_c$, $R_d$, $R_d'$, $R_e$ and $R_e'$ are H;

R₁₀, R₁₁, R₁₂, R₁₃ and R₁₄ are independently H or C₁₋₄alkyl (e.g., methyl), in free or salt form.

In the second aspect, the Invention provides a Compound of Formula I-A selected from:

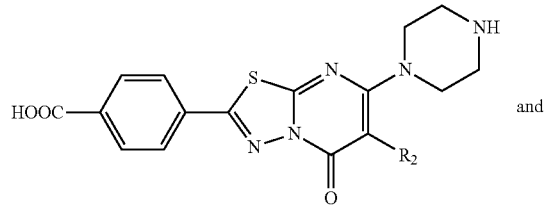

and

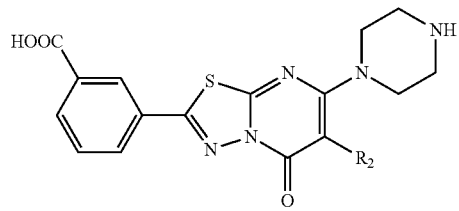

wherein R₂ is H, halo (e.g., fluoro) or C₁-C₄-alkyl (e.g., methyl), in free or salt form. In a particular embodiment, the Compound of Formula I-A is the compound having the para-substituted carboxylic acid and R₂ is H.

In the third aspect, the Invention provides a Compound of Formula I-B selected from:

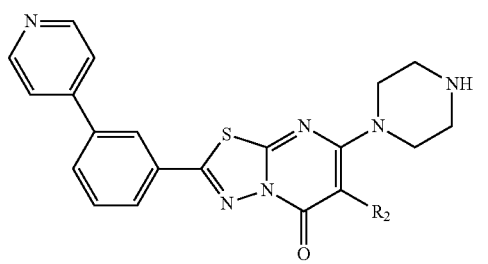

and

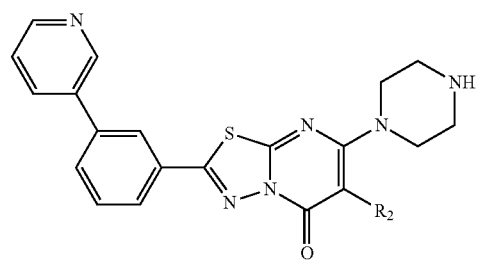

wherein R₂ is H, halo (e.g., fluoro) or C₁-C₄-alkyl (e.g., methyl), in free or salt form.

In the fourth aspect, the invention provides a Compound of Formula I-C selected from any one of the following:

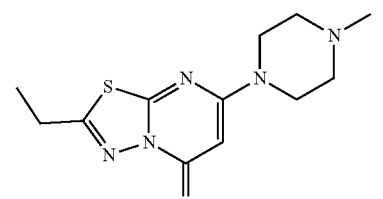

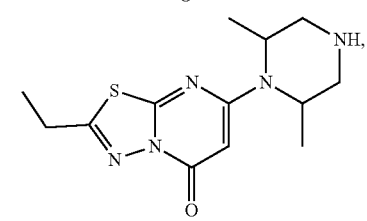

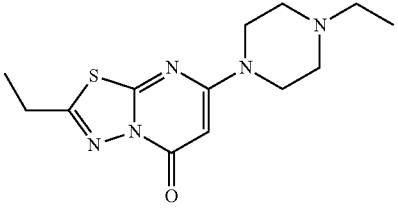

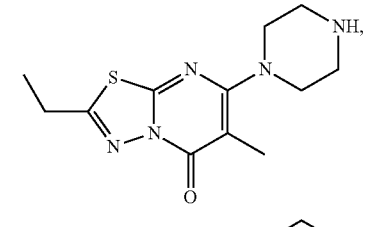

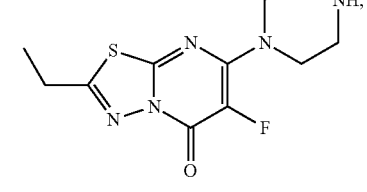

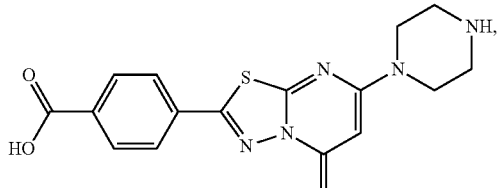

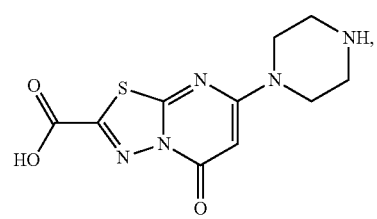

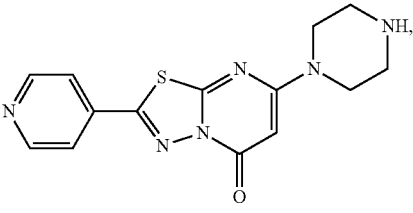

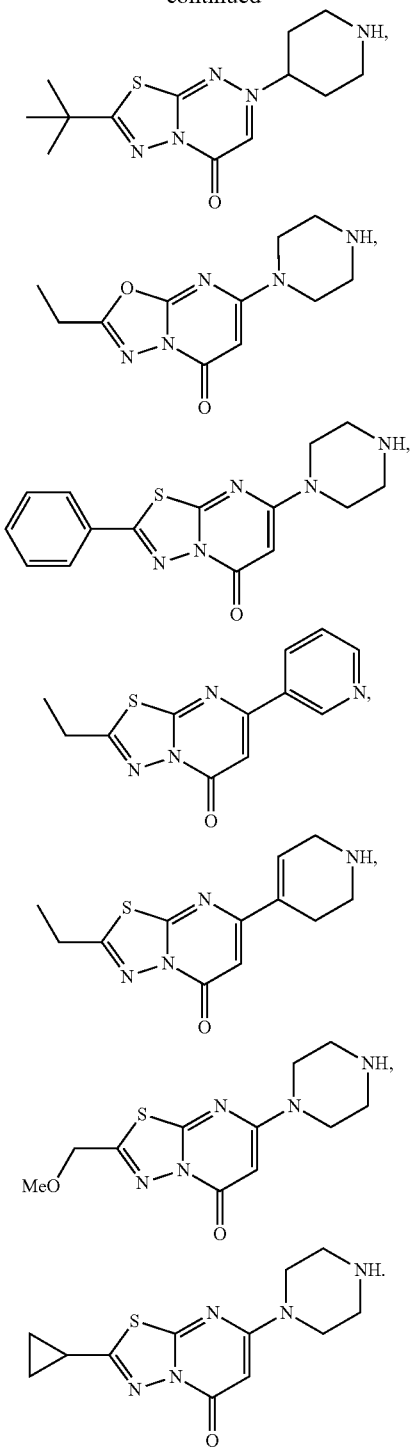

in free or salt form.

Preferably, the Compounds of the Present Invention (e.g., any of the compounds hereinbefore described, e.g. any of Compound of Formula P-I, any of 2.1-2.13, Formula Q-I, e.g., any of 3.1-3.51, or the compound described As 3.52 or 3.53, any of the Compound of Formula I-A, I-B or I-C, as hereinbefore described, in free or salt form) are selected from the Compounds of Formula Q-I, e.g., any of 3.1-3.51, more preferably, the compounds of formula 3.45, most preferably formula 3.49, in free or salt form.

In the fifth aspect, the invention provides to a Pharmaceutical Composition (Composition Q-I) comprising a Compound of the Invention hereinbefore described, e.g., a Compound of Formula P-I, any of 2.1-2.13, Formula Q-I, e.g., any of 3.1-3.51, or the compounds described as 3.52 and 3.53, any of the Compound of Formula I-A, I-B or I-C, preferably selected from the Compounds of Formula Q-I, e.g., any of 3.1-3.51, more preferably, the compounds of formula 3.45, most preferably 3.49, as hereinbefore described, in free or pharmaceutically acceptable salt form, in combination or association with a pharmaceutically acceptable diluent or carrier. Composition Q as hereinbefore described is useful, e.g., for preventing or inhibiting platelet adhesion and/or aggregation in treating thrombotic a disorder in a subject in need thereof. In a particular embodiment, the invention provides Composition Q-I as hereinbefore described, wherein the compound is a Compound of Formula Q-I, any of 3.1-3.51, or the compounds described as 3.52 and 3.53, more preferably, the compounds of formula 3.45, most preferably 3.49, in free or pharmaceutically acceptable salt form. In yet another embodiment, the invention provides a Pharmaceutical Composition Q-I as hereinbefore described useful for inhibiting or reducing platelet aggregation and/or adhesion.

In the sixth aspect, the invention provides a method for inhibiting or reducing platelet aggregation and/or adhesion comprising administering to a subject in need thereof, an effective amount of a Compound of Formula P-I, any of 2.1-2.13, Formula Q-I, e.g., any of 3.1-3.51, or the compounds described as 3.52 and 3.53, any of the Compound of Formula I-A, I-B or I-C, preferably a Compound of Formula Q-I, e.g., any of 3.1-3.51, or the compounds described as 3.52 and 3.53, more preferably, a compound of formula 3.45, most preferably 3.49, in free or pharmaceutically acceptable salt form, such that platelet aggregation and/or adhesion is reduced (Method Q-I).

The invention further provides for the following methods:
6.1 Method Q-I, wherein the compound is a Compound of Formula P-I, any of 2.1-2.13, Formula Q-I, e.g., any of 3.1-3.51, or the compounds described- as 3.52 and 3.53, more preferably, the compound of formula 3.45, most preferably 3.49, in free or pharmaceutically acceptable salt form;
6.2 Method Q-I or 6.1, wherein reduction of platelet aggregation and/or adhesion treats or inhibits a thrombotic disorder, e.g. selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

In a particular embodiment, the invention provides Method Q-I, e.g., formula 6.1 or 6.2, wherein both platelet aggregation and adhesion are reduced (Method Q-I').

In the seventh aspect, the invention provides a method for the treatment or prophylaxis of a thrombotic disorder comprising administering to a subject at risk of a thrombotic disorder, an effective amount of a compound of Formula P-I, any of 2.1-2.13, Formula Q-I, e.g., any of 3.1-3.51, or the compounds described as 3.52 and 3.53, any of the Compound of Formula I-A, I-B or I-C, as hereinbefore described, in free or pharmaceutically acceptable salt form, such that platelet aggregation and/or adhesion is reduced (Method Q-II).

The invention further provides for the following methods:
7.1 Method Q-II, wherein said thrombotic disorder is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation;

7.2 Method Q-II or 7.1, wherein said thrombotic disorder is thrombosis as a result of angioplasty or stent placement;

7.3 Method Q-II, 7.1 or 7.2, wherein subject at risk of thrombotic disorder is a subject who has a history of vascular surgery;

7.4 Method Q-II or any of Methods 7.1-7.3, further comprises administering to said subject an effective amount of at least one therapeutic agent selected from a group consisting of anti-coagulant, antiplatelet, and thrombolytic agents in conjunction with a Compound of Formula P-I, any of 2.1-2.13, Formula Q-I, e.g., any of 3.1-3.51, or the compounds described -as 3.52 and 3.53, any of the Compound of Formula I-A, I-B or I-C, as hereinbefore described, in free or pharmaceutically acceptable salt form;

7.5 Method Q-II, or any of Methods 7.1-7.4, further comprises administering to said subject an effective amount of at least one therapeutic agent selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, abciximab, eptifibatide and tirofiban in conjunction with a Compound of Formula P-I, any of 2.1-2.13, Formula Q-I, e.g., any of 3.1-3.51, or the compounds described- as 3.52 and 3.53, any of the Compound of Formula I-A, I-B or I-C, as hereinbefore described, in free or pharmaceutically acceptable salt form;

7.6 Method Q-II or any of Methods 7.1-7.4, further comprises administering to said subject an anticoagulant or thrombolytic agent in conjunction with a Compound of Formula P-I, any of 2.1-2.13, Formula Q-I, e.g., any of 3.1-3.51, or the compounds described- as 3.52 and 3.53, any of the Compound of Formula I-A, I-B or I-C, as hereinbefore described, in free or pharmaceutically acceptable salt form;

7.7 Method Q-II or any of Methods 7.1-7.4, further comprises administering to said subject an effective amount of heparin in conjunction with a Compound of Formula P-I, any of 2.1-2.13, Formula Q-I, e.g., any of 3.1-3.51, or the compounds described- as 3.52 and 3.53, any of the Compound of Formula I-A, I-B or I-C, as hereinbefore described, in free or pharmaceutically acceptable salt form.

7.8 Method Q-II or any of Methods 7.1-7.7, wherein the Compound of the Invention is a Compound of Formula P-I, any of 2.1-2.13, Formula Q-I, e.g., any of 3.1-3.51, or the compounds described- as 3.52 and 3.53, more preferably, the compounds of formula 3.45, most preferably formula 3.49, in free or pharmaceutically acceptable salt form.

The invention further provides any of the foregoing methods wherein the compounds of the present invention (a) reduce platelet inhibition with a percentage of inhibition of greater than 30%, preferably greater than 50% at a concentration of 100 µM or less; and/or (b) reduce platelet aggregation, e.g., with an $IC_{50}$ of less than 100 µM, preferably less than 25 µM in an ADP or other agonist-induced platelet aggregation assay and/or in a fibrinogen binding assay as described in the examples below.

In a preferred embodiment, the invention is a method for the treatment or prophylaxis of a thrombotic disorder comprising administering an effective amount of a Compound of Formula P-I, any of 2.1-2.13, Formula Q-I, any of 3.1-3.51, or the compounds described- as 3.52 and 3.53, more preferably, the compounds of formula 3.44, most preferably 3.49 in free or pharmaceutically acceptable salt form.

In a particular embodiment, the invention is a method for the treatment or prophylaxis of a thrombotic disorder comprising administering heparin in conjunction with the Compound of Formula P-I, any of 2.1-2.13, Formula Q-I, e.g., any of 3.1-3.51, or the compounds described- as 3.52 and 3.53, any of the Compound of Formula I-A, I-B or I-C, as hereinbefore described, in free or pharmaceutically acceptable salt form, preferably a Compound of Formula P-I, any of 2.1-2.13, Formula Q-I, any of 3.1-3.51, or the compounds described as 3.52 and 3.53, more preferably, the compounds of formula 3.44, most preferably 3.49 in free or pharmaceutically acceptable salt form.

Without being bound to any theory, it is believed that binding of ligand by the receptor induces conformational changes in αIIbβ3, exposing the ligand-induced binding sites (LIBS). With traditional αIIbβ3-inhibitors such as tirofiban and eptifibatide, binding of these compounds to both the αIIb and to the divalent cation in the β3 subunit's metal ion dependant adhesion site (MIDAS) inhibits platelet adhesion. It is believed, however, that the interaction with the β3 subunit's metal ion dependant adhesion site (MIDAS) is likely to be responsible for initiating the conformational change which result in both the thrombocytopenia and the increased mortality rate of traditional αIIbβ3 antagonists. The present invention identifies αIIbβ3 inhibitors that are capable of inhibiting fibrinogen binding without inducing the binding of one more integrin β3 LIBS-specific mAbs. Therefore, in one embodiment, the Compounds of the Invention e.g., the Compound of Formula P-I, any of 2.1-2.13, Formula Q-I, e.g., any of 3.1-3.51, or the compounds described as 3.52 and 3.53, any of the Compound of Formula I-A, I-B or I-C, preferably, the compounds of formula 3.45, most preferably formula 3.49, in free or salt form may bind to αIIb, and in some cases induce αIIb LIBS exposure, without inducing β3 LIBS exposure. Such compounds thus demonstrate specific binding to αIIbβ3 integrin and inhibition of platelet adhesion without the disadvantage of inducing the change in conformation of the β3 and consequent risk of complications following dissociation of the compounds from the αIIbβ3.

In the eighth aspect, the invention provides a drug-eluting stent wherein the drug or drugs eluted comprise a Platelet Inhibitor of the Invention, or a Compound of P-I, any of 2.1-2.13, Formula Q-I, e.g., any of 3.1-3.51, or the compounds described- as 3.52 and 3.53, any of the Compound of Formula I-A, I-B or I-C, preferably, the Compound of Formula Q-I, more preferably, the compounds of formula 3.45, most preferably formula 3.49, in free or pharmaceutically acceptable salt form as hereinbefore described. For example, the invention provides a stent, e.g., an arterial stent, for example a coronary artery or carotid artery stent, which comprises a biocompatible polymer matrix which comprises or is associated with a Compound of P-I, any of 2.1-2.13, Formula Q-I, e.g., any of 3.1-3.51, or the compounds described- as 3.52 and 3.53, any of the Compound of Formula I-A, I-B or I-C, in free or pharmaceutically acceptable salt form as hereinbefore described. The stent may be made of metal, plastic, biodegradable or bioabsorbable material or combination thereof, e.g., stainless steel, nickel-titanium alloy, colbalt-alloy, tantalum, silicone, polytetrafluoroethylene, magnesium alloy or poly-L-lactide. For example, a stent may be a metallic stent (e.g., stainless steel, nickel-titanium alloy, colbalt alloy, or tantalum) partially or wholly coated with a biocompatible polymer, e.g., a plastic (e.g., polytetrafluoroethylene) or a polymeric carrier (e.g., phosphorylcholine or polylactic acid) which polymer comprises or is associated with a Compound of P-I, any of 2.1-2.13, Formula Q-I, e.g., any of 3.1-3.51, or the compounds described- as 3.52 and 3.53, any of the Compound of Formula I-A, I-B or I-C, preferably, the compounds of formula Q-I, more preferably, formula 3.45, most preferably formula 3.49, in free or pharmaceutically acceptable salt form as hereinbefore described, e.g., such that said Compound is presented or released in a manner and amount effective to inhibit platelet adhesion and/or aggregation in the vicinity of the stent. The stent may further comprise or be associated with an additional drug or drugs, e.g., an antiproliferative agent, e.g., sirolimus, everolimus, zotarolimus, tacrolimus, or paclitaxel, and/or an anticoagulant, e.g., heparin.

In the ninth aspect, the invention provides a Compound of Formula P-I, any of 2.1-2.13, Formula Q-I, e.g., any of 3.1-3.51, or the compounds described- as 3.52 and 3.53, any of the Compound of Formula I-A, I-B or I-C, preferably, Compounds of Formula P-I, any of 2.1-2.13, Formula Q-I, e.g., any of 3.1-3.51, or the compounds described-, as 3.52 and 3.53, more preferably, the compounds of formula 3.45, most preferably formula 3.49, in free or pharmaceutically acceptable salt form as hereinbefore described, for use as a pharmaceutical, e.g. use of a Compound of Formula P-I, any of 2.1-2.13, Formula Q-I, e.g., any of 3.1-3.51, or the compounds described- as 3.52 and 3.53, any of the Compound of Formula I-A, I-B or I-C, preferably Compounds of Formula P-I, any of 2.1-2.13, Formula Q-I, e.g., any of 3.1-3.51, or the compounds described- as 3.52 and 3.53, more preferably, the compounds of formula 3.45, most preferably formula 3.49, in free or pharmaceutically acceptable salt form as hereinbefore described, e.g., (in the manufacture of a medicament) for the treatment or prophylaxis of a thrombotic disorder, e.g., according to any of Method Q-I, e.g., formula 6.1 or 6.2, or Method Q-II or any of methods 7.1-7.8.

In the tenth aspect, the invention provides a Pharmaceutical Composition comprising a Compound of Formula P-I, any of 2.1-2.13, Formula Q-I, e.g., any of 3.1-3.51, or the compounds described- as 3.52 and 3.53, any of the Compound of Formula I-A, I-B or I-C, preferably, Compounds of Formula P-I, any of 2.1-2.13, Formula Q-I, e.g., any of 3.1-3.51, or the compounds described- as 3.52 and 3.53, more preferably, the compounds of formula 3.45, most preferably formula 3.49, in free or pharmaceutically acceptable salt form as hereinbefore described, for use as a pharmaceutical e.g., (in the manufacture of a medicament) for the treatment or prophylaxis of a thrombotic disorder, e.g., according to any of Method Q-I, e.g., formula 6.1 or 6.2, or Method Q-II or any of methods 7.1-7.8.

DETAILED DESCRIPTION OF THE INVENTION

As used herein, the term "$\alpha IIb\beta 3$" or "integrin $\alpha IIb\beta 3$" refers to the receptor on the surface of human platelets. It is a heterodimeric complex composed of both $\alpha IIb$ and $\beta 3$ subunits responsible for binding adhesive plasma proteins, most notably fibrinogen and von Willebrand factor.

The term "antagonist" refers to any ligand or molecule that binds to receptors and competitively or noncompetitively blocks the binding of ligand to that receptor. Therefore, "$\alpha IIb\beta 3$ antagonist" refers to any ligand or molecule that competitively or noncompetitively blocks $\alpha IIb\beta 3$.

"LIBS" refers to ligand-induced binding sites on $\alpha IIb\beta 3$ that are presented or exposed upon the binding of a ligand or antagonist by the receptor.

"LIBS-specific mAbs" refers to monoclonal antibodies that bind to the exposed ligand-induced binding sites of $\alpha IIb\beta 3$. Examples of LIBS-specific mAbs include AP5, PMI-1 and LIBS1.

The term "thrombotic disorders" refers to disorders characterized by formation of a thrombus that obstructs vascular blood flow. Examples of thrombotic disorders include stroke, myocardial infarction, stable or unstable angina, peripheral vascular disease, abrupt closure following angioplasty or stent placement and thrombosis induced by vascular surgery. Thrombotic disorders also include disorders characterized by formation of a thrombus caused by atrial fibrillation or inflammation.

The phrase "subject at risk of thrombotic disorders" or "subject in need thereof" includes subjects who have a history of vascular intervention (e.g. angioplasty, stent placement, aortocoronary bypass or insertion of prosthetic heart valves), cardiovascular abnormality (e.g. atrial fibrillation) or a family history of vascular diseases (e.g., coronary artery disease (CAD), systemic hypertension, diabetes mellitus, hyperlipidemia, bicuspid aortic valve, hypertrophic cardiomyopathy or mitral valve prolapse). The term "subject" may include human or non-human (e.g., an animal).

The term "platelet adhesion" refers to the binding of platelet membrane proteins to fibrinogen, collagen, von' Willebrand factor (vWF) or other adhesive glycoproteins (e.g., fibronectin, laminin).

The term "platelet aggregation" refers to the attachment of activated platelets one to another, which results in the formation of aggregates or clumps of activated platelets.

The phrase "inhibit or reduce platelet adhesion and/or aggregation" is intended to mean at least a 30% inhibition of platelet activity at a concentration of 100 µM or lower in a given assay, relative to platelet activity in the absence of the compound.

The phrase "antagonist known to expose $\beta 3$ LIBS" herein refers to agents that induce conformational in $\beta 3$, for example tirofiban.

The term "anticoagulants" herein refers to any compound or substance that either stimulates natural inhibitor of coagulant proteases or blocks the coagulation cascade. Examples of anticoagulants include, but are not limited to heparin, warfarin, phenprocoumon, fondaparinux, lepirudin, bivalirudin, argatroban, danaparoid and drotrecogin alfa.

The term "anti-platelet agents" herein refers to compound or substance that prevents platelet adhesion and/or aggregation. Examples of anti-platelet agents include, but are not limited to prasugrel, aspirin, ticlopidine, clopidogrel, abciximab, eptifibatide and tirofiban.

The term "fibrinolytic agents" therefore refers to any compound or substance that lyses pathological thrombi. "Thrombolytic agents" are agents that are fibrinolytic, i.e., agents that convert plasminogen to plasmin, which lyses fibrin. Examples of fibrinolytic agents include but are not limited to streptokinase and tissue plasminogen activator (t-PA).

The term "stent" herein refers to expandable wire form or perforated tube that is inserted into a natural conduit of the body, such as an artery, usually a coronary artery, to prevent or counteract a disease-induced localized flow constriction.

The term "optionally substituted" is intended to mean substituted with the substituents defined or unsubstituted. For example, phenyl optionally substituted with one or more nitro means in some instances, the phenyl is substituted with one or more nitro groups and in other instances, the phenyl is unsubstituted.

The binding of LIBS-specific mAbs to αIIbβ3 may be measured by comparing the binding of LIBS-specific mAbs to αIIbβ3 in the presence of testing compound with the binding of LIBS-specific mAbs to αIIbβ3 in the absence or presence of a control such as untreated platelets and/or other known αIIbβ3 inhibitors that are known to cause β3 LIBS exposure, e.g., tirofiban. For example, the test compound may bind to αIIb and optionally increases binding of at least one αIIb LIBS-specific mAb relative to binding to unactivated platelets without increasing the binding of one or more β3 LIBS-specific mAbs relative to binding to unactivated platelets and/or produces less binding relative to binding in the presence of an agent known to bind to and directly activate αIIbβ3 so as to expose β3 LIBS.

As used herein, the term "alkyl" or "alkyl chain" or "alkylene" refers to a linear or branched, saturated or unsaturated, aliphatic hydrocarbon. Unless otherwise specified, alkyl refers to a hydrocarbon chain containing one to four carbon atoms. Examples of alkyl may include, but are not limited to methyl, ethyl, tert-butyl and the like as well as alkenyl or alkynyl substituents.

The term "$C_3$-$C_{10}$cycloalky" or "$C_{3-10}$cycloalky" refers to fully or partially saturated, carbocyclic, non-aromatic hydrocarbon radicals having three to eight carbon atoms. Examples of $C_3$-$C_{10}$cycloalkyl optionally containing one or more heteroatoms selected from a group consisting of O or N include, but are not limited to, cyclopropyl, cyclobutyl, cyclopentyl, cyclopentenyl, cyclohexyl or cyclohexenyl, piperidinyl, piperazinyl, morpholinyl, imidazolinyl, pyrrolidinyl. These cycloalkyl systems may be attached via the heteroatom or any other carbon on the system. $C_3$-$C_{10}$cycloalky may also refer to non-aromatic cyclic system fused to an aromatic cyclic system. An example of this includes tetrahydroquinolinyl.

The term "aryl" refers to any aromatic ring system. Aromatic compounds include phenyl, naphthyl and their derivatives.

The term "heteroaryl" is intended to mean a stable 5- to 6-membered monocyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to another ring.

The term "acyl" is intended to encompass R—C(O)— wherein R is $C_{1-4}$alkyl wherein said alkyl is optionally substituted with one or more halo, hydroxy, or $C_{1-4}$alkoxy.

The Compounds of the Invention may comprise one or more chiral carbon atoms. The compounds thus exist in individual isomeric, e.g., enantiomeric or diasteriomeric form or as mixtures of individual forms, e.g., racemic/ diastereomeric mixtures. Any isomer may be present in which the asymmetric center is in the (R)-, (S)-, or (R,S)- configuration. The invention is to be understood as embracing both individual optically active isomers as well as mixtures (e.g., racemic/diasteromeric mixtures) thereof. Accordingly, the Compound of the Invention may be a racemic mixture or it may be predominantly, e.g., in pure, or substantially pure, isomeric form, e.g., greater than 70% enantiomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like)

Compounds of the Invention may exist in free or salt form, e.g., as acid addition salts (e.g., hydrochloric acid, toluene sulfonic acid, methane sulfonic acid, benzene sulfonic acid, trifluoroacetic acid, and the like). In this specification unless otherwise indicated language such as Compounds of the Invention is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. In particular embodiment, the salt of the compound of the invention is a trifluoroacetic acid addition salt.

Compounds of the Invention may in some cases also exist in prodrug form. A prodrug form is compound which converts in the body to a Compound of the Invention. For example, when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. For example, wherein the compounds of the invention contains a hydroxy group (e.g., Drug-OH), the prodrug (e.g., Drug-O—C(O)—$CH_3$) may hydrolyze under physiological conditions to yield hydroxy (Drug-OH) on the one hand and acid, e.g., carboxylic acid on the other (e.g., $CH_3COOH$), which are themselves physiologically tolerable at doses to be administered. Similarly, wherein the compounds of the invention contains a carboxylic acid group (e.g., Drug-C(O)OH), its prodrug (e.g., Drug-C(O)—O—$CH_2CH_3$) may hydrolyze under physiological conditions to yield the carboxylic acid (Drug-C(O)OH) on the one hand and alcohol, e.g., ethanol on the other (e.g., $CH_3CH_2OH$), which are themselves physiologically tolerable at doses to be administered. As will be appreciated the term thus embraces conventional pharmaceutical prodrug forms.

Compounds of the present invention may be administered orally or parenterally, including intravenous, intramuscular, intraperitoneal, subcutaneous, transdermal, airway (aerosol), rectal, vaginal and topical (including buccal and sublingual) administration. The compounds useful in the invention may generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Dosages of the compounds of the invention will vary depending upon the condition to be treated or prevented and on the identity of the inhibitor being used. Estimates of effective dosages and in vivo half-lives for the individual compounds encompassed by the invention can be made on the basis of in vivo testing using an animal model, such as the mouse model described herein or an adaptation of such method to larger mammals. Appropriate dosage may range from 0.01 mg to 5000 mg. For example, one appropriate dosage may be 0.01-30 mg/Kg, e.g., 26.5 mg/Kg, e.g., 12 mg/Kg.

In addition to their administration singly, the compounds useful according to the invention can be administered in combination or in conjunction with other known therapeutic agents useful for thrombotic disorders such as anticoagulants (e.g., heparin, warfarin, phenprocoumon, fondaparinux, lepirudin, bivalirudin, argatroban, danaparoid, drotrecogin alfa), fibrinolytic agents (e.g., streptokinase or tissue plasminogen activator (t-PA) or other anti-platelet agents (e.g., prasugrel, aspirin, ticlopidine, clopidogrel, abciximab, eptifibatide and tirofiban). In any event, the administering physician can adjust the amount and timing of drug administration on the basis of results observed using standard measures of platelet activity known in the art or described herein.

EXAMPLES

Example 1

Synthesis of Compounds of the Present Invention

The compounds described herein and their pharmaceutically acceptable salts may be made using the methods as described and exemplified herein and by methods similar thereto and by methods known in the chemical art. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, reaction may require to be run at elevated temperature, for a longer or shorter period of time or in the presence of an acid or base. It is understood by one skilled in the art of organic synthesis that functionality present on various portions of the molecule must be compatible with the reagents and reactions proposed. If not commercially available, starting materials for these processes may be made by procedures, which are selected from the chemical art using techniques similar or analogous to the synthesis of known compounds. Significances of the substituents are as set forth in the formulae hereinbefore defined unless otherwise specified. All references cited herein are hereby incorporated in their entirety by reference.

All commercially available reagents and solvents are purchased and used without further purification. All microwave reactions are carried out in a sealed microwave vial equipped with a magnetic stir bar and heated in a Biotage Initiator Microwave Synthesizer. All compounds for biological testing are purified using a Waters semi-preparative HPLC equipped with a Phenomenex Luna® C18 reverse phase (5 micron, 30×75 mm) column having a flow rate of 45 mL/min. The mobile phase is a mixture of acetonitrile and $H_2O$ each containing 0.1% trifluoroacetic acid. During purification, a gradient of 30% to 80% acetonitrile over 8 minutes is used with fraction collection triggered by UV detection (220 nM). Pure fractions passed through PL-HCO$_3$ MP SPE (Varian) to remove trifluoroacetic acid and concentrated under vacuum on a lyophilizer. $^1$H spectra are recorded using an Inova 400 (100) MHz spectrometer (Varian).

The Compounds of Formula P-I, any of 2.1-2.13, Formula Q-I, wherein $R_2$ is H, Y is phenylene and $R_1$ is as defined in Formula P-I, any of 2.1-2.13, or Formula Q-I, for example $R_1$ is —N(H)—C(O)—C($R_{11}$)($R_{12}$)—N($R_{14}$)($R_{15}$), or —N(H)—C(O)-heterocycloalkyl, preferably —N(H)—C(O)—CH$_2$NH$_2$ or —N(H)—C(O)—CH$_2$-piperidine, may be prepared by first reacting 5-(3-nitrophenyl)-1,3,4-thiadiazol-2-amine (Int-4) with methyl 3-chloro-3-oxopropanoate, which product is then halogenated, e.g., reacting with phosphorous oxychloride in the presence of a base, e.g., diisopropyl ethyl amine or the like, optionally with heat, e.g., up to about 150° C., e.g., using microwave to produce 7-chloro-2-(3-nitrophenyl)-5H-[1,3,4]thiadiazolo[3,2-a]pyrimidin-5-one, (Int-5). Boc-protected piperazine is then reacted with Int-5 optionally in the presence of heat, e.g., up to about 150° C., e.g., using a microwave, to produce tert-butyl 4-(2-(3-nitrophenyl)-5-oxo-5H-[1,3,4]thiadiazolo[3,2-a]pyrimidin-7-yl)piperazine-1-carboxylate, Int-6. The nitro group on Int-6 is then reduced to an amine, e.g., by catalytic hydrogenation, e.g., using Raney Nickel and hydrazine to produce tert-butyl 4-(2-(3-aminophenyl)-5-oxo-5H-[1,3,4] thiadiazolo[3,2-a]pyrimidin-7-yl)piperazine-1-carboxylate, Int-7. Int-7 is then reacted with HOC(O)—C($R_{11}$)($R_{12}$)—N ($R_{13}$)($R_{14}$) in the presence of a activating agent, e.g., 1-ethyl-3-(3-dimethylaminopropyl) carbodiimide (EDC). Wherein $R_{13}$ and/or $R_{14}$ are H, HOC(O)—C($R_{11}$)($R_{12}$)—N ($R_{13}$)($R_{14}$) is preferably protected with a protecting group, e.g., a BOC protecting group, e.g. HOC(O)—C($R_{11}$)($R_{12}$)—N($R_{13}$)—BOC or HOC(O)—C($R_{11}$)($R_{12}$)—N($R_{14}$)—BOC. The resulting compound of Formula P-I, any of 2.1-2.13, or Formula Q-I is then deprotected, e.g., using acid, e.g., trifluoroacetic acid to provide the Compound of Formula P-I, any of 2.1-2.13, or Formula Q-I wherein $R_1$ is —N(H)—C(O)—C($R_{11}$)($R_{12}$)—N($R_{13}$)($R_{14}$), e.g., —N(H)—C(O)—CH$_2$NH$_2$. The synthesis may be summarized in the reaction scheme below:

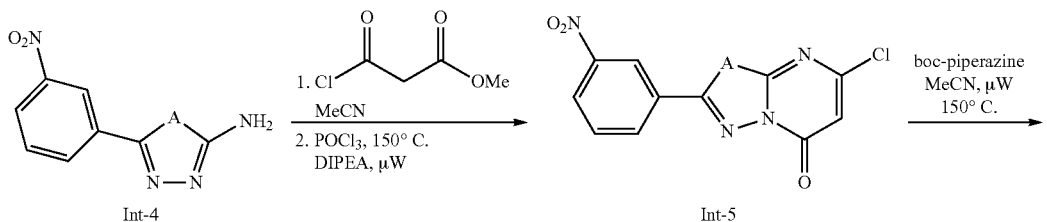

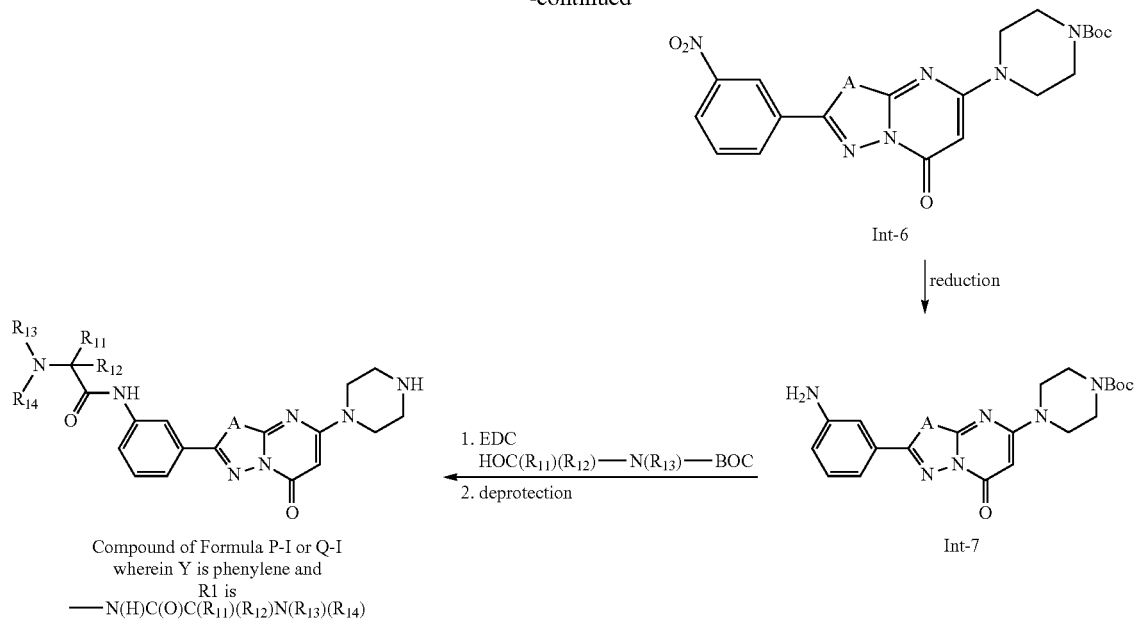

Specifically, the synthesis for the Compound of Formula P-I, any of 2.1-2.13, or Formula Q-I, wherein A is S, $R_2$ is H and $R_1$ is —N(H)—C(O)—CH$_2$NH$_2$ may be summarized in the reaction scheme below:

General Synthetic Procedures.

The synthesis methods described above and/or the following general procedures are used to synthesize compounds having different but analogous structures. All final

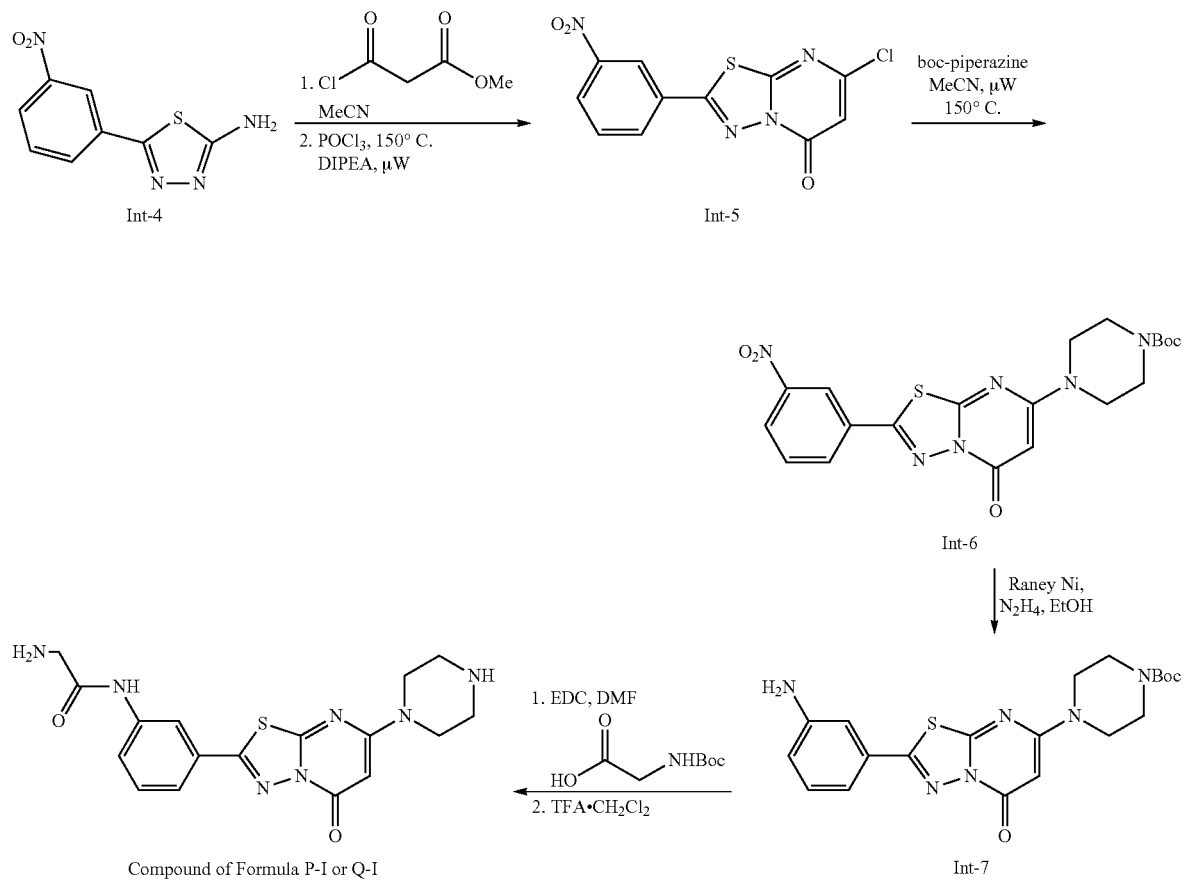

compounds differed only in the substitution off of the commercially available starting material.

Terms and Abbreviations:
ACN=acetonitrile,
DCM=dichloromethane,
DMF=N,N-dimethylforamide,
DCM=dichloromethane
DIPEA=diisopropylethylamine
DMSO=dimethyl sulfoxide,
EDC=1-ethyl-3-(3-dimethylaminopropyl) carbodiimide
EtOAc=ethyl acetate,
h=hour(s),
HCl=hydrochloric acid
HPLC=high performance liquid chromatography,
$K_2CO_3$=potassium carbonate,
m=multiplet,
min.=minute(s)
MeOH=methanol,
MeCN=acetonitrile
$MgSO_4$=magnesium sulfate
$NaHCO_3$=sodium bicarbonate,
NMR=nuclear magnetic resonance,
p=pentet,
$POCl_3$=phosphorous oxychloride
rt=room temperature,
s=singlet,
t=triplet,
TFA=trifluoroacetic acid,
THF=tetrahydrofuran,
TLC=thin layer chromatography.

Example 1

2-ethyl-7-(piperazin-1-yl)-5H-[1,3,4]thiadiazolo[3,2-a]pyrimidin-5-one

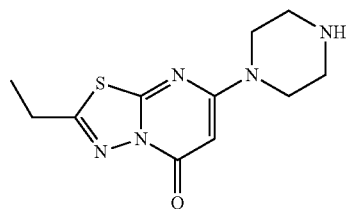 [SMILES: CCc1nn2c(=O)cc(N3CCNCC3)nc2s1]

Step 1: 7-chloro-2-ethyl-5H-[1,3,4]thiadiazolo[3,2-a]pyrimidin-5-one

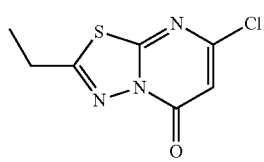

To a solution of 5-ethyl-1,3,4-thiadiazol-2-amines (5 g, 38.7 mmol, 1.0 equiv) in 200 mL anhydrous acetonitrile is added to methyl 3-chloro-3-oxopropionate (4.97 mL, 46.4 mmol, 1.2 equiv) and the mixture is stirred for 2 h at room temperature. After consumption of the starting material, phosphorous (V) oxychloride (40 mL, 429 mmol, 27 equiv) is added along with N,N-diisopropylethylamine (6.76 mL, 38.7 mmol, 1.0 equiv). The mixture is stirred at 150° C. for 25 min after which it is concentrated in vacuo and taken up in chloroform, poured over ice and washed with saturated $NaHCO_3$, water and brine. The organic layer is dried ($MgSO_4$) and concentrated in vacuo to give a dark, red oil. The residue is purified by column chromatography (silica gel, 0-10% EtOAc/Dichloromethane) to give 7-chloro-2-ethyl-5H-[1,3,4]thiadiazolo[3,2-a]pyrimidin-5-one (2.35 g, 28.2% yield) as a tan solid.

Step 2: tert-butyl 4-(2-ethyl-5-oxo-5H-[1,3,4]thiadiazolo[3,2-a]pyrimidin-7-yl)piperazine-1-carboxylate

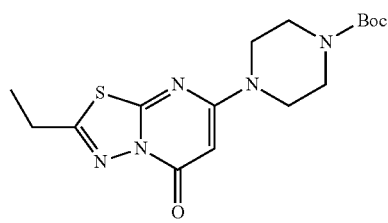 [SMILES: CCc1nn2c(=O)cc(N3CCN(C(=O)OC(C)(C)C)CC3)nc2s1]

To a solution of 7-chloro-2-ethyl-5H-[1,3,4]thiadiazolo[3,2-a]pyrimidin-5-one (2.0 g, 9.27 mmol, 1.0 equiv) in 50 mL of anhydrous acetonitrile in a microwave vial is added tert-butyl 1-piperazinecarboxylate (2.073 g, 11.13 mmol, 1.2 equiv) followed by N,N-diisopropylethylamine (4.86 mL, 27.8 mmol, 3.0 equiv). The mixture is heated in a microwave reactor for 25 min at 150° C. Upon completion, the mixture is concentrated in vacuo to give crude tert-butyl 4-(2-ethyl-5-oxo-5H-[1,3,4]thiadiazolo[3,2-a]pyrimidin-7-yl)piperazine-1-carboxylate as a yellow oil. This material is advanced directly to the next step.

Step 3: 2-ethyl-7-(piperazin-1-yl)-5H-[1,3,4]thiadiazolo[3,2-a]pyrimidin-5-one

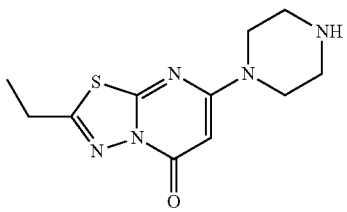 [SMILES: CCc1nn2c(=O)cc(N3CCNCC3)nc2s1]

To a solution of tert-butyl 4-(2-ethyl-5-oxo-5H-[1,3,4]thiadiazolo[3,2-a]pyrimidin-7-yl)piperazine-1-carboxylate (3.39 g, 9.28 mmol, 1.0 equiv) in 40 mL of dichloromethane is added trifluoroacetic acid (10 ml, 130 mmol, 14 equiv). The mixture stirred for 18 h, after which it is concentrated in vacuo and azeotroped with dichloroethane to give a yellow solid. The crude residue is dissolved in MeOH and purified by HPLC to give 2-ethyl-7-(piperazin-1-yl)-5H-[1,3,4]thiadiazolo[3,2-a]pyrimidin-5-one (2.053 g, 83% yield) as an off-white solid. $^1$H-NMR (400 MHz, DMSO-$d_6$) δ ppm 5.30 (s, 1H), 3.37-3.44 (m, 4H), 2.94 (q, J=7.56 Hz, 2H), 2.64-2.73 (m, 4H), 1.25 (t, 3H); LCMS: (electrospray +ve), m/z 266.0 (MH)$^+$; HPLC: $t_R$=2.71 min, $UV_{254}$=100%. HRMS (ESI): m/z calcd for $C_{11}H_{16}N_5OS$ [M+H]$^+$ 266.1069. found 266.1073.

Example 2

2-ethyl-7-(4-methylpiperazin-1-yl)-5H-[1,3,4]thiadiazolo[3,2-a]pyrimidin-5-one

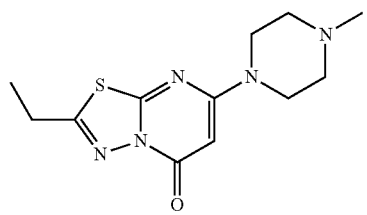 [SMILES: CCc1nn2c(=O)cc(N3CCN(C)CC3)nc2s1]

This example is prepared by following the same procedures as described in Example 1 above except substituting I-methylpiperazine for Boc-piperazine. $^1$H NMR (400 MHz, CHLOROFORM-d) δ ppm 5.51 (s, 1H), 4.32 (br. s., 2H), 3.39-3.75 (m, 4H), 3.01 (q, J=7.50 Hz, 2H), 2.83 (s, 3H), 1.96-2.55 (m, 2H), 1.41 (t, 3H); LCMS: (electrospray +ve), m/z 280.1 (MH)$^+$; HPLC: $t_R$=2.69 min, UV$_{254}$=100%. HRMS (ESI): m/z calcd for $C_{12}H_{18}N_5OS$ [M+H]$^+$ 280.1226. found 280.1224.

Example 3

7-(2,6-dimethylpiperazin-1-yl)-2-ethyl-5H-[1,3,4]thiadiazolo[3,2-a]pyrimidin-5-one

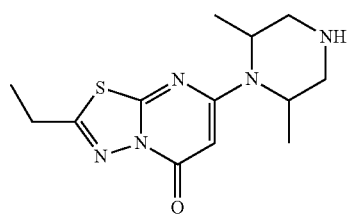 [SMILES: CCc1nn2c(=O)cc(N3C(C)CNCC3C)nc2s1]

This example is prepared by following the same procedures as described in Example 1 above except substituting tert-butyl 3,5-dimethylpiperazine-1-carboxylate for Boc-piperazine. $^1$H NMR (400 MHz, DMSO-d$_6$) δ ppm 5.32 (s, 1H), 4.03 (d, J=9.78 Hz, 2H), 2.92 (q, J=7.43 Hz, 2H), 2.53-2.66 (m, 2H), 2.18-2.30 (m, 2H), 1.23 (t, J=7.43 Hz, 3H), 0.94 (d, 6H); LCMS: (electrospray +ve), m/z 294.2 (MH)$^+$; HPLC: $t_R$=2.86 min, UV$_{254}$=100%. HRMS (ESI): m/z calcd for $C_{13}H_{20}N_5OS$ [M+H]$^+$ 294.1383. found 294.1382.

Example 4

2-ethyl-7-(4-ethylpiperazin-1-yl)-5H-[1,3,4]thiadiazolo[3,2-a]pyrimidin-5-one

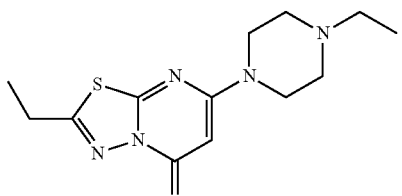

This example is prepared by following the same procedures as described in Example 1 above except substituting N-ethylpiperazine for Boc-piperazine. $^1$H NMR (400 MHz, CHLOROFORM-d) δ ppm 5.49 (s, 1H), 4.33 (br, s., 2H), 3.42-3.75 (m, 4H), 3.12 (q, J=7.37 Hz, 2H), 3.01 (q, J=7.50 Hz, 2H), 2.76 (br. s., 2H), 1.32-1.45 (m, 6H); LCMS: (electrospray +ve), m/z 294.1 (MH)$^+$; HPLC: $t_R$=2.76 min, UV$_{254}$=100%. HRMS (ESI): m/z calcd for $C_{13}H_{20}N_5OS$ [M+H]$^+$ 294.1383. found 294.1381.

Example 5

2-ethyl-6-methyl-7-(piperazin-1-yl)-5H-[1,3,4]thiadiazolo[3,2-a]pyrimidin-5-one

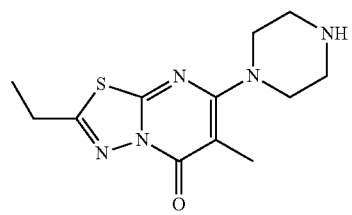 [SMILES: CCc1nn2c(=O)c(C)c(N3CCNCC3)nc2s1]

This example is prepared by following the same procedures as described in Example 1 above except substituting 3-ethoxy-2-methyl-3-oxopropanoic acid for 3-ethoxy-3-oxopropanoic acid. $^1$H NMR (400 MHz, DMSO-d$_6$) δ ppm 3.09-3.16 (m, 4H), 2.94 (q, J=7.43 Hz, 2H), 2.66-2.75 (m, 4H), 1.88 (s, 3H), 1.24 (t, J=7.63 Hz, 3H); LCMS: (electrospray +ve), m/z 280.1 (MH)$^+$; HPLC: $t_R$=2.82 min, UV$_{254}$=100%. HRMS (ESI): m/z calcd for $C_{12}H_{18}N_5OS$ [M+H]$^+$ 280.1227. found 280.1230.

Example 6

2-ethyl-6-fluoro-7-(piperazin-1-yl)-5H-[1,3,4]thiadiazolo[3,2-a]pyrimidin-5-one

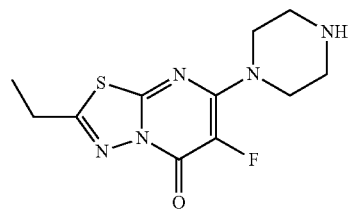 [SMILES: CCc1nn2c(=O)c(F)c(N3CCNCC3)nc2s1]

This example is prepared by following the same procedures as described in Example 1 above except substituting 3-ethoxy-2-fluoro-3-oxopropanoic acid for 3-ethoxy-3-oxopropanoic acid. $^1$H NMR (400 MHz, DMSO-d$_6$) δ ppm 3.46-3.55 (m, 4H), 2.96 (q, J=7.43 Hz, 2H), 2.68-2.76 (m, 4H), 1.26 (t, 3H); LCMS: (electrospray +ve), m/z 284.1 (MH)$^+$; HPLC: $t_R$=2.59 min, UV$_{254}$=100%. HRMS (ESI): m/z calcd for $C_{11}H_{15}N_5OS$ [M+H]$^+$ 284.0975. found 284.0974.

Example 7

4-(5-oxo-7-(piperazin-1-yl)-5H-[1,3,4]thiadiazolo[3,2-a]pyrimidin-2-yl)benzoic acid

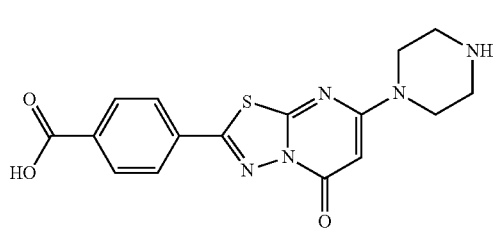 [SMILES: O=C(O)c1ccc(-c2nn3c(=O)cc(N4CCNCC4)nc3s2)cc1]

This example is prepared by following the same procedures as described in Example 1 above except substituting methyl 4-(5-amino-1,3,4-thiadiazol-2-yl)benzoate for 5-ethyl-1,3,4-thiadiazol-2-amine to obtain tert-butyl 4-(2-(4-(methoxycarbonyl)phenyl)-5-oxo-5H-[1,3,4]thiadiazolo[3,2-a]pyrimidin-7-yl)piperazine-1-carboxylate as a yellow oil. This oil (99 mg, 0.21 mmol, 1.0 equiv) is taken up in a 1:1 THF/water mixture (3.0 mL), and to it is added lithium hydroxide (10 mg, 0.420 mmol, 2.0 equiv). After stirring for 2 h, the mixture is filtered and concentrated to give a yellow oil which is taken on crude to the same deprotection step mentioned above to give 4-(5-oxo-7-(piperazin-1-yl)-5H-[1,3,4]thiadiazolo[3,2-a]pyrimidin-2-yl)benzoic acid as a tan solid β3 mg, 44%). $^1$H NMR (400 MHz, DMSO-d$_6$) δ ppm 8.86 (br. s., 1H), 8.07-8.14 (m, 2H), 7.99-8.06 (m, 2H), 5.59 (s, 1H), 4.06 (br. s., 1H), 3.69-3.81 (m, 4H), 3.08-3.21 (m, 4H); LCMS: (electrospray +ve), m/z 358.1 (MH)$^+$; HPLC: t$_R$=3.03 min, UV$_{254}$=100%. HRMS (ESI): m/z calcd for C$_{16}$H$_{16}$N$_5$O$_3$S [M+H]$^+$ 358.0969. found 358.0969.

Example 8

5-oxo-7-(piperazin-1-yl)-5H-[1,3,4]thiadiazolo[3,2-a]pyrimidine-2-carboxylic acid

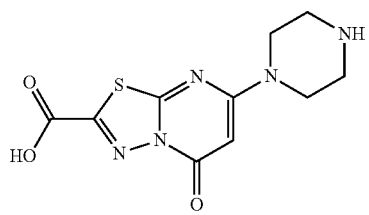 [SMILES: O=C(O)c1nn2c(=O)cc(N3CCNCC3)nc2s1]

This example is prepared by following the same procedures as described in Example 1 above except substituting methyl 5-amino-1,3,4-thiadiazole-2-carboxylate for methyl 4-(5-amino-1,3,4-thiadiazol-2-yl)benzoate. $^1$H NMR (400 MHz, DMSO-d$_6$) δ ppm 8.58 (br. s., 1H), 5.90 (s, 1H), 3.68-3.78 (m, 4H), 3.10-3.19 (m, 4H); LCMS: (electrospray +ve), m/z 282.0 (MH)$^+$; HPLC: t$_R$=0.55 min, UV$_{254}$=95%. HRMS (ESI): m/z calcd for C$_{10}$H$_{12}$N$_5$O$_3$S [M+H]$^+$ 282.0655. found 282.0658.

Example 9

7-(piperazin-1-yl)-2-(pyridin-4-yl)-5H-[1,3,4]thiadiazolo[3,2-a]pyrimidin-5-one

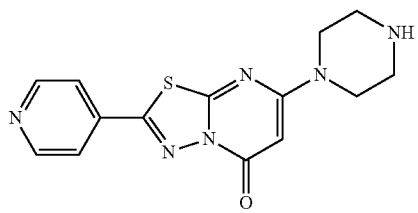 [SMILES: O=c1cc(N2CCNCC2)nc2sc(-c3ccncc3)nn12]

This example is prepared by following the same procedures as described in Example 1 above except substituting 5-(pyridin-4-yl)-1,3,4-thiadiazol-2-amine for 5-ethyl-1,3,4-thiadiazol-2-amine. $^1$H NMR (400 MHz, DMSO-d$_6$) δ ppm 8.80 (dd, J=4.30, 1.57 Hz, 2H), 7.85 (dd, J=4.30, 1.57 Hz, 2H), 5.40 (s, 1H), 3.42-3.51 (m, 4H), 2.66-2.75 (m, 4H); LCMS: (electrospray +ve), m/z 315.0 (MH)$^+$; HPLC: t$_R$=2.55 min, UV$_{254}$=100%. HRMS (ESI): m/z calcd for C$_{14}$H$_{15}$N$_6$OS [M+H]$^+$ 315.1023. found 315.1024.

Example 10

2-tert-butyl-7-(piperazin-1-yl)-5H-[1,3,4]thiadiazolo[3,2-a]pyrimidin-5-one

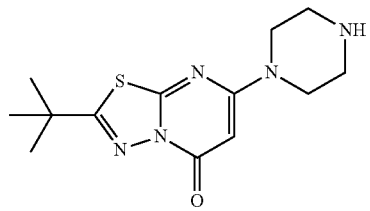 [SMILES: CC(C)(C)c1nn2c(=O)cc(N3CCNCC3)nc2s1]

This example is prepared by following the same procedures as described in Example 1 above except substituting 5-tert-butyl-1,3,4-thiadiazol-2-amine for 5-ethyl-1,3,4-thiadiazol-2-amine. $^1$H NMR (400 MHz, DMSO-d$_6$) δ ppm 5.32 (s, 1H), 3.40 (m, 4H), 2.67 (m, 4H), 1.35 (s, 9H); LCMS: (electrospray +ve), m/z 294.1 (MH)$^+$; HPLC: t$_R$=2.52 min (4 min method), UV$_{254}$=100%. HRMS (ESI): m/z calcd for C$_{13}$H$_{20}$N$_5$OS [M+H]$^+$ 294.1383. found 294.1382.

Example 11

2-(4-nitrophenyl)-7-(piperazin-1-yl)-5H-[1,3,4]thiadiazolo[3,2-a]pyrimidin-5-one

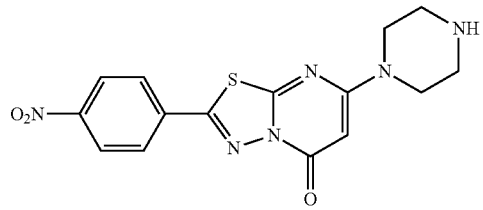 [SMILES: O=c1cc(N2CCNCC2)nc2sc(-c3ccc([N+](=O)[O-])cc3)nn12]

This example is prepared by following the same procedures as described in Example 1 above except substituting 5-(4-nitrophenyl)-1,3,4-thiadiazol-2-amine for 5-ethyl-1,3,4-thiadiazol-2-amine. $^1$H NMR (400 MHz, DMSO-$d_6$) δ ppm 8.39 (d, J=9.00 Hz, 2H), 8.12-8.20 (m, 2H), 5.40 (s, 1H), 3.43-3.51 (m, 4H), 2.64-2.75 (m, 4H); LCMS: (electrospray +ve), m/z 359.1 (MH)$^+$; HPLC: $t_R$=2.60 min (4 min method), UV$_{254}$=100%. HRMS (ESI): m/z calcd for $C_{15}H_{15}N_6O_3S$ [M+H]$^+$ 359.0921. found 359.0919.

Example 12

2-ethyl-7-(piperazin-1-yl)-5H-[1,3,4]oxadiazolo[3,2-a]pyrimidin-5-one

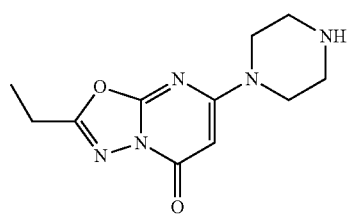

This example is prepared by following the same procedures as described in Example 1 above except substituting 5-ethyl-1,3,4-oxadiazol-2-amine for 5-ethyl-1,3,4-thiadiazol-2-amine. $^1$H NMR (400 MHz, DMSO-$d_6$) δ ppm 5.23 (s, 1H), 3.35-3.43 (m, 4H), 2.80 (q, J=7.56 Hz, 2H), 2.64-2.73 (m, 4H), 1.23 (t, 3H); LCMS: (electrospray +ve), m/z 250.1 (MH)$^+$; HPLC: $t_R$=2.41 min, UV$_{254}$=100%. HRMS (ESI): m/z calcd for $C_{11}H_{16}N_5O_2$ [M+H]$^+$ 250.1299. found 250.1302.

Example 13

2-phenyl-7-(piperazin-1-yl)-5H-[1,3,4]thiadiazolo[3,2-a]pyrimidin-5-one

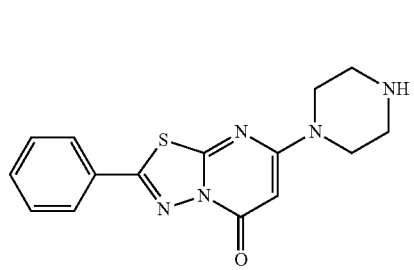 [SMILES: O=c1cc(N2CCNCC2)nc2sc(-c3ccccc3)nn12]

This example is prepared by following the same procedures as described in Example 1 above except substituting 5-phenyl-1,3,4-thiadiazol-2-amine for 5-ethyl-1,3,4-thiadiazol-2-amine. $^1$H NMR (400 MHz, DMSO-$d_6$) δ ppm 7.84-7.93 (m, 2H), 7.53-7.66 (m, 3H), 5.38 (s, 1H), 3.40-3.51 (m, 4H), 2.65-2.77 (m, 4H); LCMS: (electrospray +ve), m/z 314.1 (MH)$^+$; HPLC: $t_R$=3.37 min, UV$_{254}$=100%. HRMS (ESI): m/z calcd for $C_{15}H_{16}N_5OS$ [M+H]$^+$ 314.1070. found 314.1073.

Examples 14-15 are Prepared by Using General Procedure Described Below

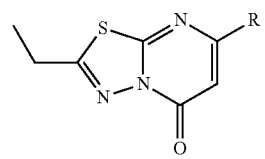

In a microwave vial is added 7-chloro-2-ethyl-5H-[1,3,4]thiadiazolo[3,2-a]pyrimidin-5-one (50 mg, 0.232 mmol, 1.0 equiv) followed by the R-boronic acid (0.464 mmol, 2.0 equiv), sodium carbonate (73.7 mg, 0.696 mmol, 3.0 equiv), and tetrakis(triphenylphosphine)palladium(0) (13.40 mg, 0.012 mmol, 0.05 equiv). The solids are taken up in DMF (1.4 mL), Ethanol (0.700 mL), and Water (0.350 mL). The mixture is then heated in the microwave at 120° C. for 25 min. Upon completion, the mixture is taken up in ethyl acetate and saturated potassium hydrogen sulfate. The layers are separated and the aqueous layer is extracted with ethyl acetate. The combined organic extracts are then washed with saturated sodium bicarbonate, water, and brine. They are dried over magnesium sulfate and concentrated in vacuo to give a yellow oil which is purified by HPLC to give 2-ethyl-7-aryl-5H-[1,3,4]thiadiazolo[3,2-a]pyrimidin-5-ones (20-40%) as tan solids.

Example 14

2-ethyl-7-(pyridin-3-yl)-5H-[1,3,4]thiadiazolo[3,2-a]pyrimidin-5-one $^1$H NMR (400 MHz, DMSO-$d_6$) δ ppm 9.21 (d, J=2.35 Hz, 1H), 8.61-8.68 (m, 1H), 8.40 (ddd, J=8.02, 2.15, 1.96 Hz, 1H), 7.49 (dd, J=8.02, 4.89 Hz, 1H), 7.07 (s, 1H), 3.04 (q, J=7.43 Hz, 2H), 1.30 (t, 3H); LCMS: (electrospray +ve), m/z 259.1 (MH)$^+$; HPLC: $t_R$=2.98 min, UV$_{254}$=100%. HRMS (ESI): m/z calcd for $C_{12}H_{11}N_4OS$ [M+H]$^+$ 259.0648. found 259.0639.

Example 15

2-ethyl-7-(1,2,3,6-tetrahydropyridin-4-yl)-5H-[1,3,4]thiadiazolo[3,2-a]pyrimidin-5-one

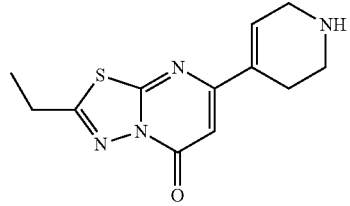

This example are prepared by following the same general procedure above for examples 14-15 to obtain tert-butyl 4-(2-ethyl-5-oxo-5H-[1,3,4]thiadiazolo[3,2-a]pyrimidin-7-yl)-5,6-dihydropyridine-1(2H)-carboxylate, which is taken on to the same deprotection procedure as with 2-ethyl-7-(piperazin-1-yl)-5H-[1,3,4]thiadiazolo[3,2-a]pyrimidin-5-one described in step 3 of Example 1. $^1$H NMR (400 MHz, DMSO-$d_6$) δ ppm 6.94-7.00 (m, 1H), 6.21 (s, 1H), 3.36 (d, J=3.13 Hz, 2H), 2.99 (q, J=7.43 Hz, 2H), 2.81 (t, J=5.48 Hz, 2H), 2.21 (d, 2H), 1.26 (t, J=7.43 Hz, 3H); LCMS: (electrospray +ve), m/z 263.0 (MH)$^+$; HPLC: $t_R$=2.32 min (4 min method), UV$_{254}$=100%. HRMS (ESI): m/z calcd for $C_{12}H_{15}N_4OS$ [M+H]$^+$ 263.0960. found 263.0958.

Examples 16-26 are Prepared Using the General Procedures Below

Step 1: 5-(3-bromophenyl)-1,3,4-thiadiazol-2-amine

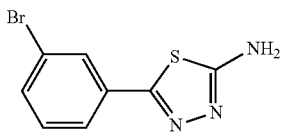 [SMILES: Nc1nnc(-c2cccc(Br)c2)s1]

To a solution of thiosemicarbazide (0.493 g, 5.40 mmol, 1.0 equiv) in 6 mL of water at 70° C. is added a solution of 3-bromobenzaldehyde (0.633 ml, 5.40 mmol, 1.0 equiv) in 4.5 mL ethanol. After the precipitate formed, iron(III) chloride hexahydrate (2.92 g, 10.81 mmol, 2.0 equiv) in 6 mL water is added and the mixture is stirred for 2.5 h at 85° C. Upon completion, the mixture is allowed to cool to room temperature and the resulting precipitate is collected by filtration and taken up in 12 mL pyridine. Ice water is then added to the pyridine slurry. The mixture is cooled then filtered to give 5-(3-bromophenyl)-1,3,4-thiadiazol-2-amine (553 mg, 39.9% yield) as a brown solid. $^1$H NMR (400 MHz, DMSO-$d_6$) δ ppm 7.85-7.88 (m, 1H), 7.67 (d, J=8.22 Hz, 1H), 7.53-7.59 (m, 1H), 7.45 (s, 2H), 7.36 (t, J=8.02 Hz, 1H);

Step 2

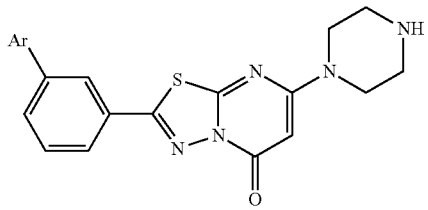

Boc-protected 2-(3-bromophenyl)-7-(piperazin-1-yl)-5H-[1,3,4]thiadiazolo[3,2-a]pyrimidin-5-one may be prepared as similarly described in step 2 of Example 1. To a solution of tert-butyl 4-(2-(3-bromophenyl)-5-oxo-5H-[1,3,4]thiadiazolo[3,2-a]pyrimidin-7-yl)piperazine-1-carboxylate (40 mg, 0.081 mmol, 1.0 equiv) in 1 mL DMF, 0.5 mL ethanol and 0.25 mL water in a microwave vial is added the boronic acid (0.162 mmol, 2.0 equiv), sodium carbonate (25.8 mg, 0.244 mmol, 3.0 equiv), and tetrakis(triphenylphosphine) palladium(0) (4.69 mg, 4.06 μmol, 0.05 equiv). The mixture is heated in a microwave reactor for 30 min at 120° C. Upon completion the mixture is filtered through a thiol-SPE column (Stratospheres) and the resulting solution is concentrated in vacuo to give crude tert-butyl 4-(5-oxo-2-(3-(aryl-4-yl)phenyl)-5H-[1,3,4]thiadiazolo[3,2-a]pyrimidin-7-yl)piperazine-1-carboxylate as a yellow oil. The residue is then taken on crude to the next reaction, which followed the same deprotection procedure as described in step 3 of Example 1 to give 7-(piperazin-1-yl)-2-(3-(aryl-4-yl)phenyl)-5H-[1,3,4]thiadiazolo[3,2-a]pyrimidin-5-ones (30-50%) as tan solids.

Example 16

7-(piperazin-1-yl)-2-(3-(pyridin-4-yl)phenyl)-5H-[1,3,4]thiadiazolo-[3,2-a]pyrimidin-5-one

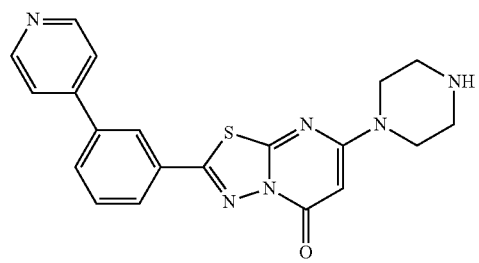 [SMILES: O=c1cc(N2CCNCC2)nc2sc(-c3cccc(-c4ccncc4)c3)nn12]

Step 1: 5-(3-bromophenyl)-1,3,4-thiadiazol-2-amine

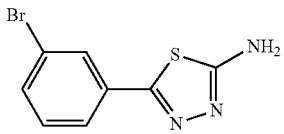 [SMILES: Nc1nnc(-c2cccc(Br)c2)s1]

To a solution of thiosemicarbazide (0.493 g, 5.40 mmol, 1.0 equiv) in 6 mL of water at 70° C. is added a solution of 3-bromobenzaldehyde (0.633 ml, 5.40 mmol, 1.0 equiv) in 4.5 mL ethanol. After the precipitate is formed, iron(III) chloride hexahydrate (2.92 g, 10.81 mmol, 2.0 equiv) in 6 mL water is added and the mixture is stirred for 2.5 h at 85° C. Upon completion, the mixture is allowed to cool to room temperature and the resulting precipitate is collected by filtration and taken up in 12 mL pyridine. Ice water is then added to the pyridine slurry. The mixture is cooled then filtered to give 5-(3-bromophenyl)-1,3,4-thiadiazol-2-amine (553 mg, 39.9% yield) as a brown solid. $^1$H NMR (400 MHz, DMSO-$d_6$) δ ppm 7.85-7.88 (m, 1H), 7.67 (d, J=8.22 Hz, 1H), 7.53-7.59 (m, 1H), 7.45 (s, 2H), 7.36 (t, J=8.02 Hz, 1H);

Step 2: 7-(piperazin-1-yl)-2-(3-(pyridin-4-yl)phenyl)-5H-[1,3,4]thiadiazolo-[3,2-a]pyrimidin-5-one

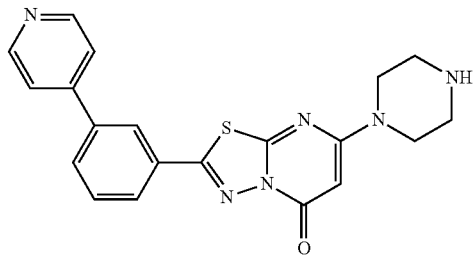 [SMILES: O=c1cc(N2CCNCC2)nc2sc(-c3cccc(-c4ccncc4)c3)nn12]

Boc-protected 2-(3-bromophenyl)-7-(piperazin-1-yl)-5H-[1,3,4]thiadiazolo[3,2-a]pyrimidin-5-one may be prepared as similarly described above (or in Steps 1 and 2 of Example 1), except 5-(3-bromophenyl)-1,3,4-thiadiazol-2-amine is used as the starting material in step 1.

To a solution of tert-butyl 4-(2-(3-bromophenyl)-5-oxo-5H-[1,3,4]thiadiazolo[3,2-a]pyrimidin-7-yl)piperazine-1-carboxylate (40 mg, 0.081 mmol, 1.0 equiv) in 1 mL DMF, 0.5 mL ethanol and 0.25 mL water in a microwave vial is added 4-pyridineboronic acid (19.97 mg, 0.162 mmol, 2.0 equiv), sodium carbonate (25.8 mg, 0.244 mmol, 3.0 equiv), and tetrakis(triphenylphosphine)palladium(0) (4.69 mg, 4.06 μmol, 0.05 equiv). The mixture is heated in a microwave reactor for 30 min at 120° C. Upon completion the mixture is filtered through a thiol-SPE column (Stratospheres) and the resulting solution is concentrated in vacuo to give crude tert-butyl 4-(5-oxo-2-(3-(pyridin-4-yl)phenyl)-5H-[1,3,4]thiadiazolo[3,2-a]pyrimidin-7-yl)piperazine-1-carboxylate as a yellow oil. The residue is then taken on crude to the next reaction, which follows the same deprotection procedure as described in Step 3 of Example 1 to give 7-(piperazin-1-yl)-2-(3-(pyridin-4-yl)phenyl)-5H-[1,3,4]thiadiazolo[3,2-a]pyrimidin-5-one (12 mg, 38%) as a tan solid. $^1$H NMR (400 MHz, DMSO-$d_6$) δ ppm 8.67 (dd, J=4.30, 1.57 Hz, 2H), 8.18 (s, 1H), 8.02 (dd, J=16.43, 8.22 Hz, 2H), 7.70-7.82 (m, 3H), 5.40 (s, 1H), 3.42-3.51 (m, 4H), 2.68-2.75 (m, 4H); LCMS: (electrospray +ve), m/z 391.1 (MH)$^+$; HPLC: $t_R$=2.82 min, UV$_{254}$=100%. HRMS (ESI): m/z calcd for $C_{20}H_{19}N_6OS$ [M+H]$^+$ 391.1321. found 391.1322.

Example 17

7-(piperazin-1-yl)-2-(3-(pyridin-3-yl)phenyl)-5H-[1,3,4]thiadiazolo[3,2-a]pyrimidin-5-one

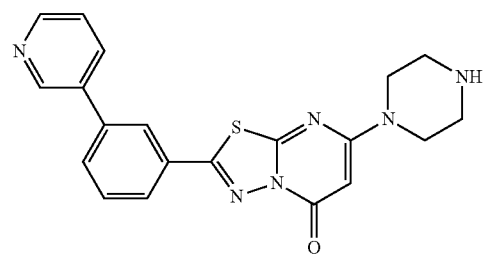 [SMILES: O=c1cc(N2CCNCC2)nc2sc(-c3cccc(-c4cccnc4)c3)nn12]

$^1$H NMR (400 MHz, DMSO-$d_6$) δ ppm 8.96 (d, J=1.57 Hz, 1H), 8.61 (dd, J=4.70, 1.57 Hz, 1H), 8.14-8.20 (m, 1H), 8.12 (s, 1H), 7.93-8.01 (m, 2H), 7.72 (t, J=7.83 Hz, 1H), 7.52 (dd, J=8.41, 5.28 Hz, 1H), 5.39 (s, 1H), 3.41-3.50 (m, 4H), 2.66-2.75 (m, 4H); LCMS: (electrospray +ve), m/z 391.1 (MH)$^+$; HPLC: $t_R$=2.87 min, UV$_{254}$=100%. HRMS (ESI): m/z calcd for $C_{20}H_{19}N_6OS$ [M+H]$^+$391.1334. found 391.1337.

Example 18

2-(3-(1H-pyrazol-4-yl)phenyl)-7-(piperazin-1-yl)-5H-[1,3,4]thiadiazolo[3,2-a]pyrimidin-5-one

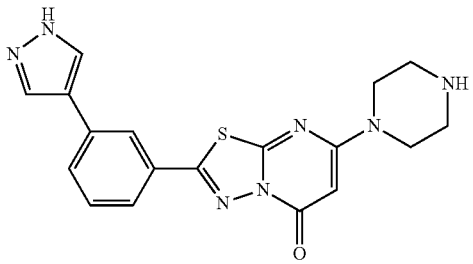 [SMILES: O=c1cc(N2CCNCC2)nc2sc(-c3cccc(-c4cn[nH]c4)c3)nn12]

$^1$H NMR (400 MHz, DMSO-$d_6$) δ ppm 13.06 (br. s., 1H), 8.16 (s, 2H), 8.00 (s, 1H), 7.85 (d, J=7.83 Hz, 1H), 7.70 (d, J=8.61 Hz, 1H), 7.55 (t, J=7.83 Hz, 1H), 5.39 (s, 1H), 3.44 (d, J=5.09 Hz, 4H), 2.65-2.74 (m, 4H); LCMS: (electrospray +ve), m/z 380.1 (MH)$^+$; HPLC: $t_R$=3.53 min, UV$_{254}$=100%. HRMS (ESI): m/z calcd for $C_{18}H_{18}N_7OS$ [M+H]$^+$ 380.1288. found 380.1290.

Example 19

2-(3-(6-fluoropyridin-3-yl)phenyl)-7-(piperazin-1-yl)-5H-[1,3,4]thiadiazolo[3,2-a]pyrimidin-5-one

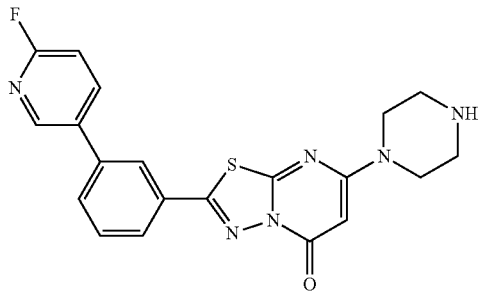 [SMILES: O=c1cc(N2CCNCC2)nc2sc(-c3cccc(-c4ccc(F)nc4)c3)nn12]

$^1$H NMR (400 MHz, DMSO-d$_6$) δ ppm 8.64 (d, J=2.74 Hz, 1H), 8.39 (td, J=8.22, 2.74 Hz, 1H), 8.11 (s, 1H), 7.97 (dd, J=8.22, 1.56 Hz, 2H), 7.72 (t, J=8.02 Hz, 1H), 7.32 (dd, J=8.61, 2.35 Hz, 1H), 5.40 (s, 1H), 3.42-3.50 (m, 4H), 2.67-2.75 (m, 4H); LCMS: (electrospray +ve), m/z 409.0 (MH)$^+$; HPLC: t$_R$=3.81 min, UV$_{254}$=100%. HRMS (ESI): m/z calcd for C$_{20}$H$_{18}$FN$_6$OS [M+H]$^+$ 409.1242. found 409.1233.

Example 20

2-(3-(2-fluoropyridin-4-yl)phenyl)-7-(piperazin-1-yl)-5H-[1,3,4]thiadiazolo[3,2-a]pyrimidin-5-one

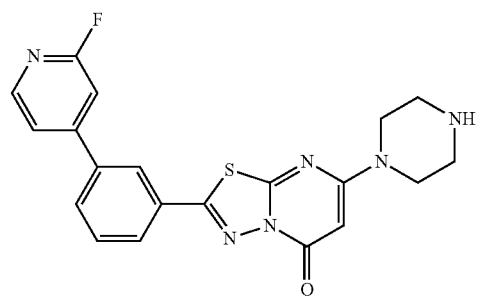 [SMILES: O=c1cc(N2CCNCC2)nc2sc(-c3cccc(-c4ccnc(F)c4)c3)nn12]

$^1$H NMR (400 MHz, DMSO-d$_6$) δ ppm 8.34 (d, J=5.28 Hz, 1H), 8.21 (t, J=1.66 Hz, 1H), 8.00-8.12 (m, 2H), 7.71-7.81 (m, 2H), 7.65 (s, 1H), 5.39 (s, 1H), 3.41-3.48 (m, 4H), 2.66-2.75 (m, 4H); LCMS: (electrospray +ve), m/z 409.1 (MH)$^+$; HPLC: t$_R$=3.82 min, UV$_{254}$=100%. HRMS (ESI): m/z calcd for C$_{20}$H$_{18}$FN$_6$OS [M+H]$^+$ 409.1244. found 409.1246.

Example 21

3'-(5-oxo-7-(piperazin-1-yl)-5H-[1,3,4]thiadiazolo[3,2-a]pyrimidin-2-yl)biphenyl-4-carboxylic acid

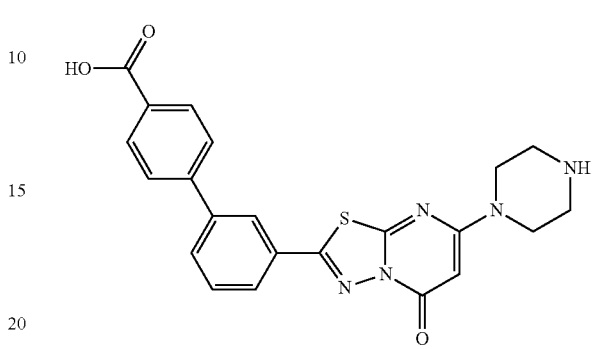

$^1$H NMR (400 MHz, DMSO-d$_6$) δ ppm 13.04 (br. s., 1H), 8.76 (br. s., 1H), 8.14-8.18 (m, 1H), 8.05 (d, J=8.61 Hz, 2H), 7.94-8.03 (m, 2H), 7.88 (d, J=8.61 Hz, 2H), 7.73 (t, J=8.02 Hz, 1H), 5.61 (s, 1H), 3.71-3.82 (m, 4H), 3.16 (br. s., 4H); LCMS: (electrospray +ve), m/z 434.1 (MH)$^+$; HPLC: t$_R$=3.79 min, UV$_{254}$=100%. HRMS (ESI): m/z calcd for C$_{22}$H$_{20}$N$_5$O$_3$S [M+H]$^+$ 434.1281. found 434.1270.

Example 22

3'-(5-oxo-7-(piperazin-1-yl)-5H-[1,3,4]thiadiazolo[3,2-a]pyrimidin-2-yl)biphenyl-3-carboxylic acid

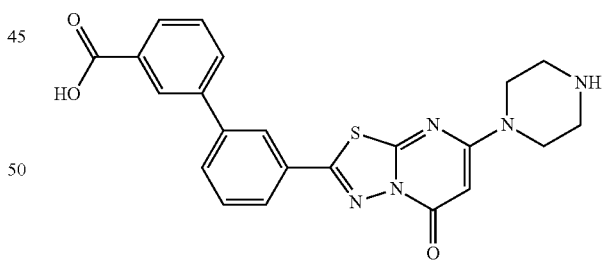

$^1$H NMR (400 MHz, DMSO-d$_6$) δ ppm 13.15 (br. s., 1H), 8.76 (br. s., 1H), 8.23 (t, J=1.57 Hz, 1H), 8.14 (t, J=1.66 Hz, 1H), 7.90-8.05 (m, 4H), 7.72 (t, J=7.92 Hz, 1H), 7.64 (t, J=7.83 Hz, 1H), 5.61 (s, 1H), 3.69-3.83 (m, 4H), 3.16 (br. s., 4H); LCMS: (electrospray +ve), m/z 434.1 (MH)$^+$; HPLC: t$_R$=3.94 min, UV$_{254}$=100%. HRMS (ESI): m/z calcd for C$_{22}$H$_{20}$N$_5$O$_3$S [M+H]$^+$ 434.1282. found 434.1281.

Example 23

3'-(5-oxo-7-(piperazin-1-yl)-5H-[1,3,4]thiadiazolo[3,2-a]pyrimidin-2-yl)biphenyl-4-carboxamide

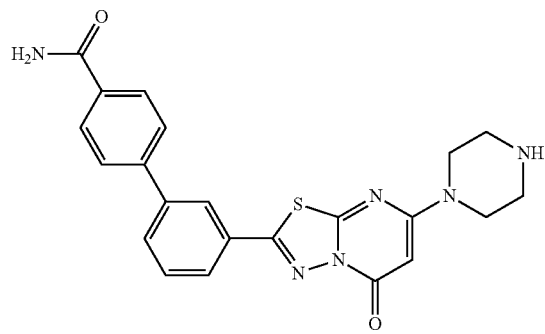 [SMILES: NC(=O)c1ccc(-c2cccc(-c3nn4c(=O)cc(N5CCNCC5)nc4s3)c2)cc1]

$^1$H NMR (400 MHz, DMSO-d$_6$) δ ppm 8.12 (t, J=1.66 Hz, 1H), 8.02-8.06 (m, 1H), 7.89-8.01 (m, 3H), 7.79-7.86 (m, 2H), 7.70 (t, J=7.83 Hz, 1H), 7.39 (br. s., 1H), 5.40 (s, 1H), 3.41-3.50 (m, 4H), 2.66-2.76 (m, 4H); LCMS: (electrospray +ve), m/z 433.1 (MH)$^+$; HPLC: t$_R$=3.56 min, UV$_{254}$=100%. HRMS (ESI): m/z calcd for C$_{22}$H$_{20}$N$_6$O$_2$S [M+H]$^+$ 433.1441. found 433.1447.

Example 24

4-(3-(5-oxo-7-(piperazin-1-yl)-5H-[1,3,4]thiadiazolo[3,2-a]pyrimidin-2-yl)phenyl)thiophene-2-carboxylic acid

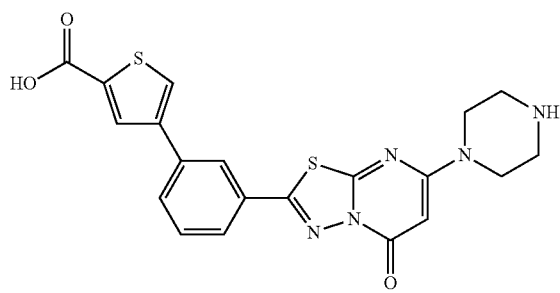 [SMILES: O=C(O)c1cc(-c2cccc(-c3nn4c(=O)cc(N5CCNCC5)nc4s3)c2)cs1]

$^1$H NMR (400 MHz, DMSO-d$_6$) δ ppm 13.27 (br. s., 1H), 8.77 (br. s., 1H), 8.37 (d, J=1.56 Hz, 1H), 8.24 (d, J=1.56 Hz, 1H), 8.15 (t, J=1.66 Hz, 1H), 8.03 (ddd, J=8.12, 1.47, 1.17 Hz, 1H), 7.89 (ddd, J=8.22, 1.37, 0.98 Hz, 1H), 7.65 (t, J=7.92 Hz, 1H), 5.60 (s, 1H), 3.70-3.83 (m, 4H), 3.08-3.22 (m, 4H); LCMS: (electrospray +ve), m/z 440.1 (MH)$^+$; HPLC: t$_R$=3.70 min, UV$_{254}$=100%. HRMS (ESI): m/z calcd for C$_{20}$H$_8$N$_5$O$_3$S$_2$ [M+H]$^+$ 440.0845. found 440.0852.

Example 25

2-(3-(2-aminopyrimidin-5-yl)phenyl)-7-(piperazin-1-yl)-5H-[1,3,4]thiadiazolo[3,2-a]pyrimidin-5-one

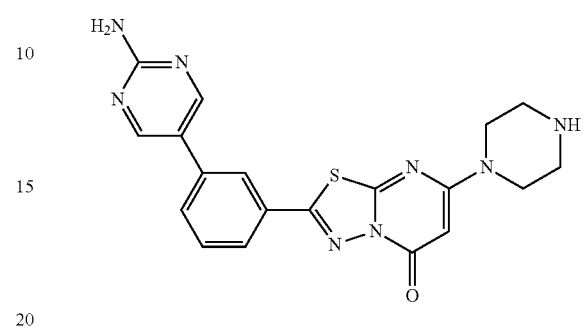

$^1$H NMR (400 MHz, DMSO-d$_6$) δ ppm 8.64 (d, J=2.93 Hz, 2H), 8.00 (d, J=1.17 Hz, 1H), 7.85 (dd, J=9.10, 8.12 Hz, 2H), 7.58-7.68 (m, 1H), 6.87 (s, 2H), 5.39 (d, J=2.54 Hz, 1H), 3.45 (br. s., 4H), 2.71 (d, 4H); LCMS: (electrospray +ve), m/z 407.1 (MH)$^+$; HPLC: t$_R$=3.10 min, UV$_{254}$=100%. HRMS (ESI): m/z calcd for C$_{19}$H$_{19}$N$_8$OS [M+H]$^+$ 407.1389. found 407.1385.

Example 26

2-(4-(3-(5-oxo-7-(piperazin-1-yl)-5H-[1,3,4]thiadiazolo[3,2-a]pyrimidin-2-yl)phenyl)-1H-pyrazol-1-yl)acetic acid

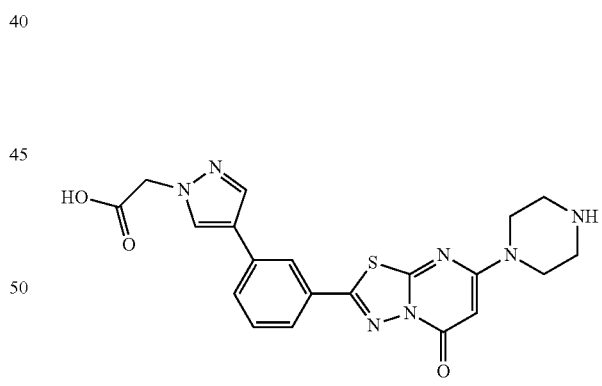

$^1$H NMR (400 MHz, DMSO-d$_6$) δ ppm 13.14 (br. s., 1H), 8.79 (br. s., 1H), 8.33 (d, J=0.78 Hz, 1H), 7.96-8.05 (m, 2H), 7.81-7.89 (m, 1H), 7.70-7.77 (m, 1H), 7.58 (t, J=8.02 Hz, 1H), 5.60 (s, 1H), 4.97 (s, 2H), 3.70-3.82 (m, 4H), 3.16 (br. s., 4H); LCMS: (electrospray +ve), m/z 438.1 (MH)$^+$; HPLC: t$_R$=3.34 min, UV$_{254}$=100%. HRMS (ESI): m/z calcd for C$_{20}$H$_{20}$N$_7$O$_3$S [M+H]$^+$ 438.1343. found 438.1338.

Examples 27-40 are Prepared Using General Procedures Below

Step 1: tert-butyl 4-(2-(3-aminophenyl)-5-oxo-5H-[1,3,4]thiadiazolo[3,2-a]pyrimidin-7-yl)piperazine-1-carboxylate

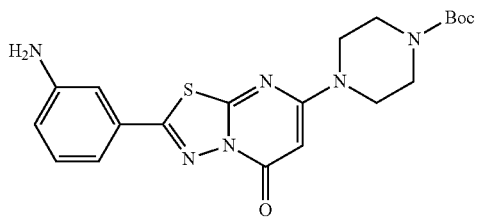 [SMILES: CC(C)(C)OC(=O)N1CCN(c2cc(=O)n3nc(-c4cccc(N)c4)sc3n2)CC1]

tert-butyl 4-(2-(3-nitrophenyl)-5-oxo-5H-[1,3,4]thiadiazolo[3,2-a]pyrimidin-7-yl)piperazine-1-carboxylate (220, 0.480 mmol, 1.0 equiv) is dissolved in 5 mL methanol. To the solution is added palladium on carbon (51.1 mg). The reaction is stirred under an atmosphere of hydrogen for 3 h. Upon completion, the mixture is filtered through celite and concentrated in vacuo to give crude tert-butyl 4-(2-(3-aminophenyl)-5-oxo-5H-[1,3,4]thiadiazolo[3,2-a]pyrimidin-7-yl)piperazine-1-carboxylate as a yellow solid. $^1$H NMR (400 MHz, CHLOROFORM-d) δ ppm 7.37 (s, 1H), 7.20-7.29 (m, 1H), 7.13 (d, J=7.83 Hz, 1H), 6.83 (dd, J=7.63, 1.76 Hz, 1H), 5.46 (s, 1H), 3.87 (s, 2H), 3.45-3.65 (m, 8H), 1.48 (m, 9H);

Step 2

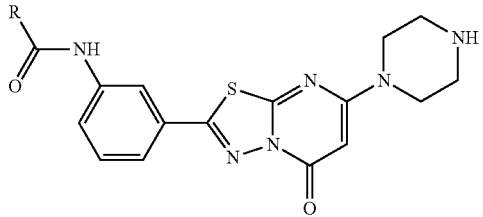

Crude tert-butyl 4-(2-(3-aminophenyl)-5-oxo-5H-[1,3,4]thiadiazolo[3,2-a]pyrimidin-7-yl)piperazine-1-carboxylate (60 mg, 0.140 mmol, 1.0 equiv) prepared as described in step 1 above, is taken up in DMF (1.5 mL) and to it is added the carboxylic acid (0.210 mmol, 1.5 equiv) then EDC (40.3 mg, 0.210 mmol, 1.5 equiv). The mixture is stirred at r.t. for 24 h. Upon completion, the reaction is then taken up in water and ethyl acetate. The layers are separated and the aqueous layer is extracted with ethyl acetate. The combined organic extracts are then washed with water twice, then brine, dried over MgSO$_4$, and concentrated in vacuo to give a yellow solid which is chromatographed with 2-7% MeOH/DCM gradient to give N-acylated tert-butyl 4-(2-(3-aminophenyl)-5-oxo-5H-[1,3,4]thiadiazolo[3,2-a]pyrimidin-7-yl)piperazine-1-carboxylates. The residue is then taken on to the next reaction, which follows the same deprotection procedure to give N-acylated 2-(3-aminophenyl)-7-(piperazin-1-yl)-5H-[1,3,4]thiadiazolo[3,2-a]pyrimidin-5-ones (40-60%) as tan solids after HPLC purification.

Example 27

2-amino-N-(3-(5-oxo-7-(piperazin-1-yl)-5H-[1,3,4]thiadiazolo[3,2-a]pyrimidin-2-yl)phenyl)acetamide

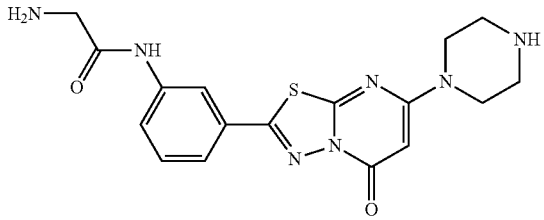 [SMILES: NCC(=O)Nc1cccc(-c2nn3c(=O)cc(N4CCNCC4)nc3s2)c1]

$^1$H NMR (400 MHz, DMSO-d$_6$) δ ppm 8.31 (s, 1H), 7.86 (d, J=7.43 Hz, 1H), 7.48-7.58 (m, 2H), 5.38 (s, 1H), 3.46 (br. s., 4H), 3.29 (s, 2H), 2.67-2.76 (m, 4H); LCMS: (electrospray +ve), m/z 386.1 (MH)$^+$; HPLC: t$_R$=2.70 min, UV$_{254}$=100%. HRMS (ESI): m/z calcd for C$_{17}$H$_{20}$N$_7$O$_2$S [M+H]$^+$ 386.1394. found 386.1393.

In a particular instance, the compound of this example is prepared as described or similarly described as follows: To 5-(3-nitrophenyl)-1,3,4-thiadiazol-2-amine (2) (3.0 g, 13.50 mmol) in MeCN (120 ml) is added methyl 3-chloro-3-oxopropanoate (1.735 mL, 16.20 mmol). The mixture is stirred at room temperature for 2 hours. After consumption of the starting material, POCl$_3$ (60 mL, 644 mmol) is added along with DIPEA (2.358 mL, 13.50 mmol) in MeCN (10 mL). The mixture is heated in the microwave at 150° C. for 25 min, cooled, and concentrated in vacuo. The resulting slurry is taken up in chloroform, poured over ice and washed with saturated NaHCO$_3$, water and brine, dried over MgSO$_4$, and concentrated in vacuo to give a dark red oil which is purified via column chromatography on a 100 g snap column with 0-10% EtOAc/DCM gradient elution to give 7-chloro-2-(3-nitrophenyl)-5H-[1,3,4]thiadiazolo[3,2-a]pyrimidin-5-one (1.36 g, 4.41 mmol, 32.6% yield) as an orange solid.

To 7-chloro-2-(3-nitrophenyl)-5H-[1,3,4]thiadiazolo[3,2-a]pyrimidin-5-one (1.0 g, 3.24 mmol) in MeCN (30 ml) in a microwave vial is added tert-butyl 1-piperazinecarboxylate (0.724 g, 3.89 mmol) followed by DIPEA (1.697 ml, 9.72 mmol). The mixture is heated in the microwave to 150° C. for 25 min., cooled and concentrated in vacuo and purified via column chromatography on a 50 g snap column with 0-10% MeOH/DCM gradient elution to give tert-butyl 4-(2-(3-nitrophenyl)-5-oxo-5H-[1,3,4]thiadiazolo[3,2-a]pyrimidin-7-yl)piperazine-1-carboxylate (1.44 g, 3.14 mmol, 97% yield) as a tan solid.

To a solution of tert-butyl 4-(2-(3-nitrophenyl)-5-oxo-5H-[1,3,4]thiadiazolo[3,2-a]pyrimidin-7-yl)piperazine-1-carboxylate (769 mg, 1.677 mmol) in EtOH (12 ml) at room temperature is added Raney® 2400 nickel (98 mg, 1.677 mmol) followed by hydrazine (0.526 ml, 16.77 mmol) dropwise and the mixture is stirred at room temperature for 4 hours. The reaction is monitored by TLC and LMCMS and additional nickel and hydrazine is added until completion. The mixture is filtered over celite and concentrated in vacuo to give crude tert-butyl 4-(2-(3-aminophenyl)-5-oxo-5H-[1,3,4]thiadiazolo[3,2-a]pyrimidin-7-yl)piperazine-1-carboxylate (443 mg, 1.034 mmol, 61.6% yield) as a tan solid.

Crude tert-butyl 4-(2-(3-aminophenyl)-5-oxo-5H-[1,3,4]thiadiazolo[3,2-a]pyrimidin-7-yl)piperazine-1-carboxylate (60 mg, 0.140 mmol) is taken up in DMF (1.5 mL) and to it is added the Boc-glycine (37 mg, 0.210 mmol) then EDC (40.3 mg, 0.210 mmol). The mixture is stirred at room temperature for 24 hours and the reaction mixture is then taken up in water and ethyl acetate. The layers are separated and the aqueous layer is extracted with ethyl acetate. The combined organic extracts are then washed with water twice, then brine, dried over MgSO₄, and concentrated in vacuo to give a yellow solid which is purified via column chromatography with 2-7% MeOH/DCM gradient to give tert-butyl 4-(2-(3-(2-(tert-butoxycarbonylamino)acetamido)phenyl)-5-oxo-5H-[1,3,4]thiadiazolo[3,2-a]pyrimidin-7-yl)piperazine-1-carboxylate (crude material confirmed by LCMS analysis). The residue is then taken up in 2 mL of dichloromethane and trifluoroacetic acid (1 ml, 13.0 mmol) is added and the mixture is stirred for 18 hours. The solution is then concentrated in vacuo and washed with dichloroethane to give a crude yellow solid that is dissolved in methanol and purified by preparative HPLC to give 2-amino-N-(3-(5-oxo-7-(piperazin-1-yl)-5H-[1,3,4]thiadiazolo[3,2-a]pyrimidin-2-yl)phenyl)acetamide (40 mg, 49%) as a tan solid after HPLC purification.

Example 28

6-fluoro-N-(3-(5-oxo-7-(piperazin-1-yl)-5H-[1,3,4]thiadiazolo[3,2-a]pyrimidin-2-yl)phenyl)nicotinamide Example 29

3-amino-N-(3-(5-oxo-7-(piperazin-1-yl)-5H-[1,3,4]thiadiazolo[3,2-a]pyrimidin-2-yl)phenyl)propanamide

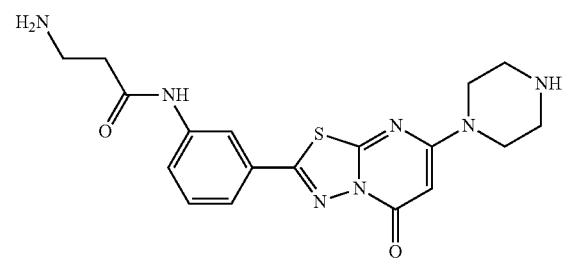

$^1$H NMR (400 MHz, DMSO-d$_6$) δ ppm 8.26 (d, J=1.57 Hz, 1H), 7.77 (dt, J=6.41, 2.47 Hz, 1H), 7.46-7.54 (m, 2H), 5.37 (s, 1H), 3.40-3.49 (m, 4H), 2.82 (t, J=6.46 Hz, 2H), 2.65-2.74 (m, 4H), 2.39 (t, 2H); LCMS: (electrospray +ve), m/z 400.1 (MH)$^+$; HPLC: t$_R$=3.27 min, UV$_{254}$=100%. HRMS (ESI): m/z calcd for C$_{18}$H$_{22}$N$_7$O$_2$S [M+H]$^+$ 400.1549. found 400.1546.

Example 30

N-(3-(5-oxo-7-(piperazin-1-yl)-5H-[1,3,4]thiadiazolo[3,2-a]pyrimidin-2-yl)phenyl)piperidine-4-carboxamide

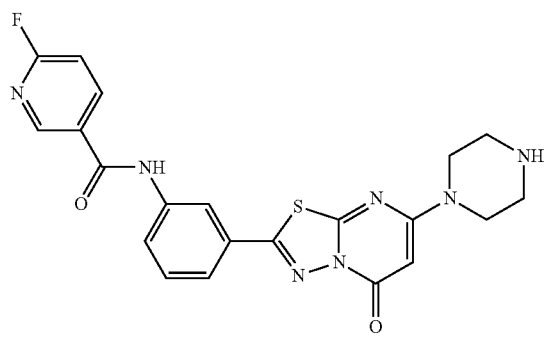 [SMILES: O=C(Nc1cccc(-c2nn3c(=O)cc(N4CCNCC4)nc3s2)c1)c1ccc(F)nc1]

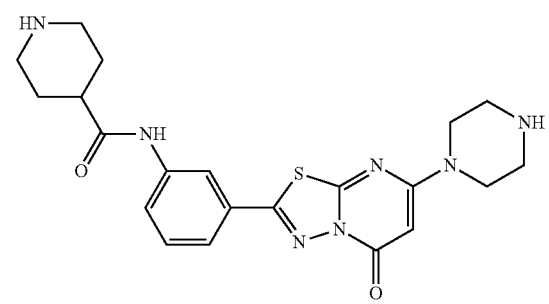 [SMILES: O=C(Nc1cccc(-c2nn3c(=O)cc(N4CCNCC4)nc3s2)c1)C1CCNCC1]

$^1$H NMR (400 MHz, DMSO-d$_6$) δ ppm 10.72 (s, 1H), 8.84 (d, J=2.74 Hz, 1H), 8.52 (td, J=8.12, 2.54 Hz, 1H), 8.40 (s, 1H), 8.04 (dt, J=7.43, 1.96 Hz, 1H), 7.52-7.65 (m, 2H), 7.37 (dd, J=8.61, 2.35 Hz, 1H), 5.38 (s, 1H), 3.40-3.49 (m, 4H), 2.65-2.76 (m, 4H); LCMS: (electrospray +ve), m/z 452.1 (MH)$^+$; HPLC: t$_R$=3.65 min, UV$_{254}$=100%. HRMS (ESI): m/z calcd for C$_{18}$H$_{28}$FN$_7$O$_2$S [M+H]$^+$ 452.1300. found 452.1305.

$^1$H NMR (400 MHz, DMSO-d$_6$) δ ppm 10.12 (s, 1H), 8.27 (s, 1H), 7.79 (d, J=7.04 Hz, 1H), 7.49 (s, 2H), 5.37 (s, 1H), 3.44 (br. s., 4H), 2.93 (br. s., 2H), 2.70 (br. s., 4H), 2.40 (m, 2H), 1.65 (br. s., 2H), 1.50 (br. s., 2H); LCMS: (electrospray +ve), m/z 440.2 (MH)$^+$; HPLC: t$_R$=2.90 min, UV$_{254}$=100%. HRMS (ESI): m/z calcd for C$_{21}$H$_{26}$N$_7$O$_2$S [M+H]$^+$ 440.1862. found 440.1860.

Example 31

(R)-4-amino-5-oxo-5-(3-(5-oxo-7-(piperazin-1-yl)-5H-[1,3,4]thiadiazolo[3,2-a]pyrimidin-2-yl)phenylamino)pentanoic acid

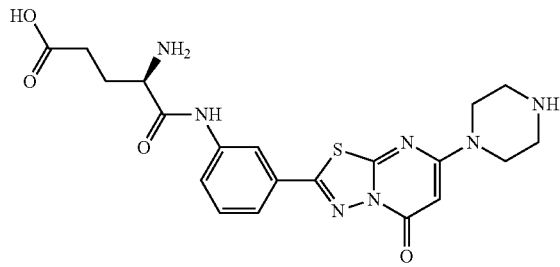 [SMILES: N[C@H](CCC(=O)O)C(=O)Nc1cccc(-c2nn3c(=O)cc(N4CCNCC4)nc3s2)c1]

$^1$H NMR (400 MHz, DMSO-d$_6$) δ ppm 8.26 (t, J=1.76 Hz, 1H), 7.83 (ddd, J=7.97, 1.81, 1.57 Hz, 1H), 7.52-7.67 (m, 2H), 5.57 (s, 1H), 3.95 (t, J=6.46 Hz, 1H), 3.70-3.81 (m, 4H), 3.09-3.18 (m, 4H), 2.32-2.42 (m, 2H), 2.01-2.11 (m, 2H); LCMS: (electrospray +ve), m/z 458.2 (MH)$^+$; HPLC: t$_R$=2.66 min, UV$_{254}$=100%. HRMS (ESI): m/z calcd for C$_{20}$H$_{24}$N$_7$O$_4$S [M+H]$^+$ 458.1605. found 458.1602.

Example 32

(S)-2-amino-N-(3-(5-oxo-7-(piperazin-1-yl)-5H-[1,3,4]thiadiazolo[3,2-a]pyrimidin-2-yl)phenyl)-3-(thiazol-4-yl)propanamide

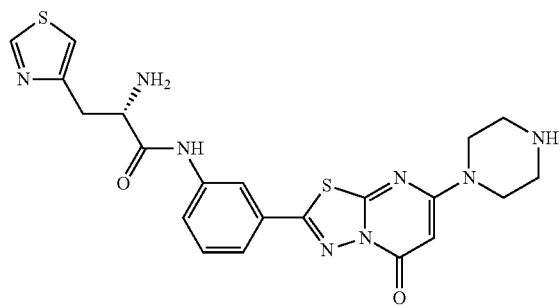 [SMILES: N[C@@H](Cc1cscn1)C(=O)Nc1cccc(-c2nn3c(=O)cc(N4CCNCC4)nc3s2)c1]

$^1$H NMR (400 MHz, DMSO-d$_6$) δ ppm 10.79 (s, 1H), 9.10 (d, J=1.96 Hz, 1H), 8.86 (br. s., 1H), 8.33 (br. s., 2H), 8.22 (t, J=1.76 Hz, 1H), 7.76 (ddd, J=8.07, 1.71, 1.37 Hz, 1H), 7.53-7.63 (m, 1H), 7.51 (d, J=1.96 Hz, 1H), 5.57 (s, 1H), 4.29 (br. s., 1H), 3.70-3.81 (m, 4H), 3.34-3.45 (m, 2H), 3.10-3.20 (m, 4H); LCMS: (electrospray +ve), m/z 483.0 (MH)$^+$; HPLC: t$_R$=3.00 min, UV$_{254}$=100%. HRMS (ESI): m/z calcd for C$_{21}$H$_{23}$N$_8$O$_2$S$_2$ [M+H]$^+$ 483.1379. found 483.1376.

Example 33

(S)-2-amino-N-(3-(5-oxo-7-(piperazin-1-yl)-5H-[1,3,4]thiadiazolo[3,2-a]pyrimidin-2-yl)phenyl)propanamide

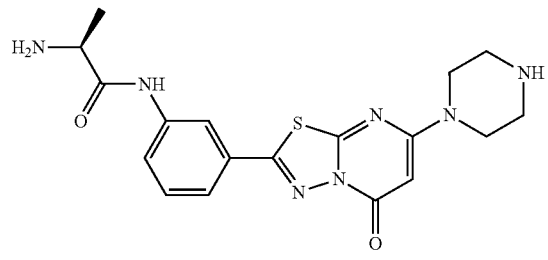 [SMILES: C[C@H](N)C(=O)Nc1cccc(-c2nn3c(=O)cc(N4CCNCC4)nc3s2)c1]

$^1$H NMR (400 MHz, DMSO-d$_6$) δ ppm 10.71 (s, 1H), 8.83 (br. s., 1H), 8.26 (t, J=1.66 Hz, 1H), 8.14-8.23 (m, 2H), 7.82 (ddd, J=7.87, 1.81, 1.66 Hz, 1H), 7.53-7.66 (m, 2H), 5.57 (s, 1H), 4.01 (br. s., 1H), 3.71-3.80 (m, 4H), 3.16 (br. s., 4H), 1.46 (d, 3H); LCMS: (electrospray +ve), m/z 400.2 (MH)$^+$; HPLC: t$_R$=2.79 min, UV$_{254}$=100%. HRMS (ESI): m/z calcd for C$_{18}$H$_{22}$N$_7$O$_2$S [M+H]$^+$ 400.1550. found 400.1545.

Example 34

(R)-2-amino-N-(3-(5-oxo-7-(piperazin-1-yl)-5H-[1,3,4]thiadiazolo[3,2-a]pyrimidin-2-yl)phenyl)propanamide

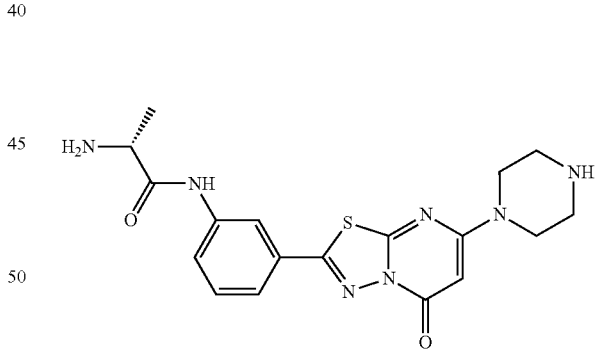

$^1$H NMR (400 MHz, DMSO-d$_6$) δ ppm 10.71 (s, 1H), 8.83 (br. s., 1H), 8.26 (t, J=1.66 Hz, 1H), 8.13-8.23 (m, 2H), 7.82 (ddd, J=7.87, 1.81, 1.66 Hz, 1H), 7.52-7.67 (m, 2H), 5.57 (s, 1H), 4.01 (br. s., 1H), 3.70-3.81 (m, 4H), 3.16 (br. s., 4H), 1.46 (d, 3H); LCMS: (electrospray +ve), m/z 400.2 (MH)$^+$; HPLC: t$_R$=2.82 min, UV$_{254}$=100%. HRMS (ESI): m/z calcd for C$_{18}$H$_{22}$N$_7$O$_2$S [M+H]$^+$ 400.1550. found 400.1547.

Example 35

(R)-2-amino-N-(3-(5-oxo-7-(piperazin-1-yl)-5H-[1,3,4]thiadiazolo[3,2-a]pyrimidin-2-yl)phenyl)-3-(thiazol-4-yl)propanamide

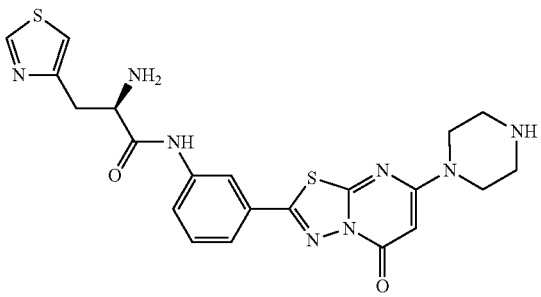 [SMILES: N[C@H](Cc1cscn1)C(=O)Nc1cccc(-c2nn3c(=O)cc(N4CCNCC4)nc3s2)c1]

$^1$H NMR (400 MHz, DMSO-d$_6$) δ ppm 10.79 (s, 1H), 9.10 (d, J=1.96 Hz, 1H), 8.86 (br. s., 1H), 8.33 (br. s., 2H), 8.22 (t, J=1.76 Hz, 1H), 7.76 (ddd, J=8.07, 1.71, 1.37 Hz, 1H), 7.53-7.63 (m, 1H), 7.51 (d, J=1.96 Hz, 1H), 5.57 (s, 1H), 4.29 (br. s., 1H), 3.70-3.81 (m, 4H), 3.34-3.45 (m, 2H), 3.10-3.20 (m, 4H); LCMS: (electrospray +ve), m/z 483.2 (MH)$^+$; HPLC: t$_R$=3.02 min, UV$_{254}$=100%. HRMS (ESI): m/z calcd for C$_{21}$H$_{23}$N$_8$O$_2$S$_2$ [M+H]$^+$ 483.1380. found 483.1381.

Example 36

(R)-2-amino-5-oxo-5-(3-(5-oxo-7-(piperazin-1-yl)-5H-[1,3,4]thiadiazolo[3,2-a]pyrimidin-2-yl)phenylamino)pentanoic acid

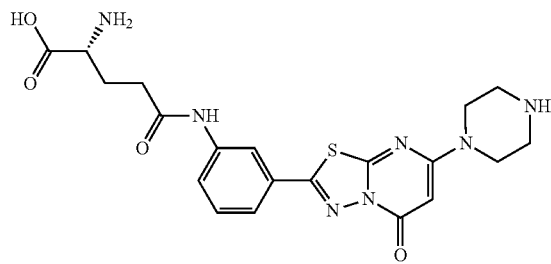 [SMILES: N[C@H](CCC(=O)Nc1cccc(-c2nn3c(=O)cc(N4CCNCC4)nc3s2)c1)C(=O)O]

$^1$H NMR (400 MHz, DMSO-d$_6$) δ ppm 10.44 (s, 1H), 8.33 (s, 1H), 7.71-7.80 (m, 1H), 7.45-7.56 (m, 2H), 5.57 (s, 1H), 3.74 (br. s., 4H), 3.14 (d, J=4.70 Hz, 4H), 2.55 (m, 1H), 2.50 (s, 2H), 2.03 (br. s., 2H); LCMS: (electrospray +ve), m/z 458.2 (MH)$^+$; HPLC: t$_R$=2.82 min, UV$_{254}$=100%. HRMS (ESI): m/z calcd for C$_{20}$H$_{24}$N$_7$O$_4$S [M+H]$^+$ 458.1603. found 458.1598.

Example 37

(S)-4-amino-5-oxo-5-(3-(5-oxo-7-(piperazin-1-yl)-5H-[1,3,4]thiadiazolo[3,2-a]pyrimidin-2-yl)phenylamino)pentanoic acid

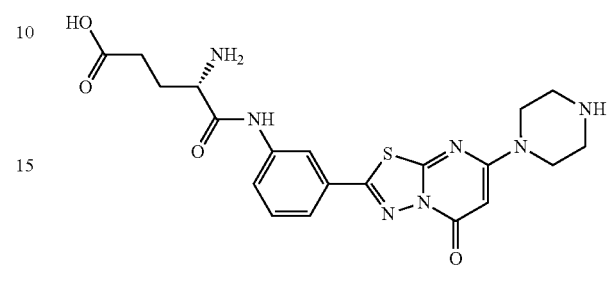

$^1$H NMR (400 MHz, DMSO-d$_6$) δ ppm 8.26 (t, J=1.76 Hz, 1H), 7.83 (ddd, J=7.97, 1.81, 1.57 Hz, 1H), 7.51-7.67 (m, 2H), 5.57 (s, 1H), 3.96 (t, J=6.46 Hz, 1H), 3.70-3.81 (m, 4H), 3.09-3.18 (m, 4H), 2.33-2.42 (m, 2H), 2.01-2.11 (m, 2H); LCMS: (electrospray +ve), m/z 458.2 (MH)$^+$; HPLC: t$_R$=2.78 min, UV$_{254}$=100%. HRMS (ESI): m/z calcd for C$_{20}$H$_{24}$N$_7$O$_4$S [M+H]$^+$ 458.1604. found 458.1620.

Example 38

N-(3-(5-oxo-7-(piperazin-1-yl)-5H-[1,3,4]thiadiazolo[3,2-a]pyrimidin-2-yl)phenyl)isoxazole-3-carboxamide

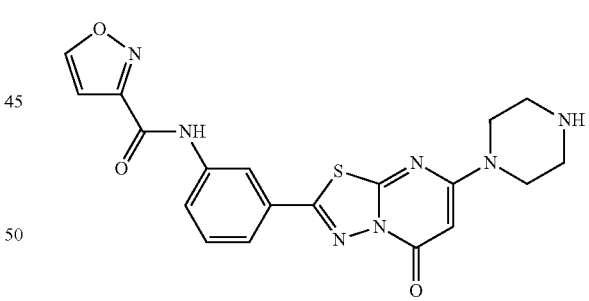

$^1$H NMR (400 MHz, DMSO-d$_6$) δ ppm 11.03 (s, 1H), 9.16 (d, J=1.76 Hz, 1H), 8.72 (br. s., 1H), 8.48 (t, J=1.86 Hz, 1H), 8.02 (ddd, J=8.07, 2.10, 1.17 Hz, 1H), 7.63-7.70 (m, 1H), 7.59 (t, J=8.02 Hz, 1H), 7.02 (d, J=1.76 Hz, 1H), 5.58 (s, 1H), 3.70-3.79 (m, 4H), 3.10-3.19 (m, 4H); LCMS: (electrospray +ve), m/z 424.1 (MH)$^+$; HPLC: t$_R$=3.54 min, UV$_{254}$=100%. HRMS (ESI): m/z calcd for C$_{19}$H$_{18}$N$_7$O$_3$S [M+H]$^+$ 424.1186. found 424.1181.

Example 39

2-(methylamino)-N-(3-(5-oxo-7-(piperazin-1-yl)-5H-[1,3,4]thiadiazolo[3,2-a]pyrimidin-2-yl)phenyl)acetamide

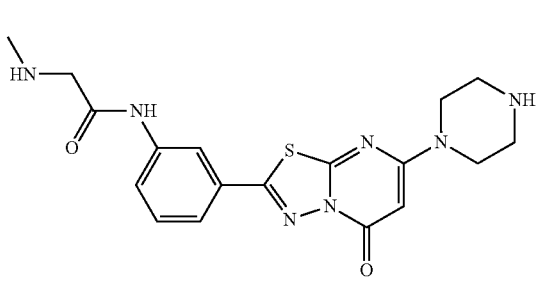 [SMILES: CNCC(=O)Nc1cccc(-c2nn3c(=O)cc(N4CCNCC4)nc3s2)c1]

$^1$H NMR (400 MHz, DMSO-d$_6$) δ ppm 8.27 (t, J=1.66 Hz, 1H), 7.78 (ddd, J=7.68, 1.91, 1.76 Hz, 1H), 7.53-7.64 (m, 2H), 5.57 (s, 1H), 3.94 (s, 2H), 3.70-3.79 (m, 4H), 3.10-3.20 (m, 4H), 2.63 (s, 3H); LCMS: (electrospray +ve), m/z 400.2 (MH)$^+$; HPLC: t$_R$=2.74 min, UV$_{254}$=100%. HRMS (ESI): m/z calcd for C$_{18}$H$_{22}$N$_7$O$_2$S [M+H]$^+$ 400.1557. found 400.1547.

Example 40

N-(3-(5-oxo-7-(piperazin-1-yl)-5H-[1,3,4]thiadiazolo[3,2-a]pyrimidin-2-yl)phenyl)isonicotinamide

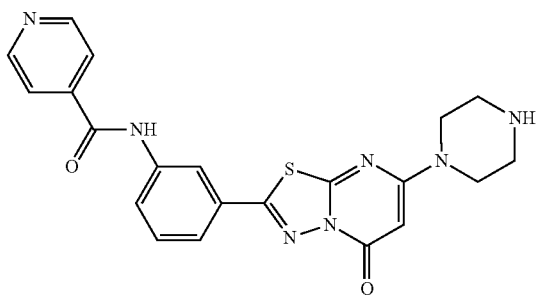 [SMILES: O=C(Nc1cccc(-c2nn3c(=O)cc(N4CCNCC4)nc3s2)c1)c1ccncc1]

$^1$H NMR (400 MHz, DMSO-d$_6$) δ ppm 10.77 (s, 1H), 8.75-8.82 (m, 2H), 8.42 (s, 1H), 8.02-8.10 (m, 1H), 7.86-7.91 (m, 2H), 7.54-7.67 (m, 2H), 5.38 (s, 1H), 3.40-3.50 (m, 4H), 2.67-2.75 (m, 4H); LCMS: (electrospray +ve), m/z 434.1 (MH)$^+$; HPLC: t$_R$=3.08 min, UV$_{254}$=100%. HRMS (ESI): m/z calcd for C$_{21}$H$_{20}$N$_7$O$_2$S [M+H]$^+$ 434.1399. found 434.1393.

Example 41

2-(3-(5-oxo-7-(piperazin-1-yl)-5H-[1,3,4]thiadiazolo[3,2-a]pyrimidin-2-yl)phenylamino)acetic acid

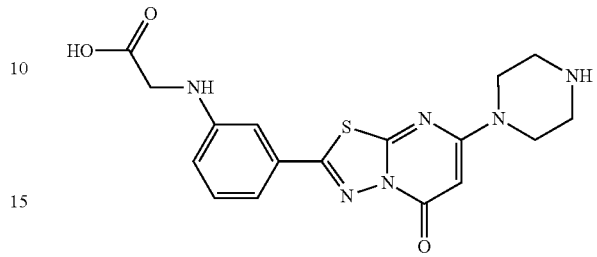

To a solution of tert-butyl 4-(2-(3-aminophenyl)-5-oxo-5H-[1,3,4]thiadiazolo[3,2-a]pyrimidin-7-yl)piperazine-1-carboxylate (50 mg, 0.117 mmol, 1.0 equiv) in 1.0 mL tetrahydrofuran is added dropwise a solution of tert-butyl bromoacetate (0.069 mL, 0.467 mmol, 4.0 equiv) in 0.5 mL tetrahydrofuran and a solution of N,N-diisopropylethylamine (0.082 mL, 0.467 mmol, 4.0 equiv) in 0.5 mL tetrahydrofuran. The mixture is heated in a microwave reactor for 30 min at 120° C. Upon completion, the mixture is taken up in water and EtOAc. The layers are separated and the aqueous layer is back-extracted with EtOAc. The combined organic extracts are washed with water and brine, and concentrated in vacuo to give crude tert-butyl 4-(2-(3-(2-tert-butoxy-2-oxoethylamino)phenyl)-5-oxo-5H-[1,3,4]thiadiazolo[3,2-a]pyrimidin-7-yl)piperazine-1-carboxylate as a yellow solid. The residue is then taken on crude to the next reaction, which followed the same deprotection procedure as above to give 2-(3-(5-oxo-7-(piperazin-1-yl)-5H-[1,3,4]thiadiazolo[3,2-a]pyrimidin-2-yl)phenylamino)acetic acid (18 mg, 40%) as a tan solid.

Example 42

2-(3-(5-oxo-7-(piperazin-1-yl)-5H-[1,3,4]thiadiazolo[3,2-a]pyrimidin-2-yl)benzamido)acetic acid

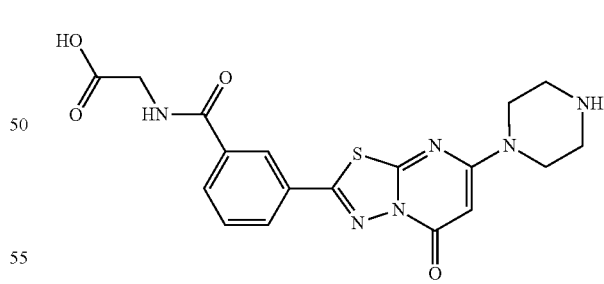

3-(7-(4-(tert-butoxycarbonyl)piperazin-1-yl)-5-oxo-5H-[1,3,4]thiadiazolo[3,2-a]pyrimidin-2-yl)benzoic acid (45 mg, 0.098 mmol, 1.0 equiv), is prepared using the procedure similarly described in Example 7, is dissolved in 1 mL in dimethylformamide. To the solution is added glycine tert-butyl ester (0.016 ml, 0.118 mmol, 1.2 equiv), PyBOP (77 mg, 0.148 mmol, 1.5 equiv), then N,N-diisopropylamine (0.052 ml, 0.295 mmol, 3.0 equiv). The mixture stirred at room temperature for 18 h. Upon completion, the mixture is taken up in water and EtOAc. The layers are separated and the aqueous layer is back-extracted with EtOAc. The combined organic extracts are then washed with water twice, then brine, dried (MgSO$_4$) and concentrated in vacuo to give a yellow oil which is purified by chromatography (silica gel, 2-5% MeOH/dichloromethane) to give tert-butyl 4-(2-(3-(2-tert-butoxy-2-oxoethylcarbamoyl)phenyl)-5-oxo-5H-[1,3,4]thiadiazolo[3,2-a]pyrimidin-7-yl)piperazine-1-carboxylate (41 mg, 73.0% yield) as a yellow oil. The residue is then taken on to the next reaction, which follows the same deprotection procedure as above to give 2-(3-(5-oxo-7-(piperazin-1-yl)-5H-[1,3,4]thiadiazolo[3,2-a]pyrimidin-2-yl)benzamido)acetic acid (16 mg, 53.7% yield) as a white solid.

Example 43

7-(piperazin-1-yl)-2-(3-(pyridin-4-ylmethylamino)phenyl)-5H-[1,3,4]thiadiazolo[3,2-a]pyrimidin-5-one

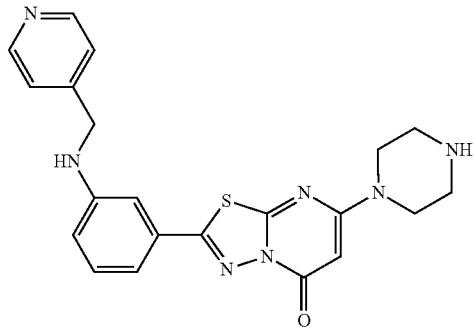 [SMILES: O=c1cc(N2CCNCC2)nc2sc(-c3cccc(NCc4ccncc4)c3)nn12]

To a solution of tert-butyl 4-(2-(3-aminophenyl)-5-oxo-5H-[1,3,4]thiadiazolo[3,2-a]pyrimidin-7-yl)piperazine-1-carboxylate (60 mg, 0.140 mmol, 1.0 equiv) and 4-pyridinecarboxaldehyde (0.013 mL, 0.140 mmol, 1.0 equiv) in 1 mL tetrahydrofuran in a microwave vial is added dibutyltin dichloride (4.25 mg, 0.014 mmol, 0.1 equiv) and Phenylsilane (0.035 mL, 0.280 mmol, 2.0 equiv). The mixture is heated in a microwave reactor for 10 min at 100° C. Upon completion, the reaction mixture is filtered through a thiol-SPE column (Stratospheres) and concentrated in vacuo to give crude tert-butyl 4-(5-oxo-2-(3-(pyridin-4-ylmethylamino)phenyl)-5H-[1,3,4]thiadiazolo[3,2-a]pyrimidin-7-yl)piperazine-1-carboxylate as a yellow oil. The residue is then taken on crude to the next reaction, which followed the same procedure as above to give 7-(piperazin-1-yl)-2-(3-(pyridin-4-ylmethylamino)phenyl)-5H-[1,3,4]thiadiazolo[3,2-a]pyrimidin-5-one (10 mg, 18%) as a white solid.

Example 44

Platelet Adhesion and/or Aggregation

The platelet adhesion assay is conducted by a modification of the assay as described in Blue et al., Blood 2008, 111, 1248, the contents of which are incorporated by reference in their entirety. Thirty microliters of human fibrinogen (50 μg/mL) in Tris/saline (100 mM NaCl, 50 mM Tris/HCl, pH 7.4; American Diagnostica, Stamford, Conn.) are added to black, clear-bottom, untreated polystyrene, nonsterile 384-well microtiter plate wells (Corning no. 3711; Acton, Mass.). After incubating at 22° C. for 1 hour, plates are washed 3 times with Tris/saline, and wells are then blocked with HBMT (138 mM NaCl, 12 mM NaHCO$_3$, 10 mM HEPES, 2.7 mM KCl, 0.4 mM NaH$_2$PO$_4$, 0.1% glucose, 0.35% BSA, pH 7.4) for at least 1 hour. An additional wash is performed using HBMT with 1 mM MgCl$_2$ and 2 mM CaCl$_2$. Calcein-labeled platelets (final concentration 1×10$^{11}$/L) are treated with selected Compounds of the Invention (final concentration of 100 μM, 30 μM, 10 μM or 1 μM) at 22° C. for 20 minutes. Thirty microliters of platelets are then added to the wells. After 1 hour of adhesion, wells are washed 3 times with HBMT-1 mM MgCl$_2$/2 mM CaCl$_2$ and the plates are read by a fluorescent microtiter plate reader (Envision; Perkin Elmer) to detect calcein fluorescence (490 nm excitation and 515 nm emission). Negative controls consist of wells containing platelets without compounds of the invention. Positive controls are wells containing platelets and known inhibitors of αIIbβ3, including mAbs 7E3 and 10E5, and EDTA.

The platelet aggregation assay is conducted by modification of the assay as disclosed in Blue et al., Blood 2008, 11, 1248, the contents of which are incorporated by reference in their entirety. Citrated platelet-rich plasma (PRP), generated by the centrifugation of whole blood at 650 g for 4 minutes at 22° C., is incubated in aggregometer cuvettes with selected Compounds of the Invention (final concentration of 100 μM, 30 μM, 10 μM or 1 μM) or controls for 15 minutes at 37'C. After 30 seconds in the aggregometer (Kowa AF-10E; Tokyo, Japan) at 37° C. with stirring, ADP (5-20 μM) is added to induce aggregation and the light transmittance is measured for 8 minutes. The initial slopes of aggregation in the presence of different concentrations of the Compound being tested are used to generate an IC$_{50}$.

Platelet adhesion and/or aggregation studies of various Compounds of the Invention show that various exemplified compounds of the invention exhibit an IC$_{50}$ value of less than 100 μM in a platelet aggregation study and/or inhibition of greater than 20%, in some instances, greater than 30% at a concentration of 100 μM in a platelet adhesion study. Selected results are shown in Table 1 below:

TABLE 1

18-22

| # | R$_1$ | P.Ad.A.[a] % inhibition[d] | P.Ad.A.[a] IC$_{50}$[d] | P.Ag.A.[a] IC$_{50}$[d] |
|---|---|---|---|---|
| 18 | 3-(2-aminoacetamide) | 92%[b] | 1.1 μM | 0.163 μM |
| 19 | 3-((S)-2-aminopropanamide) | 35%[c] | 8.2 μM | 0.916 μM |
| 20 | 3-((R)-2-aminopropanamide) | 69%[c] | >20 μM | 5.9 μM |
| 21 | 3-(2-methylamino)acetamide) | 24%[c] | ND | ND |
| 22 | 3-(piperidine-4-carboxamide) | 64%[c] | >20 μM | 8.6 μM |

[a]P.Ad.A. = platelet adhesion assay. P.Ag.A. = platelet aggregation assay;
[b]% inhibition at 30 μM; [c]% inhibition at 100 μM [d]% inhibition and IC$_{50}$ values were determined utilizing the platelet adhesion assay and platelet aggregation assay as described in Blue et al, Blood 2008, 111, 1248.
ND = not determined.

In 5 separate experiments, Compound #18 described in Table 1 above (or 2-amino-N-(3-(5-oxo-7-(piperazin-1-yl)-5H-[1,3,4]thiadiazolo[3,2-a]pyrimidin-2-yl)phenyl)acetamide of Example 27 of the current invention) produces 83±7% (mean±SD) inhibition of platelet adhesion to fibrinogen at a concentration of 100 µM, 80±13% inhibition at 30 µM, and 66±10% inhibition at 10 µM; the comparable values for 2-ethyl-7-(piperazin-1-yl)-5H-[1,3,4]thiadiazolo-[3,2-a]pyrimidin-5-one (a compound disclosed and claimed in U.S. Ser. No. 12/514,286) at the same concentrations are 70±15%, 38±10%, and 22±8%. For further comparison, tirofiban produces 87±9% inhibition at 10 µM.

Compound #18 described in Table 1 above (or the compound of Example 27 of the current invention) also inhibits ADP-induced platelet aggregation of citrated PRP with an $IC_{50}$ of 90±20 nM (n=4). By comparison, 2-ethyl-7-(piperazin-1-yl)-5H-[1,3,4]thiadiazolo-[3,2-a]pyrimidin-5-one of U.S. Ser. No. 12/514,286 has an $IC_{50}$ of 12 and 18 µM when tested twice under the same conditions. When PPACK is used as the anticoagulant instead of citrate, the $IC_{50}$ for Compound #18 (or Example 27 of the current invention) is nearly 3-fold higher (220 nM; n=4). Therefore, the compound of Example 27 of the current invention is more than one hundred-fold more potent in inhibiting platelet aggregation than 2-ethyl-7-(piperazin-1-yl)-5H-[1,3,4]thiadiazolo-[3,2-a]pyrimidin-5-one of U.S. Ser. No. 12/514,286.

Example 45

The effects of the Compounds of the Invention on platelet adhesion and/or aggregation may be studied as described in the examples below.

Human αIIb and Marine β3 (hαIIb/mβ3) Platelets.

The production of mice transgenic for the hαIIb gene locus may be produced as described in Thorton et al., Blood (2005) 112:1180-1188, the contents of which are incorporated by reference in their entirety. These mice may be crossed with mice homozygous for targeted disruption of the mαIIb gene (Itga2b). The resulting mice are a mixture of C57Bl/6 and SV129 backgrounds. The genotypes of mice containing the hαIIb transgene and homozygous for the targeted disruption of mαIIb may be confirmed by PCR and direct assessment of surface expression of the receptors may be performed on washed platelets prepared from platelet-rich plasma (PRP) as previously in Eslin et al., Blood (2004) 104:3173-3180; Basani et al., Blood (2009) 113:902-910. FITC-conjugated anti-human CD41 (HIP8; eBioscience, San Diego, Calif.) antibody is used to detect hαIIb and phycoerythrin-conjugated anti-mouse CD41 (MWReg30; BD Biosciences, San Jose, Calif.) antibody is used to detect mαIIb.

Murine αIIb and Human β3 (mαIIb/Hβ) Platelets.

Human normal β3 cDNA may be excised from the pcDNA3 mammalian expression vector (a kind gift of Dr. Peter Newman) and ligated into the mouse stem cell virus MigR1 vector containing an internal ribosome entry site (IRES)-green fluorescent protein (GFP) insertion prior to the polyadenylation signal. Virus containing hβ33 cDNA is then generated using Ecopack 2-293 cells (ATCC, Manassas, Va.). Supernatant containing the virus may be collected 72 h after transfection, passed through a 0.45 m filter, and stored at −70° C. until further use.

Fetal liver cell transplantation may be performed as per Zou et al., Blood (2007) 109:3284-3290, with minor modifications. Fetal liver cells are harvested from Itgb3−/− embryos on a mixed C57Bl/6 and 129S6/SVEV background at E14.5-E16.5 and the cell suspension is enriched for CD34+ hematopoietic progenitors using negative selection (EasySep, StemCell Technologies, Vancouver, BC, Canada). Enriched cells may be then cultured overnight in media containing murine stem cell factor (100 ng/ml), murine interleukin 6 (10 ng/ml) and murine interleukin 3 (20 ng/ml; all from PeproTech, Rocky Hill, N.J.). Fetal cell cultures may be infected at 0.5 transducing units (TDU) per cell on two consecutive days with MigR1-β viral supernatant in the presence of stem cell factor, interleukins 3 and 6 (concentrations as above), and hexadimethrine bromide (8 µg/ml; polybrene, Sigma). Infected cells (approximately $1.5-2 \times 10^6$/mouse; approximately 60% expressing GFP and hβ33) may then be injected i.v. into a lethally irradiated WT (i.e., Itgβ3+/+) mouse (900 rads of X-rays in two divided doses, three hours apart). Platelet studies may be performed with blood obtained 5 weeks or more after transplantation.

Platelet Aggregation:

Blood may be drawn via cardiac puncture from anesthetized Sprague Dawley rats (Taconic, Hudson, N.Y.), WT C57Bl/6 mice (Jackson Laboratories, Bar Harbor, Me.), and mice expressing hαIIb/mβ3 and diluted 1:1 with a mixture of 4 parts 0.165 mM NaCl, 0.01 mM HEPES, pH 7.4 containing 2 mM $CaCl_2$ and 1 mM $MgCl_2$. Blood from consenting human volunteers is obtained from a peripheral vein using a 19 gauge needle and anticoagulated with 1:10 vol 3.8% sodium citrate. Platelet-rich plasma (PRP) may be isolated by centrifugation at 22° C. at 350 g for 10 minutes (rats); 250 g for 2.5 minutes (mice); or 650 g for 4 minutes (human). Mouse PRP samples may be adjusted to 400,000 platelets/µl with the buffer used for dilution and human PRP may be adjusted to 300,000 platelets/µl with platelet-poor plasma. Samples of PRP may be either untreated or incubated for 5 minutes at 37° C. with the Compounds of the Invention (100 µM). Platelet aggregation may be induced by adding to PRP adenosine diphosphate (ADP) at 30 µM (rats and WT mice), 20 or 30 µM (hαIIb/mβ3 mice), or 5 µM (humans), and light transmission may be measured over time in an aggregometer (Kowa AG-10E, Tokyo, Japan) with stirring. Percent inhibition may be calculated by comparing the initial slope of untreated samples to the samples treated with the Compounds of the Invention.

Soluble Fibrinogen Binding:

Whole blood from WT mice, mice expressing hαIIb/mβ33, or mice expressing mαIIb/hβ3 on their platelets may be drawn from the retro-bulbar venous plexus into an equal volume of 200 µM PPACK (Calbiochem, Gibbstown, N.J.) in 165 mM NaCl. Samples may be diluted in HEPES-modified Tyrode buffer [HBMT; 138 mM NaCl, 12 mM $NaHCO_3$, 10 mM HEPES (N-2-hydroxyethylpiperazine-N'-2-ethanesulfonic acid), 2.7 mM KCl, 0.4 mM $NaH_2PO_4$, 0.1% glucose, 0.35% BSA, pH 7.4] containing 50 µM PPACK, 2 mM $CaCl_2$, 1 mM $MgCl_2$, and may be left untreated or incubated with the Compounds of the Invention (20 or 100 µM), RGDS (1 mM) or EDTA (10 mM). Alexa488-fibrinogen (WT and hαIIb/mβ3 mice; 200 µg/ml; Invitrogen, Carlsbad, Calif.) or Alexa647-fibrinogen (mαIIb/hβ3 mice) may be added, and samples may be activated with a PAR-4-activating peptide (AYPGKF, 200 µM) and incubated at 37° C. for 30 minutes. Samples may then be diluted 1:10 in HBMT containing $CaCl_2$ and $MgCl_2$ as above and analyzed by flow cytometry. Fibrinogen binding may be calculated from the geometric mean fluorescence intensity of platelets (gated by forward and side scatter for WT and hαIIb/mβ3 mice, and GFP intensity for mαIIb/hβ3 mice). Fibrinogen binding to unactivated samples may be defined as background binding and PAR-4 peptide-induced fibrinogen binding to untreated samples may be used to establish maximal (100%) binding. Studies performed on WT platelets to assess whether the dilution step performed prior to analysis resulted in fibrinogen dissociation demonstrated that samples analyzed immediately after dilution in buffer without or with Alexa488-fibrinogen (to maintain the same fibrinogen concentration) may have similar net geometric mean fluorescent intensities (133 and 124 units, respectively). When analyzed 15 min after dilution, the values may be identical (115 units), representing 86 and 93% of the immediate values.

Ferric Chloride (FeCl$_3$) Carotid Artery Injury Model:

The protocol for FeCl$_3$-induced injury to the carotid artery may be adapted from Yorovoi et al., *Blood* (2003) 102-4006-4013 with minor changes. Four C57BL/6 WT mice, 6 WT mice on a mixed C57BL/6 and SV129 background, and 16 hαIIb/mβ3 mice may be anesthetized by intraperitoneal (i.p.) injection of pentobarbital (80 mg/kg Nembutol; Ovation Pharmaceuticals, Deerfield, Ill.). After 10 min, mice may be injected i.p. with 10 mM one of the Compounds of the Invention (26.5 mg/kg) (n=8) or the vehicle [1% (n=2) or 10% (n=6) dimethyl sulfoxide (DMSO) in 0.165 M NaCl]. The carotid artery may then be isolated by blunt dissection and a Doppler flow probe (Model 0.5VB; Transonic Systems, Ithaca, N.Y.) may be positioned around the vessel. Approximately 25 min after the compound or vehicle control is administered, a 1×2 mm$^2$ piece of filter paper (#1; Whatman International, Maidstone, Kent, UK) soaked in 20% FeCl$_3$ may be placed on the artery for 3 min and then removed. The area may then be flushed with distilled water and blood flow through the artery is monitored for 30 minutes. Arterial flow rate data may be analyzed as both "percent reduction in flow" (calculated as the area above the line of the plot of observed flow rate versus observation time, divided by the product of the initial flow rate and the total observation time) and "time to occlusion" (defined as the time from the application of the FeCl$_3$-soaked filter paper until arterial blood flow became undetectable for at least 10 min).

Carotid arteries from one hαIIb/mβ3 mouse treated with 10% DMSO and one treated with the Compounds of the Invention may be fixed in formaldehyde, cross-sectioned, and stained with hematoxylin and eosin. The sections may be visualized with a 20× objective using an Olympus BX60 microscope (Melville, N.Y.), photographed with a Nikon D5-5M camera, and captured in Adobe Photoshop 6.0.

Laser Microvascular Injury and Intravital Microscopy:

The protocols for laser microvascular injury in blood vessels in the cremaster muscle and intravital microscopic evaluation of subsequent thrombus formation are described in Neyman et al., *Blood* (2008) 112-1104-1108. Briefly, male mice expressing hαIIb/β3 (three in each group) that are anesthetized with pentobarbitol (11 mg/kg; Abbott Laboratories, North Chicago, Ill.) may have their cremaster arterioles (20 to 40 µm) studied using an Olympus BX61 WI microscope (Olympus, Tokyo, Japan or Center Valley, Pa.) with a 40×/0.8 numeric aperture (NA) water-immersion objective lens. Arteriole laser injuries may be done using an SRS NL100 Nitrogen Laser system (Photonic Instruments, St Charles, Ill.) at 65% energy level. Visual confirmation of the extravasation of small amounts of blood cells may be made for each studied blood vessel as an assurance that a consistent injury had been produced. After the surgery to expose the blood vessels is performed, animals may be injected i.p. with 10 mM the Compounds of the Invention or 10% DMSO. Three arterioles may be injured in each mouse. Injuries may be initiated 25-35 min after injection of the Compounds of the Invention or DMSO, and 5 min after the i.v. injection of labeled antibodies that react with murine platelet GPIbβ (DyLight$^{488}$; Emfret Analytics, Eibelstadt, Germany) and fibrin (Alexa$^{647}$) into the cannulated jugular vein. Data may be collected over 2.5 min at 5 frames per second (750 frames per study) and then averaged at each time point.

Results

Platelet Aggregation:

It will be observed that the Compounds of the Invention at 100 µM will dramatically inhibits aggregation of platelets from humans, and mice expressing the hybrid hαIIb/mβ3 receptors, but not WT mice or rats. In a particular experiment, it is actually observed that at doses that nearly completely inhibited platelet aggregation, the compound of Example 27 of the current invention at 1 µM does not inhibit either mouse or rat platelet aggregation induced by ADP. In sharp contrast, this compound essentially completely inhibits the aggregation of platelets from a mouse expressing human αIIb and β3 (hαIIb/mβ3). Therefore, it is shown that the compound of Example 27 of the current invention is selective for αIIbβ3 compared to αVβ3 and is further selective for human αIIbβ3 compared to mouse or rat αIIbβ3.

Soluble Fibrinogen Binding.

Activated platelets from WT mice will bind fibrinogen, and this binding is expected to only minimally be inhibited by various Compounds of the Invention at 20 or 100 µM. Fibrinogen may also bind to activated platelets from mice expressing mαIIb/hβ3 and these receptors are also not expected to be inhibited by various Compounds of the Invention. In sharp contrast, binding of fibrinogen to activated platelets from hαIIb/mβ3 mice is expected to be inhibited at a concentration of 20 µM and at 100 µM by one of the Compounds of the Invention. For comparison EDTA will inhibit the binding of fibrinogen to WT mouse platelets and hαIIb/mβ3 mouse platelets. Thus, the effects of the Compounds of the Invention on fibrinogen binding to WT and hαIIb/mβ3 platelets will parallel its effects on platelet aggregation.

The Compounds of the Invention Will Protect hαIIb/mβ3 Mice, but not WT Mice, Against Occlusive Carotid Artery Thrombi.

The platelet counts and αIIbβ3 expression levels of mice receiving the DMSO vehicle control solutions or the Compounds of the Invention will not differ significantly. All 8 hαIIb/mβ3 mice treated with DMSO (1 or 10%) will have reductions in carotid artery blood flow after FeCl$_3$ injury. The hαIIb/mβ3 mice may be treated with the Compounds of the Invention. These mice will exhibit much less reduction in blood flow and will not develop an occlusive thrombus.

Cross sections of the hαIIb/mβ3 mouse carotid artery after FeCl$_3$ treatment will reveal nearly complete packing of the lumen with platelet-rich thrombus. The deposits of FeCl$_3$ will be visible as golden granules on the luminal side of the blood vessel. The lumen of the mouse carotid artery treated with the Compounds of the Invention will contain regions of loosely packed erythrocytes, which will demonstrate the patency of the artery. Golden FeCl$_3$ granules will also be visible on the luminal side of the blood vessel.

The Compounds of the Invention Will Decrease Thrombus Formation in Response to Microvascular Laser Injury.

Cremaster arteriole injury studies will permit in situ visualization of thrombus development in real time. There will be no difference in thrombus formation in mice that are either untreated or pre-injected with the carrier, 10% DMSO, prior to injury (comparison not shown). Both groups will demonstrate rapid platelet adhesion followed by progressive incorporation of platelets into the thrombi over the first ~20 sec. In addition, after a delay of ~35 sec, both groups will demonstrate progressive incorporation of fibrin into the thrombi. The animals pre-injected with the Compounds of the Invention prior to injury will not develop platelet accumulation or fibrin deposition over a comparable time period.

Example 46

Platelet Adhesion/Aggregation to Collagen; αVβ3-Mediated Cell Adhesion to Vitronectin; and αIIbβ3-Mediated Cell Adhesion to Fibrinogen Washed platelets are prepared as per the primary screening assay, suspended in HBMT containing 1 mM $MgCl_2$ (platelet adhesion to collagen) or 2 mM $CaCl_{2/1}$ mM $MgCl_2$ (platelet adhesion to fibrinogen) and adjusted to a count of $250 \times 10^9$/L. HEK293 cells stably expressing normal human αVβ3 or normal human αIIbβ3 are suspended in HBMT containing either 1 mM $MgCl_2$ (HEK293 cells expressing αVβ3 for adhesion to vitronectin) or 2 mM $CaCl_2$/1 mM $MgCl_2$ (HEK293 cells expressing αIIbβ3 for adhesion to fibrinogen); the cell counts are adjusted to $10^6$/mL. Polystyrene 96-well microtiter plates (Nunc) are coated with either fibrinogen (50 µg/mL), vitronectin (5 µg/mL), or collagen β3 µg/mL, rat tail type 1; Becton Dickinson) for 1 hour, and blocked with HBMT for at least 1 hour. Platelets and cells are treated with the compound of Example 27 of the current invention or 2-ethyl-7-(piperazin-1-yl)-5H-[1,3,4]thiadiazolo-[3,2-a]pyrimidin-5-one of U.S. Ser. No. 12/514,286 in the presence or absence of anti-α2β1 mAb 6F1, anti-αIIbβ3 mAb 10E5, anti-αIIbβ3 mAb 10E5+αVβ3 mAb 7E3, αVβ3-specific mAb LM609, or anti-αVβ3+ αIIbβ3 mAb 7E3, for 15 minutes at 37° C. before being added to the microtiter wells. After adhering for 1 hour at either 22° C. (platelets) or 37° C. (cells), nonadherent platelets or cells are removed by washing 3 times with HBMT containing the same ion composition as the buffer used for adhesion. Adherent platelets or cells are quantified by their endogenous acid phosphatase activity on p-nitrophenyl phosphate (pNPP) as previously described in Law D A, Nannizzi-Alaimo L, Ministri K, et al., Blood (1999) 93:2645-2652, the contents of which are incorporated by reference in their entirety (1 mg/mL in 0.1 M sodium citrate, 0.1% Triton X-100, pH 5.4). In other experiments, 8-chambered glass coverslips (Nunc) are coated with collagen β3 µg/mL) for 1 hour at 22° C. Washed platelets are allowed to adhere for 1 hour at 22° C. and the coverslips are stained with the Alexa-488-conjugated β3-specific mAb $7H_2$. Adherent platelets are imaged using a Zeiss LSM-510 confocal system with Axiovert 200 microscope (Carl Zeiss, Heidelberg, Germany) using a Plan-Apochromat 100/1.4 NA oil DIC objective.

This experiment shows that anti-α2β1 mAb 6F1 produced 95% inhibition of platelet adhesion/aggregation to collagen, whereas the anti-αIIbβ3 mAb 10E5 and the anti-αIIbβ3+ αVβ3 mAb 7E3 produce ~30% inhibition. The compound of Example 27 of the current invention at 1-100 µM also inhibits adhesion/aggregation by about ~30%, and combining the compound of Example 27 of the current invention with the anti-αIIbβ3 antibody 10E5 does not further inhibit adhesion/aggregation. Microscopic analysis indicates that the compound of Example 27 of the current invention does not decrease platelet adhesion to collagen, but rather decreases the recruitment of additional platelets to the adherent platelets.

Further, the αVβ3-specific mAb LM609 inhibits adhesion of HEK293 cells expressing αVβ3 to vitronectin by 74±27% (n=4) at 20 µg/ml and the anti-αVβ3+αIIbβ3 mAb 7E3 inhibits adhesion by 80±12% (n=4) at 40 µg/ml. In sharp contrast, 2-ethyl-7-(piperazin-1-yl)-5H-[1,3,4]thiadiazolo-[3,2-a]pyrimidin-5-one of U.S. Ser. No. 12/514,286 at 100 µM produced only 5±7% (n=4) inhibition and 2-amino-N-(3-(5-oxo-7-(piperazin-1-yl)-5H-[1,3,4]thiadiazolo[3,2-a]pyrimidin-2-yl)phenyl)acetamide at 10 µM produced only 6±15% (n=4). These data are both similar to the 2±9% (n=3) inhibition produced by the αIIbβ3-specific mAb 10E5.

αVβ3-specific mAb LM609 does not inhibit the adhesion of HEK293 cells expressing αIIbβ3 to fibrinogen, whereas 10E5 produces 79±10% inhibition, 7E3 produces 87±9% inhibition, 2-ethyl-7-(piperazin-1-yl)-5H-[1,3,4]thiadiazolo-[3,2-a]pyrimidin-5-one of U.S. Ser. No. 12/514,286 produced 55±5% inhibition, and the compound of Example 27 of the current invention of the current invention produces 65±5% inhibition (all n=4) at the same concentrations indicated for the αVβ3 experiments.

Example 47

Induction of Ligand-Induced Binding Site (LIBS) Epitopes

Washed platelets are prepared in HBMT containing 2 mM $CaCl_2$/1 mM $MgCl_2$. Platelet count is adjusted to $250 \times 10^9$/L and the compound of Example 27 of the current invention (100 µM), 2-ethyl-7-(piperazin-1-yl)-5H-[1,3,4]thiadiazolo-[3,2-a]pyrimidin-5-one (a compound disclosed and claimed in U.S. Ser. No. 12/514,286), eptifibatide (10 µM), EDTA (10 mM), or mAb 10E5 (20 µg/mL) is added to samples (30 µL) and incubated for 15 minutes at 37° C. Fluorescently labeled monoclonal antibodies (PMI-1, LIBS-1, AP5, or 10E5; Alexa-488 conjugated; Invitrogen) are then added (20 µL, final concentration: 5 µg/mL) and incubated for 30 minutes at 22° C. in the dark, after which samples are diluted 1:10 in HBMT with $CaCl_2$/$MgCl_2$ for analysis by flow cytometry (FACSCalibur; Becton Dickinson, Franklin Lakes, N.J.). Antibody binding is reported as the geometric mean fluorescence intensity; nonspecific binding is determined by adding a 50-fold excess of unlabeled antibody before adding the labeled antibody. The net normalized fluorescence intensity in the presence of eptifibatide (10 µM, 30 min incubation at 22° C.) is assigned the value of 100%

This experiment shows that untreated platelets bind 7±3% (n=5) of the amount of AP5 in the presence of eptifibatide. In the presence of 2-ethyl-7-(piperazin-1-yl)-5H-[1,3,4]thiadiazolo-[3,2-a]pyrimidin-5-one of U.S. Ser. No. 12/514,286, platelets bind 10±4% of the amount in the presence of eptifibatide. In the presence of the compound of Example 27 of the current invention, platelets bind 18±5% of the amount in the presence of eptifibatide. The comparable data for LIBS1 binding after 30 min are 22±3% (n=5) for untreated platelets, 18±2% for platelets in the presence of 2-ethyl-7-(piperazin-1-yl)-5H-[1,3,4]thiadiazolo-[3,2-a]pyrimidin-5-one (a compound disclosed and claimed in U.S. Ser. No. 12/514,286), and 21±3% for platelets in the presence of the compound of Example 27 of the current invention. Untreated platelets bind 46±5% (n=4) of the amount of PMI-1 that platelets treated with eptifibatide bound; both 2-ethyl-7-(piperazin-1-yl)-5H-[1,3,4]thiadiazolo-[3,2-a]pyrimidin-5-one of U.S. Ser. No. 12/514,286 and the compound of Example 27 of the current invention increase PMI-1 binding to similar extents (73±9% and 82±13, respectively).

In summary, Examples 46-47 show that the compound of Example 27 of the current invention as well as 2-ethyl-7-(piperazin-1-yl)-5H-[1,3,4]thiadiazolo-[3,2-a]pyrimidin-5-one of U.S. Ser. No. 12/514,286 produce much less exposure than does eptifibatide of the β3 PSI epitope recognized by mAb AP5. The compound of Example 27 of the current invention does, however, produce significantly more exposure than does 2-ethyl-7-(piperazin-1-yl)-5H-[1,3,4]thiadiazolo-[3,2-a]pyrimidin-5-one of U.S. Ser. No. 12/514,286 (18 and 10% of the eptifibatide value, respectively), with untreated platelets binding ~7% of the eptifibatide value. Both 2-ethyl-7-(piperazin-1-yl)-5H-[1,3,4]thiadiazolo-[3,2-a]pyrimidin-5-one of U.S. Ser. No. 12/514,286 and the compound of Example 27 of the current invention induce exposure of the αIIb leg region epitope recognized by PMI-1, although they are less effective than eptifibatide. Thus, both compounds clearly affect the conformation of the αIIb subunit, but have much less effect than eptifibatide, a prototypic RGD-mimetic antagonist, in inducing a conformational change in the β3 subunit.

Example 48

The Effect of the Compound of the Invention on Induction of Extension of Purified αIIbβ3 as Judged by Electron Microscopy Purification of Integrin αIIbβ3:

αIIbβ3 is purified from outdated single donor platelet concentrates obtained from the New York Blood Center by washing platelets in the presence of $PGE_1$; removing contaminating blood cells by centrifugation; lysing the resuspended platelets at 4° C. in 5% (w/v) n-octyl-β-D-glucoside (OG) in 150 mM NaCl, 20 mM HEPES, 1 mM $CaCl_2$, 1 mM $MgCl_2$, 10 µM leupeptin, pH 7.4; performing Con A affinity chromatography [binding buffer: 150 mM NaCl, 1% (w/v) OG, 20 mM HEPES, 1 mM $CaCl_2$, 1 mM $MgCl_2$, pH 7.4; washing buffer: binding buffer+20 mM α-methyl glucoside; elution buffer: binding buffer+1M α-methyl glucoside]; performing heparin affinity chromatography; applying the flow through fraction to Q-Sepharose [binding buffer: 75 mM NaCl, 1% (w/v) OG, 10 mM HEPES, 1 mM $CaCl_2$, 1 mM $MgCl_2$, pH 7.4; washing buffer: binding buffer+200 mM NaCl; elution buffer: binding buffer+400 mM NaCl]; and performing gel size exclusion chromatography on Sephacryl S300 HR [running buffer: 150 mM NaCl, 1% (w/v) OG, 10 mM HEPES, 1 mM $CaCl_2$, 1 mM $MgCl_2$, pH 7.4].

Preparation of αIIbβ3-Containing Nanodiscs:

αIIbβ3-containing nanodiscs are prepared by a modification of the techniques described by Ritchie et al., Babyurt and Sligar, and Ye et al[2-4], the contents of which are incorporated by reference in their entirety. In brief, the His-tagged membrane scaffold protein is prepared as a recombinant protein in *E. coli* and purified by Nickel affinity chromatography and anion exchange chromatography. Final assembly consists of solubilizing an equimolar mixture of 1,2-dimyristoyl-sn-glycero-3-phosphocholine and 1,2-dimyristoyl-sn-glycero-3-phospho-(1'-rac-glycerol) in octylglucoside and cholate and then adding the purified αIIbβ3. The detergents are removed with macroporous polymeric beads (Bio-Bead SM-2) and then the αIIbβ3 nanodiscs are separated from the empty nanodiscs by gel filtration.

Negative Staining Electron Microscopy and Evaluation of αIIbβ3 Nanodisc Particle Size:

αIIbβ3 nanodiscs are treated with eptifibatide, tirofiban, 2-ethyl-7-(piperazin-1-yl)-5H-[1,3,4]thiadiazolo-[3,2-a]pyrimidin-5-one of U.S. Ser. No. 12/514,286, or the compound of Example 27 of the current invention for 1 hour at room temperature at concentrations up to 100 µM for 2-ethyl-7-(piperazin-1-yl)-5H-[1,3,4]thiadiazolo-[3,2-a]pyrimidin-5-one (a compound claimed in U.S. Ser. No. 12/514,286) and at concentrations up to 10 µM for 2-amino-N-(3-(5-oxo-7-(piperazin-1-yl)-5H-[1,3,4]thiadiazolo[3,2-a]pyrimidin-2-yl)phenyl)acetamide of Example 27. Samples are loaded onto carbon-coated copper grids that are glow-discharged by a carbon coating unit (Edwards; Crowley, UK), and then stained with 2% uranyl acetate, followed by drying. Imaging of αIIbβ3 nanodiscs is performed using a JOEL JEM 100CX transmission electron microscope (Jeol Ltd; Tokyo, Japan) at 80 kV and magnifications of 33,000× and 50,000×. Individual nanodiscs containing αIIbβ3 are manually selected for analysis using Image J (NIH, Bethesda, Md.). The distance from the bottom of the nanodisc to the height of the αIIbβ3 complex (nanodisc-integrin length; NIL) is measured as an indicator of integrin extension. The frequency distribution of NIL values is then analyzed for untreated αIIbβ3 nanodiscs and αIIbβ3 nanodiscs in the presence of different compounds.

This experiment shows that in the absence of compound, αIIbβ3 primarily adopts a compact conformation adjacent to the nanodisc, giving nanodisc-integrin length (NIL) values primarily between 11 and 17 nm. Occasional nanodiscs, however, contain αIIbβ3 molecules that are extended, giving NIL values between 18 and 23. As a result, the NIL frequency distribution shows a bimodal pattern, with a marked predominance of αIIbβ3 nanodiscs in the range of 11 to 17 nm, and a small subpopulation in the range 18 to 23 nm. Both eptifibatide and tirofiban shift the distribution in a dose-dependent manner such that at the highest doses the majority of αIIbβ3 nanodiscs has NIL values in the 18 to 23 nm range ($p<0.001$ and $p<0.001$, respectively). In sharp contrast, neither 2-ethyl-7-(piperazin-1-yl)-5H-[1,3,4]thiadiazolo-[3,2-a]pyrimidin-5-one of U.S. Ser. No. 12/514,286 at concentrations up to 100 µM nor the compound of Example 27 of the current invention at concentrations up to 10 µM produce a significant shift in NIL values ($p=0.23$ and $p=0.37$, respectively). In other words, the compound of Example 27 of the current invention and 2-ethyl-7-(piperazin-1-yl)-5H-[1,3,4]thiadiazolo-[3,2-a]pyrimidin-5-one of U.S. Ser. No. 12/514,286 at these concentrations do not induce receptor extension as judged by electron microscopy.

Example 49

The Effect of $Mg^{2+}$ Concentration on Platelet Adhesion to Fibrinogen in the Presence of the Compound of the Invention Washed platelets in buffers containing 1 mM $Ca^{2+}$ plus 1 mM, 20 mM, or 50 mM $Mg^{2+}$ are added to wells pre-coated with fibrinogen (50 g/ml) for 60 min at 22° C. After washing, adherent platelets are detected by acid phosphatase activity. Results are expressed as mean±SD (n=3 for the compound of Example 27 of the current invention and 2-ethyl-7-(piperazin-1-yl)-5H-[1,3,4]thiadiazolo-[3,2-a]pyrimidin-5-one (a compound disclosed and claimed in U.S. Ser. No. 12/514,286); n=2 for tirofiban).

In three separate experiments, the $IC_{50}$ for the compound of Example 27 of the current invention increases from $0.29 \pm 0.1$ μM (mean±SD) at 1 mM $Mg^{2+}$ to $0.91 \pm 0.21$ μM at 20 mM $Mg^{2+}$ (p<0.01), and to $1.3 \pm 0.35$ μM at 50 mM $Mg^{2+}$ (p<0.01). Thus, in going from 1 to 50 mM $Mg^{2+}$, there is an ~4.5-fold increase in $IC_{50}$, corresponding to nearly an ~80% decrease in affinity. Neither 2-ethyl-7-(piperazin-1-yl)-5H-[1,3,4]thiadiazolo-[3,2-a]pyrimidin-5-one of U.S. Ser. No. 12/514,286 nor tirofiban shows a comparable increase in $IC_{50}$ at higher $Mg^{2+}$ concentrations.

Example 50

Effect of $Mg^{2+}$ on Platelet Aggregation Induced by ADP in the Presence of Test Compound Washed platelets are resuspended in buffer containing fibrinogen (200 μg/ml) and 1 mM $Mg^{2+}$ in combination with either 1 mM or 20 mM $Mg^{2+}$. Aggregation is induced by adding a thrombin receptor activating peptide (SFLLRN (SEQ ID NO. 2)) at 10 μM.

The inhibitory effect of the compound of Example 27 of the current invention (1 μM) on platelet aggregation induced by a thrombin receptor activating peptide (SFLLRN (SEQ ID NO. 2)) at different $Mg^{2+}$ concentrations is clearly attenuated at 20 mM $Mg^{2+}$, whereas the effect on 2-ethyl-7-(piperazin-1-yl)-5H-[1,3,4]thiadiazolo-[3,2-a]pyrimidin-5-one of U.S. Ser. No. 12/514,286 (100 μM) is much less evident. This experiment shows that the compound of Example 27 binds by a novel mechanism leading to loss of the MIDAS metal ion while producing only minor changes in the conformation of αIIbβ3.

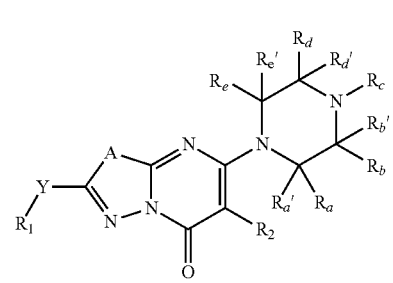

Formula P-I wherein:
i) A is S, N(H), $CH_2$, or O;
ii) $R_1$ is:
  phenyl optionally substituted with one or more nitro, —C(O)N($R_5$)($R_6$) and/or —N($R_5$)($R_6$), and Y is a —$C_1$-$C_4$alkylene or arylene;
  phenyl substituted with one or more nitro and/or —N($R_5$)($R_6$), and Y is a single bond;
  phenyl substituted with —C(O)O$R_3$ and Y is a —$C_1$-$C_4$alkylene or arylene;
  heteroaryl wherein said heteroaryl group is optionally substituted with one or more —$C_1$-$C_4$alkyl, and Y is a single bond or —$C_1$-$C_4$alkylene;
  heteroaryl wherein said heteroaryl group is substituted with halo, —C(O)OH, —$CH_2$C(O)OH, or —$NH_2$, and Y is arylene;
  pyrazolyl, isoxazolyl, furyl or thienyl and Y is arylene wherein said pyrazolyl, isoxazolyl, furyl or thienyl is

What is claimed is:

1. A method for the treatment of a thrombotic disorder comprising administering to a subject having a thrombotic disorder or at risk of thrombotic disorder an effective amount of a compound according to Formula P-I, in free or pharmaceutically acceptable salt form, or a pharmaceutical composition comprising a compound of Formula P-I and a pharmaceutically acceptable diluent or carrier, such that platelet aggregation and/or adhesion is reduced; wherein Formula P-I is:

optionally substituted with one or more —$C_1$-$C_4$alkyl, —$C_{0-4}$alkyl-C(O)OH, —N($R_{13}$)($R_{14}$), or halo; or
—C(O)N($R_4$)($CH_2$)$_{1-4}$—C(O)O$R_3$ and Y is a single bond, —$C_1$-$C_4$alkylene or arylene,
—C(O)N($R_4$)($CH_2$)$_{1-4}$—N($R_{13}$)($R_{14}$) and Y is a single bond, —$C_1$-$C_4$alkylene or arylene;
—N($R_4$)—C(O)-heteroaryl wherein said heteroaryl is optionally substituted with halo and Y is a single bond, —$C_1$-$C_4$alkylene, or arylene;

—N(R₄)—C₁₋₄alkylene-heteroaryl and Y is a single bond, —C₁-C₄alkylene, or arylene;
—N(R₁₀)—C(O)—[C(R₁₁)(R₁₂)]₁₋₄—N(R₁₃)(R₁₄) and Y is a single bond, —C₁-C₄alkylene, or arylene;
—N(R₁₀)—C(O)—C₃₋₁₀heterocycloalkyl and Y is a single bond, —C₁-C₄alkylene or arylene;
—N(R₄)(CH₂)₁₋₄—C(O)OR₄ and Y is C₁-C₄alkylene or arylene;
—N(R₄)C(O)C(H)(NH₂)CH₂CH₂—C(O)OR₃ and Y is arylene;
—N(R₄)C(O)C(H)(NH₂)CH₂-heteroaryl and Y is arylene;
—N(R₄)C(O)C(H)(CH₃)—NH₂ and Y is arylene;
—N(R₄)C(O)CH₂CH₂C(H)(NH₂)—COOH and Y is arylene;
—N(R₄)C(O)—C(H)(NH₂)CH₂CH₂—COOH and Y is arylene; or
—N(R₄)C(O)-heteroaryl (—N(H)C(O)isoxazolyl) and Y is arylene;

iii) R₂ is H, halo or —C₁-C₄alkyl;
iv) R_a, R_a', R_b, R_b', R_c, R_d, R_d', R_e, and R_e' are independently H or C₁-C₄alkyl;
v) R₃, R₄, R₅ and R₆ are independently H or C₁-C₄alkyl;
vi) R₁₀, R₁₁, R₁₂, R₁₃ and R₁₄ are independently H or C₁₋₄alkyl.

2. The method according to claim 1, wherein both platelet aggregation and adhesion are reduced.

3. The method of claim 1, wherein said thrombotic disorders is selected from a group consisting of stroke, myocardial infarction, unstable angina, abrupt closure following angioplasty or stent placement, thrombosis induced by peripheral vascular surgery, peripheral vascular disease or thrombotic disorders resulting from atrial fibrillation or inflammation.

4. The method of claim 1, wherein said thrombotic disorder is thrombosis induced by peripheral vascular surgery.

5. The method of claim 1, wherein said Compound is:

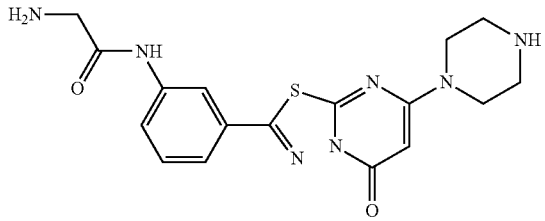

in free or pharmaceutically acceptable salt form.

6. The method of claim 1, further comprising administering to the subject an effective amount of at least one therapeutic agent selected from a group consisting of anticoagulant, antiplatelet, and fibrinolytic agents, in free or pharmaceutically acceptable salt form.

7. The method according to claim 6, wherein said therapeutic agent is selected from a group consisting of heparin, low molecular weight heparins, bivalirudin, Fondaparinux, warfarin, Acenocoumarol, Phenprocoumon, Phenindione, Abbokinase (urokinase), streptokinase, alteplase, retaplase, tenecteplase, prasugrel, aspirin, ticlopidine, clopidogrel, abciximab, eptifibatide and tirofiban.

8. The method of claim 7, wherein said therapeutic agent is heparin.

9. The method of claim 1, wherein
R₁ is
phenyl optionally substituted with one or more nitro or —N(R₅)(R₆) and Y is a —C₁-C₄alkylene or arylene;
phenyl substituted with one or more nitro or —N(R₅)(R₆) and Y is a single bond;
phenyl substituted with —C(O)OR₃ and Y is a —C₁-C₄alkylene or arylene;
heteroaryl wherein said heteroaryl group is optionally substituted with one or more —C₁-C₄alkyl and Y is a single bond, or —C₁-C₄alkylene;
pyrazolyl, isoxazolyl, furyl or thienyl and Y is arylene wherein said pyrazolyl, isoxazolyl, furyl or thienyl is optionally substituted with one or more —C₁-C₄alkyl, —C₀₋₄alkyl-C(O)OH, —N(R₁₃)(R₁₄), or halo; or
—C(O)N(R₄)(CH₂)₁₋₄—C(O)OR₃ and Y is a single bond, —C₁-C₄alkylene, or arylene;
—C(O)N(R₄)(CH₂)₁₋₄—N(R₁₃)(R₁₄) and Y is a single bond, —C₁-C₄alkylene, or arylene;
—N(R₄)—C(O)-heteroaryl wherein said heteroaryl is optionally substituted with halo and Y is a single bond, —C₁-C₄alkylene, or arylene;
—N(R₄)—C₁₋₄alkylene-heteroaryl and Y is a single bond, —C₁-C₄alkylene, or arylene;
—N(R₁₀)—C(O)—C(R₁₁)(R₁₂)—N(R₁₃)(R₁₄) and Y is a single bond, —C₁-C₄alkylene, or arylene;
—N(R₁₀)—C(O)—C₃₋₁₀heterocycloalkyl and Y is a single bond, —C₁-C₄alkylene, or arylene;
—N(R₄)(CH₂)₁₋₄—C(O)OR₄ and Y is C₁-C₄alkylene or arylene;
—N(R₄)C(O)C(H)(NH₂)CH₂CH₂—C(O)OR₃ and Y is arylene;
—N(R₄)C(O)C(H)(NH₂)CH₂-heteroaryl and Y is arylene;
—N(R₄)C(O)C(H)(CH₃)—NH₂ and Y is arylene;
—N(R₄)C(O)CH₂CH₂C(H)(NH₂)—COOH and Y is arylene;
—N(R₄)C(O)—C(H)(NH₂)CH₂CH₂—COOH and Y is arylene;
—N(R₄)C(O)-heteroaryl or (—N(H)C(O)isoxazolyl) and Y is arylene.

10. The method according of claim 1, wherein the compound of Formula P-I is:

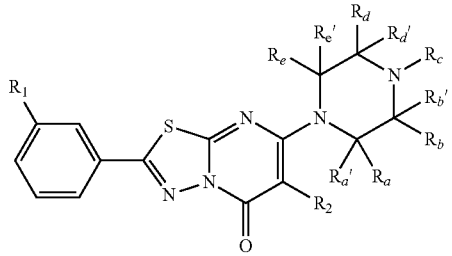

wherein
R₁ is —N(R₁₀)—C(O)—C(R₁₁)(R₁₂)—N(R₁₃)(R₁₄);
R₂ is H or halo;
R_a, R_a', R_b, R_b', R_c, R_d, R_d', R_e, and R_e' are independently H or C₁-C₄alkyl;
R₁₀, R₁₁, R₁₂, R₁₃ and R₁₄ are independently H or C₁₋₄alkyl;
in free or salt form.

11. The method of claim 1, wherein the compound of Formula P-I is a compound selected from any of the following:
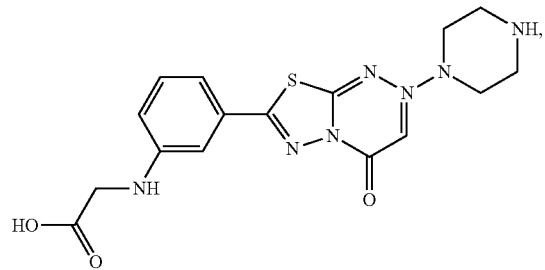
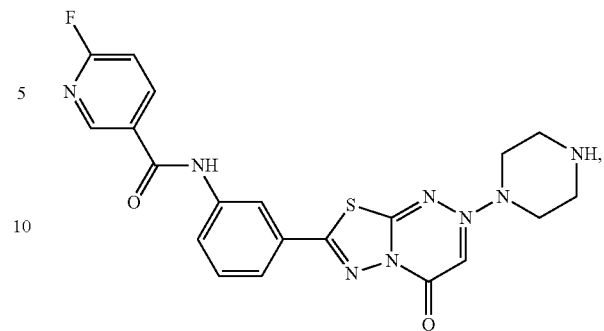
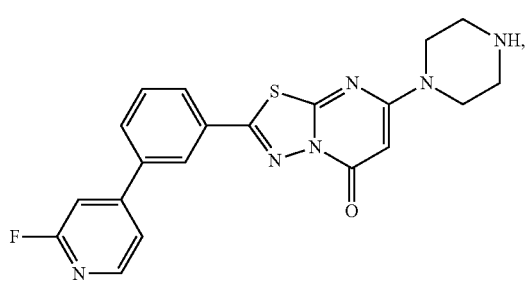
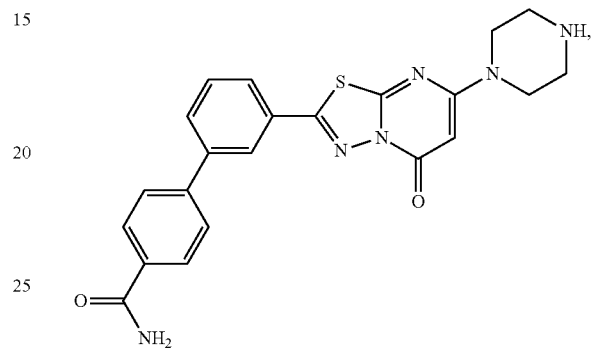
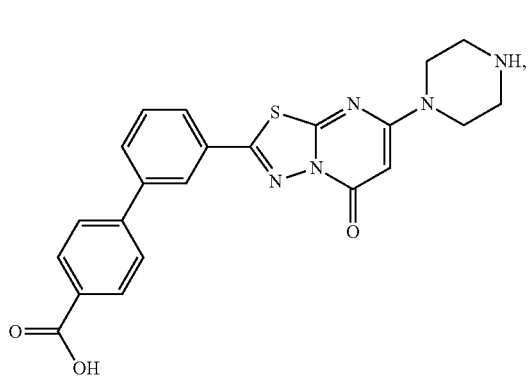
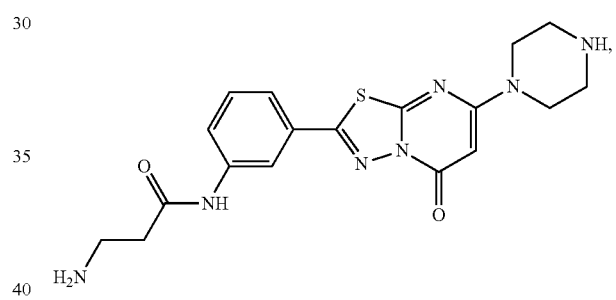
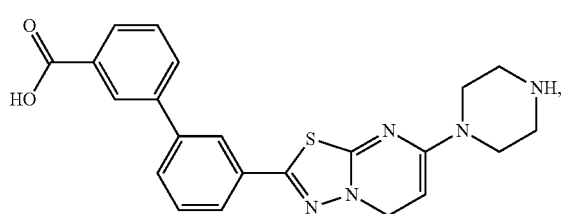
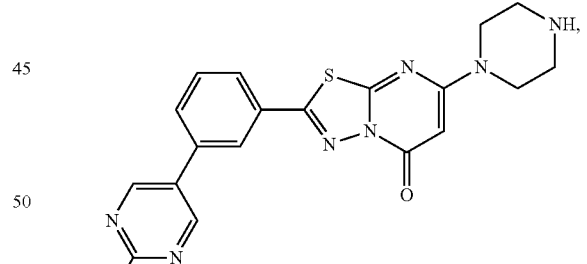
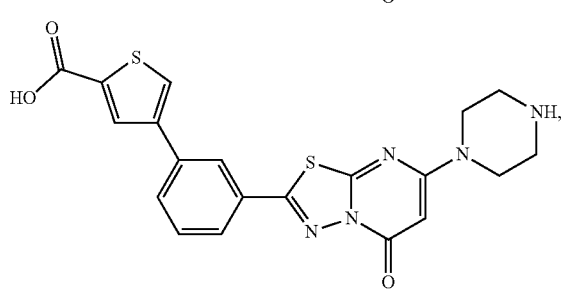
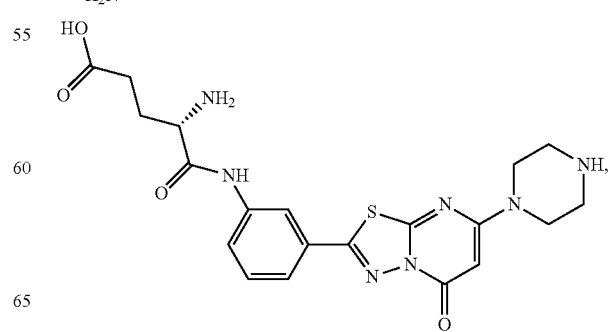

79
-continued
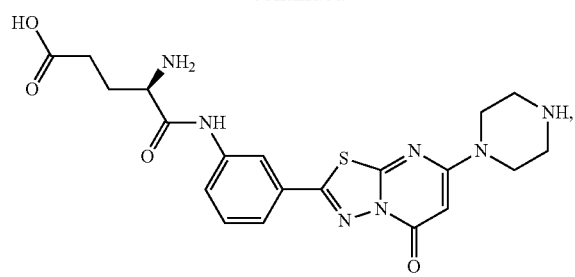
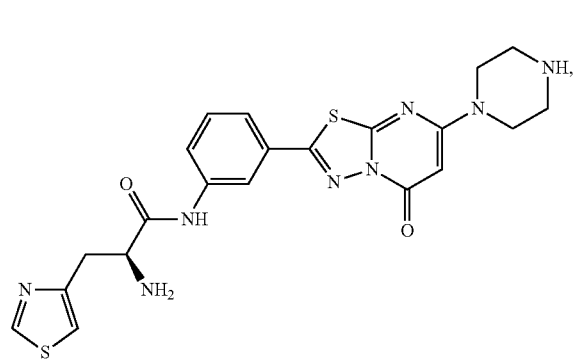
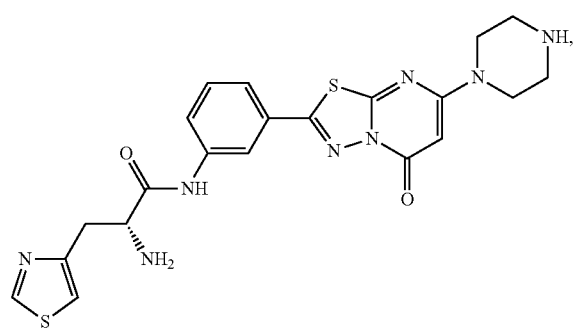
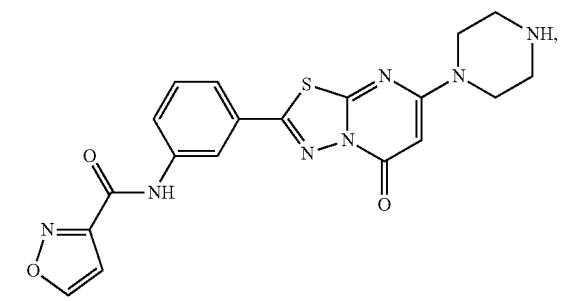
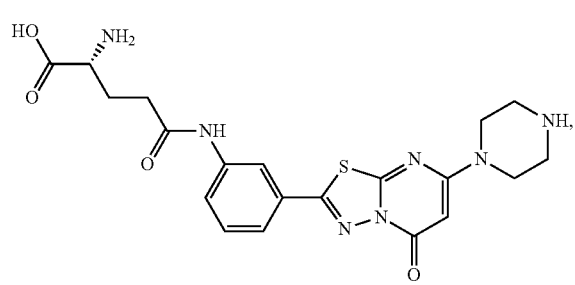
80
-continued
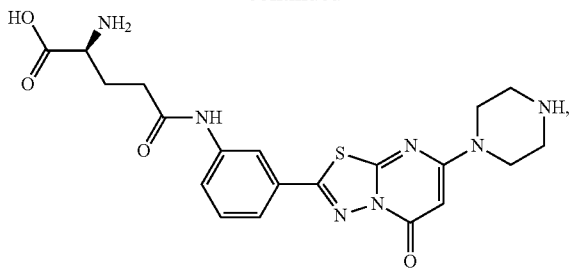
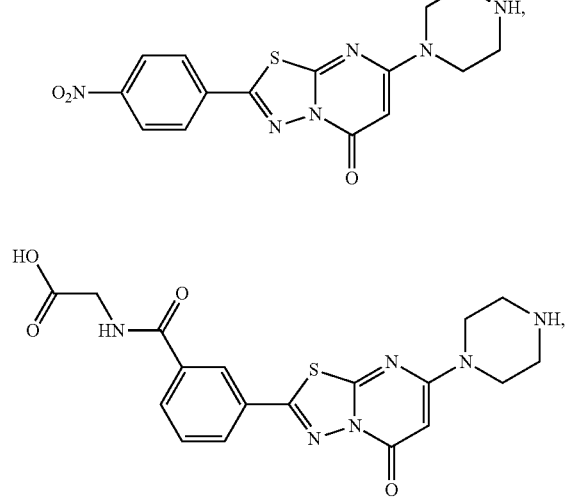
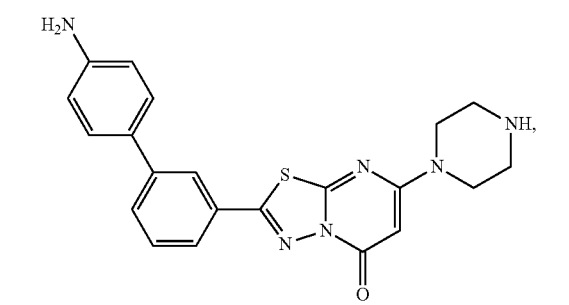
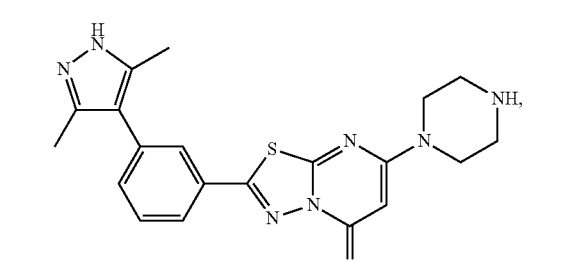
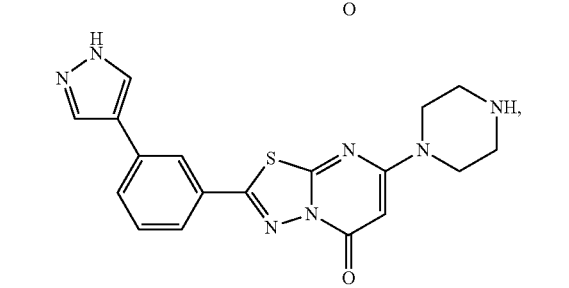

81
-continued
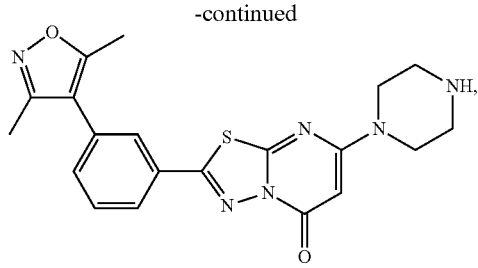
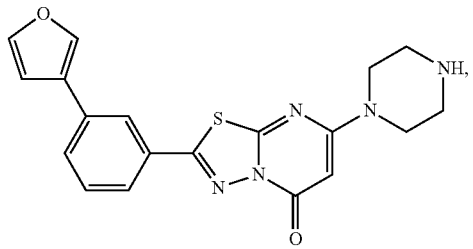
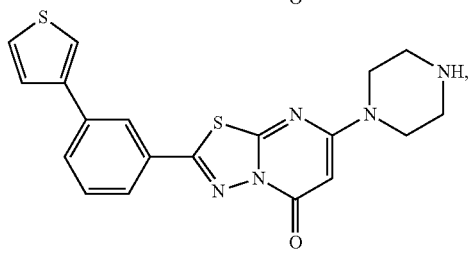
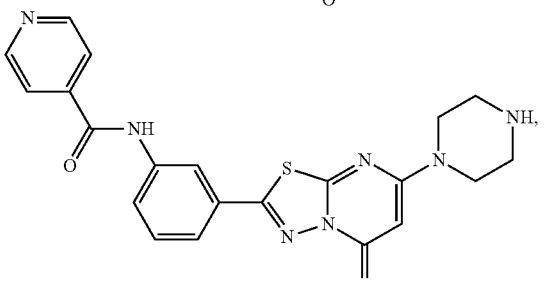
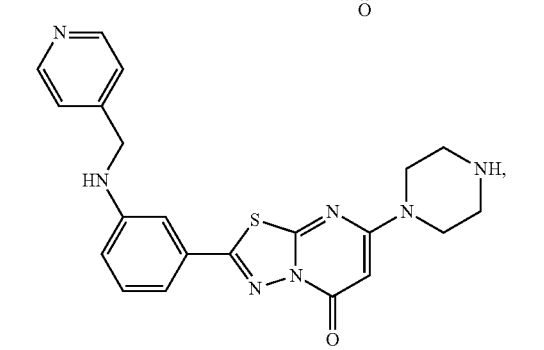
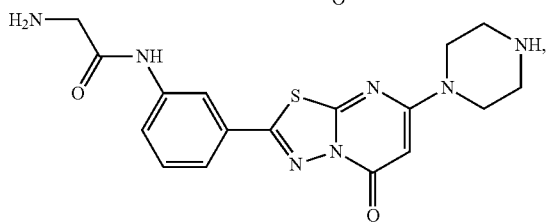
82
-continued
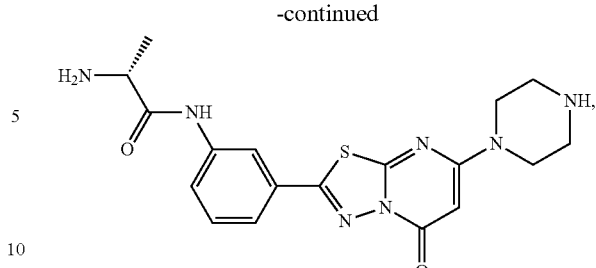
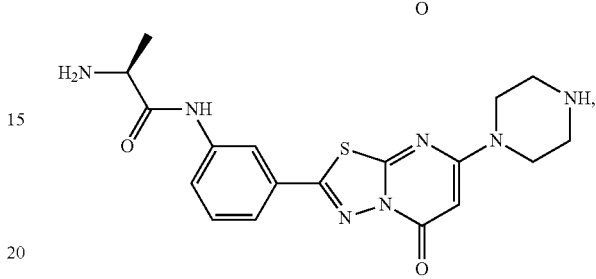
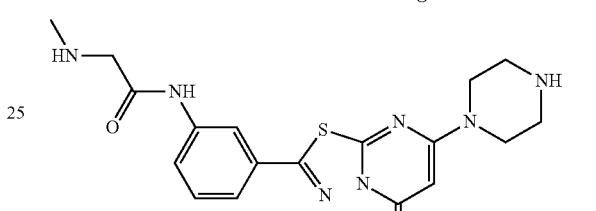
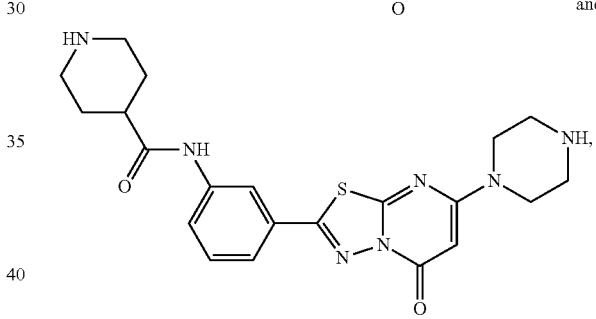
and
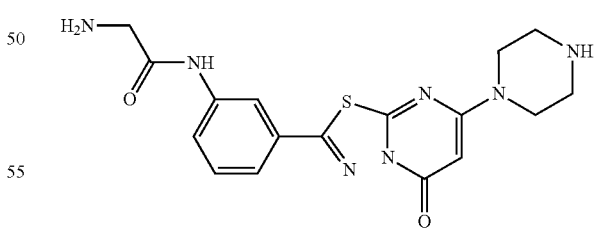
in free or salt form.
12. The method of claim 1, wherein the compound of Formula P-I is:
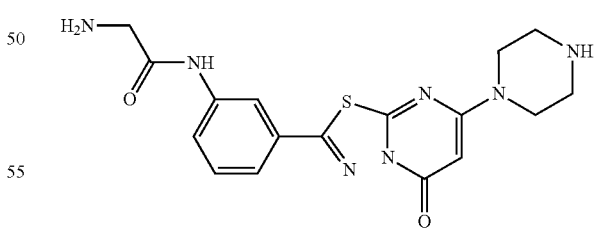
in free or salt form.
* * * * *

UNITED STATES PATENT AND TRADEMARK OFFICE
CERTIFICATE OF CORRECTION

PATENT NO. : 9,532,989 B2
APPLICATION NO. : 14/730707
DATED : January 3, 2017
INVENTOR(S) : Barry S. Coller et al.

It is certified that error appears in the above-identified patent and that said Letters Patent is hereby corrected as shown below:

In the Specification

Cross Reference to Related Applications
In Column 1, Line 13, please make the following change:
"The present invention was made with funding from National Institute of Health Grant No. HL019278." should be "The present invention was made with funding from National Institute of Health Grant Nos. HL019278 and MH083257."

Signed and Sealed this
Eighth Day of May, 2018

Andrei Iancu
*Director of the United States Patent and Trademark Office*

SEQUENCE LISTING

<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

His His Leu Gly Gly Ala Lys Gln Ala Gly Asp Val
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Engineered Polypeptide

<400> SEQUENCE: 2

Ser Phe Leu Leu Arg Asn
1               5